United States Patent [19]

Cram

[11] 4,080,337
[45] Mar. 21, 1978

[54] MULTIOXYMACROCYCLE COMPOUNDS CONTAINING PYRIDYL RINGS AS PART OF THE MACROCYCLE

[75] Inventor: Donald J. Cram, Los Angeles, Calif.

[73] Assignee: The Upjohn Company, Kalamazoo, Mich.

[21] Appl. No.: 662,564

[22] Filed: Mar. 1, 1976

Related U.S. Application Data

[62] Division of Ser. No. 505,576, Sep. 12, 1974, Pat. No. 3,965,116.

[51] Int. Cl.$^2$ ........................................... C07D 273/00
[52] U.S. Cl. ........................... 260/296 H; 260/295 R; 260/296 D; 260/297 B
[58] Field of Search ............ 260/297 B, 296 T, 296 H

[56] References Cited
U.S. PATENT DOCUMENTS 3,965,116   6/1976   Cram ................................... 260/338

OTHER PUBLICATIONS

Nachrichten aus Chemie und Technik, vol. 22, pp. 1–2 (1974).
Newcomb et al., J. Am. Chem. Soc., vol. 96, pp. 6810–6811 (Oct. 16, 1974).
Timko et al., J. Am. Chem. Soc. vol. 96, pp. 7097 to 7099 (Oct. 30, 1974).

*Primary Examiner*—Alan L. Rotman
*Attorney, Agent, or Firm*—John T. Reynolds; Willard L. Cheesman

[57] ABSTRACT

Multiheteromacrocycles are disclosed that contain as part of the macrocycle, assemblies of 2,6-dimethylyl-pyridine (and their corresponding amine oxides), 2,5-dimethylylfuran, 2,5-dimethylyltetrahydrofuran, Diels-Alder adducts of 2,5-dimethylylfuran (and their reduction products), 2- and 4-substituted 1,3-dimethylylbenzenes, pentamethylene, or p-phenylene coupled through oxygen to one another, or to ethylene, o-phenylene, or 1,1-binaphthyl-2,2- units (always coupled through oxygens) to form multidentate ligands for complexing selectively alkylammonium or metal cations.

13 Claims, No Drawings

MULTIOXYMACROCYCLE COMPOUNDS CONTAINING PYRIDYL RINGS AS PART OF THE MACROCYCLE

This work was supported in part by the U.S. Public Health Service Research Grant No. GM12640-10 from the Department of Health, Education and Welfare, and in part by a grant from the National Science Foundation, GP33533X.

This is a division of application Ser. No. 505,576, now U.S. Pat. No. 3,965,116, dated June 22, 1976, filed Sept. 12, 1974.

BACKGROUND OF THE INVENTION

Many heteromacrocycles are known that incorporate as part of the large ring structure, the simpler known heterocyclic or benzene units. For example, hemoglobin, chlorophyll, vitamin $B_{12}$, many of the macrolide antibiotics (e.g. nonactin) contain such structural units. Multiheteromacrocycles that contain as part of the major ring 2,6-substituted pyridine units have been synthesized combined with just —$CH_2CH_2$— units [J. Chem. Soc. 3594 (1958) and Chimia, 22, 306 (1968)], just —$CH_2SCH_2$— units [Tet. Letters, 3623 (1968), Chem. Ber., 102, 2677 (1969) and J. Chem. Soc., B, 2307 (1971)], just —$CH_2SCH_2$— combined with $CH_2OCH_2$ units [Nachr. Chem. Techn., 22, 2 (1974)], and just —$CH_2OCH_2$— combined with —o—$C_6H_4$— (ortho phenylene) units. Multiheteromacrocycles that contain as part of the major ring 2,5-substituted furane units have been synthesized combined with just —$CH_2CH_2$— units [J. Amer. Chem. Soc., 82, 1428 (1960)], just —CH=CH— units, just —CH=CH— units combined with 2,5-disubstituted thiophene units [Chem. Commun., 269 (1965)], just —$(CH_3)_2C$— units [J. Org. Chem., 20, 1147 (1956) and Chem. Commun., 534 (1973)], just —CH=CH— units combined with ortho-$C_6H_4$ units [J. Amer. Chem. Soc., 90, 1631 (1968)], just

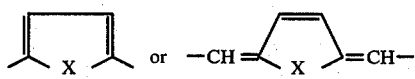

units [Chem. Commun., 23 (1969)], just —CH=CH— combined with

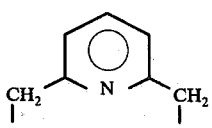

units (X = S or NH) [J. Austral. Chem., 20, 2669 (1967) and Chem. Commun., 807 (1972)], and with just a p-$CH_2CH_2C_6H_4$— $CH_2CH_2$— unit [J. Amer. Chem. Soc., 88, 515 (1966)]. Many multiheteromacrocycles that contain as part of the major ring system, 1,1-binaphthyl-2,2'-disubstituted units have been reported (U.S. Pat. Appln. Ser. No. 346,089, filed Mar. 29, 1973), but none which contain the —m—$C_6H_4$— (metaphenylene), 2,6-disubstituted pyridyl or pentamethylene units have been reported. Many multiheteromacrocycles that contain as part of the major ring system the disubstituted 2,5-dipyrrole unit have been synthesized, but only one report has appeared which involves combining it with just —$CH_2OCH_2$— units [Gazz. Chim. Ital., 62, 844 (1932)] to give:

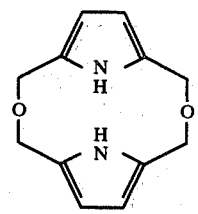

Multiheteromacrocycles that contain as part of the major ring

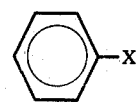

units have been synthesized combined with just —$CH_2CH_2$— units [Angew. Chem. Internat. Ed., 8, 274 (1969)], just —$CH_2SCH_2$— units [Chem. Ber., 102, 2677 (1969) and J. Chem. Soc., B, 2307 (1971)], just

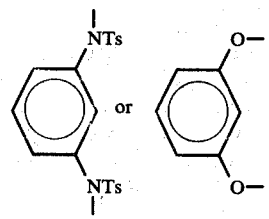

units [Chem. Ber., 102, 3071 (1969)], and with just

or —$CH_2CO_2(CH_2)_nO_2CCH_2$— units [Tet. Letters, 115 (1970)].

BRIEF DESCRIPTION OF THE INVENTION

Unique to this invention are compounds that contain only units A through L, all of which contain unit L that serves to connect all other units to one another in a ring system, and all of which contain at least one unit taken from the group, A through G.

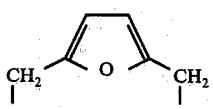

-continued

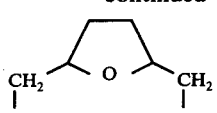

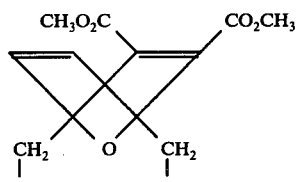

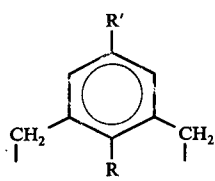

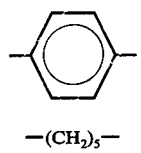

$-(CH_2)_5-$

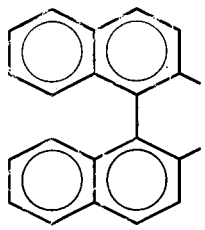

$-O-$

SUMMARY OF THE INVENTION
Character of the Compounds

This invention relates to multiheteromacrocycles of the following formula:

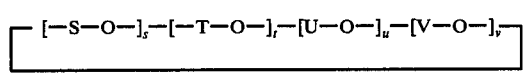

where
—S— =

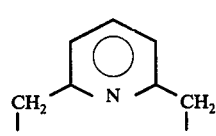

C

D

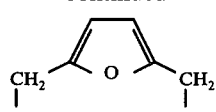

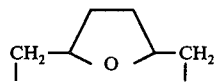

$s = 2$ through 4,
and $t=u=v= 0$;

E where
—S— = the same —S— units as above as well as

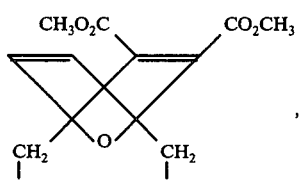

F

G $T = -CH_2-CH_2-$,
$s = 1$,

H and $t = 2$ through 7,
and $u=v= 0$;
where
—S—=U= the same initially mentioned above units,
$T=V= -CH_2-CH_2-$,
$s=u= 1$,
$t = 1$ through 6,
$v = 0$, and 1 through 6;
where
—S— =

J

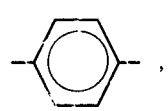

K

L $T = -CH_2-CH_2-$,
$s = 1$,
$t = 3$ through 9,
$u=v= 0$;
where
—S—=U=

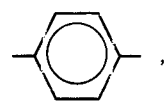

I $T=V= -CH_2-CH_2-$,
$s=u= 2$,
$t=v= 3$ through 9;
where
—S— = $-(CH_2)_5-$,
$T = -CH_2-CH_2-$,
$s = 1$,
$t = 4$,
$u=v= 0$;
where
—S—=U=

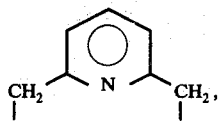

T=V= 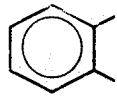 or 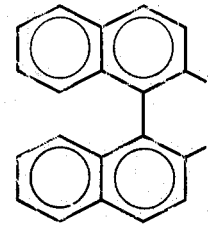, $s=u=1$,
$t=v=1$;
where
—S— =

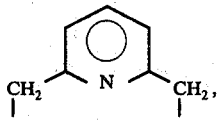

T=V= 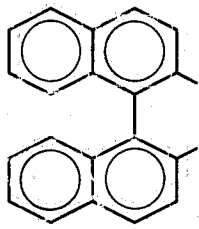,

U= 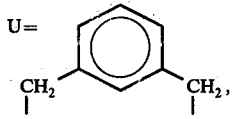

$S=t=u=v=1$;
where
—S— =

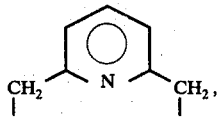

T=V= 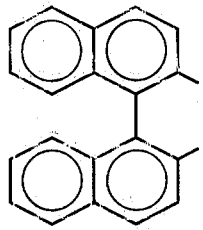,

U = —(CH$_2$)$_5$—,
$s=t=u=v=1$;
where

—S— =

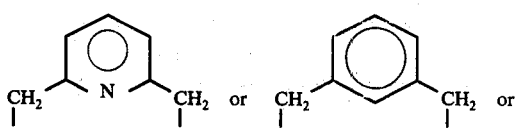

—(CH$_2$)$_5$—,

T = V = 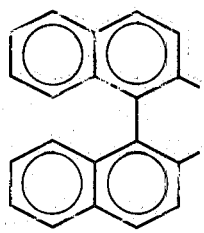,

U = —CH$_2$—CH$_2$—,
$s=t=v=1$,
$u = 2$;
where
—S— =

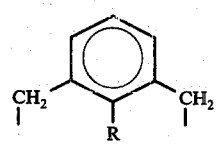

R = H, Cl, Br, CO$_2$CH$_3$, CO$_2$H, CN, CONH$_2$, NH$_2$ OH or OCH$_3$,
T = —CH$_2$—CH$_2$—,
$s = 1$,
$t = 3$ through 8,
$u=v= 0$;
where
—S— =

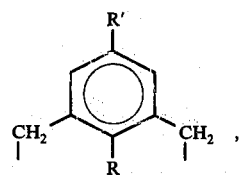

R = CO$_2$CH$_3$ or CO$_2$H (except when R' = CO$_2$CH$_3$),
R' = CO$_2$CH$_3$, CO$_2$H, CH$_2$OH, CH$_2$OCH$_2$CO$_2$CH$_3$, or CH$_2$OCH$_2$CO$_2$H,
T = —CH$_2$—CH$_2$—,
$s = 1$,
$t = 3$ through 8,
$u=v= 0$;
where
—S— =

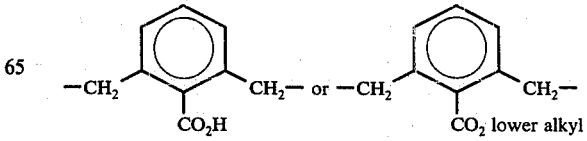

-continued

T = V = 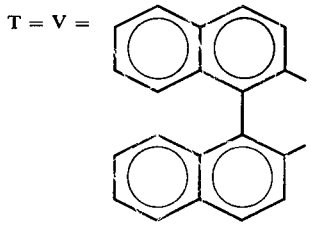,

U = —CH₂CH₂—,
s=t=v= 1,
u = 2.

Compounds I are unique in their structures, and in their cooperating molecular parts, which make them useful for the variety of purposes described below.

The systematic names of most of the compounds are too complicated for ready translation into structural formulas. Therefore structural formulas will be assigned unique numbers and specific compounds as entities will be coupled to their structures by these numbers.

Each cycle's oxygens or nitrogens provide ligands for metal, alkyl or arylammonium, hydronium or hydrogen cations. When complexed, the oxygens or nitrogens of the multiheterocycle turn toward the cation and serve as binding points to provide highly structured molecular complexes. These multiheteromacrocycles act as "host" compounds that complex "guest" compounds. The basicity and ligand properties of the heteroatoms of the above units are all different from one another, and show different tendencies to bind different cations. The sizes of the holes in the cyclic hosts have been varied to accomodate guest cations of various sizes. By loss of a proton in the units that contain acidic groups, anions have been generated in the host compounds that serve as counterions for the cations of the guest compounds. Thus complementary host-guest relationships have been arranged that involve ligand specificity, hole size and charge type.

Some of the host compounds contain chiral elements, and when optically active, the hosts complex preferentially one enantiomer of a racemate and change its solubility properties as compared to the non-complexed enantiomer. Thus optical resolutions of racemic primary amines, amino acids and their derivatives can be caused by differential distribution of diastereomeric complexes between two phases (these properties are important in applications involving countercurrent extraction and chromatographic separations).

Some of the host compounds contain both pyridine and chiral units. These compounds serve as optically active catalysts for asymmetric induction in synthesis of new chiral centers, in selective destruction of chiral centers, or in interconversion of ligands attached at chiral centers. *Synthesis of Multiheteromacrocycles*

Known compounds 1 to 5 served as starting materials for syntheses of the pyridine-containing host compounds. New open-chain compounds, 6 to 10 were prepared by the sequences formulated.

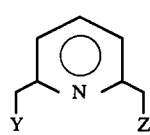

-continued

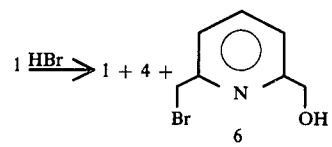

1, Y = Z = OH
2, Y = OH, Z = H
3, Y = Cl, Z = H
4, Y = Z = Br
5, Y = Z = Cl

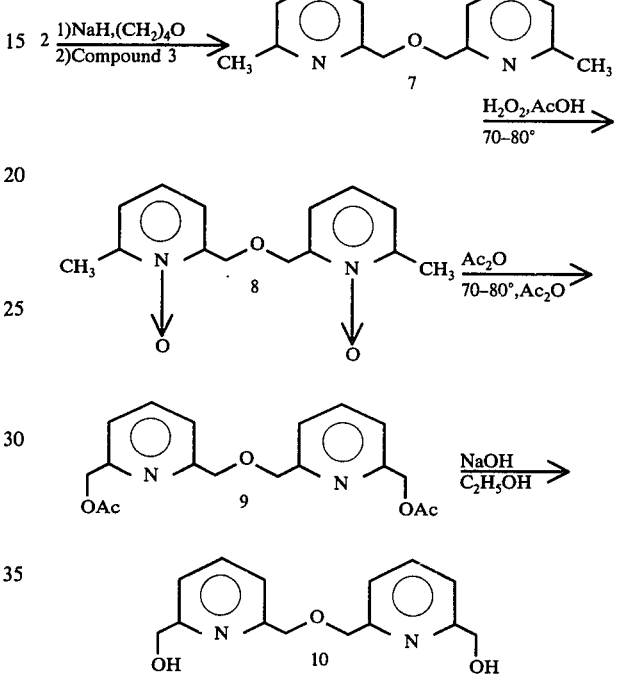

Pyridine-containing multiheteromacrocycles were prepared from open-chain compounds by the sequences formulated.

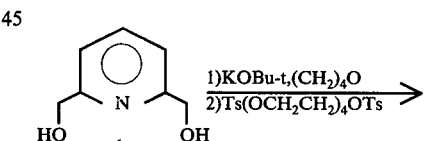

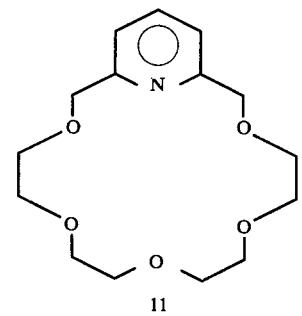

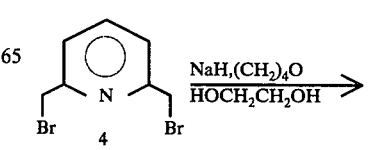

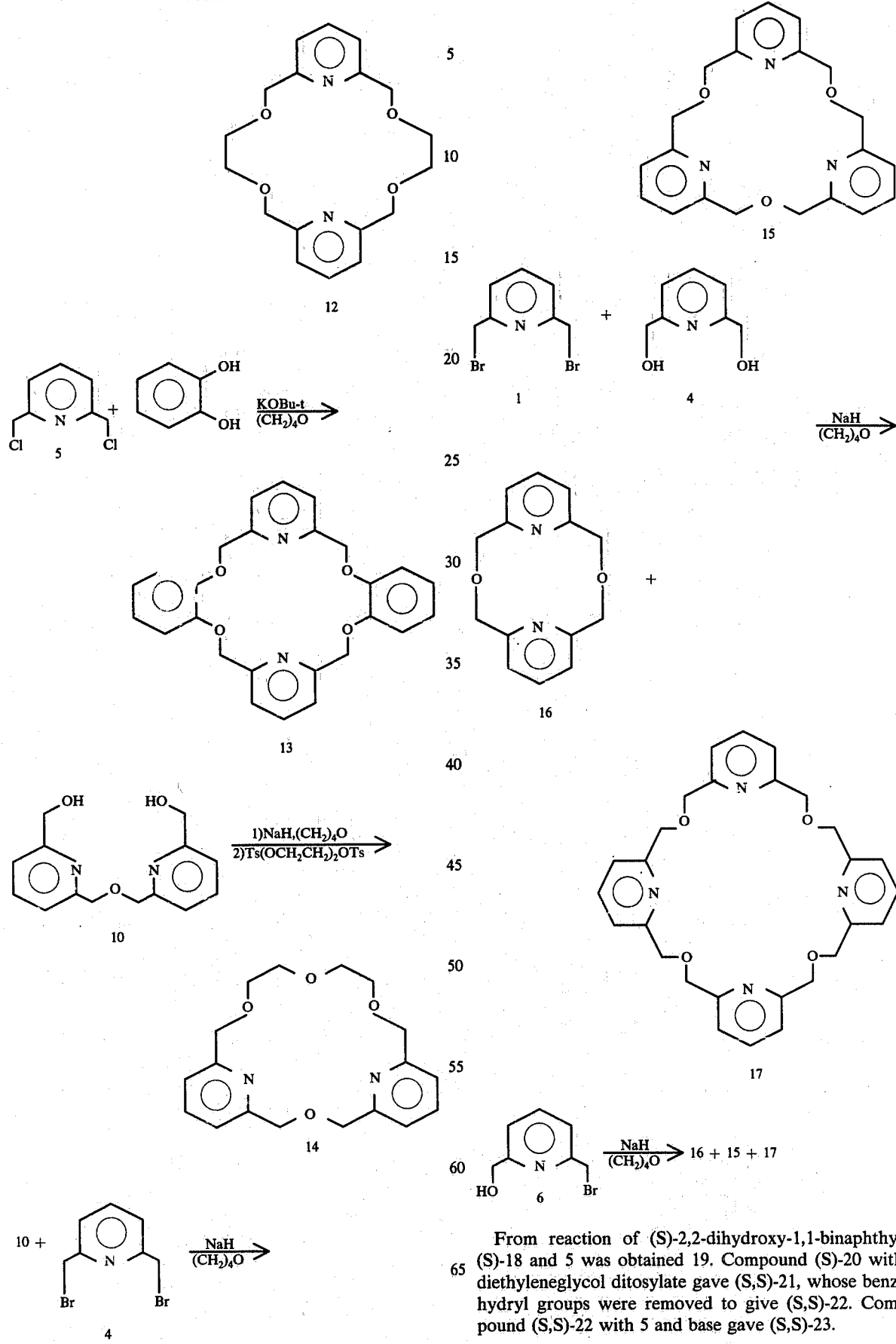
From reaction of (S)-2,2-dihydroxy-1,1-binaphthyl (S)-18 and 5 was obtained 19. Compound (S)-20 with diethyleneglycol ditosylate gave (S,S)-21, whose benzhydryl groups were removed to give (S,S)-22. Compound (S,S)-22 with 5 and base gave (S,S)-23.

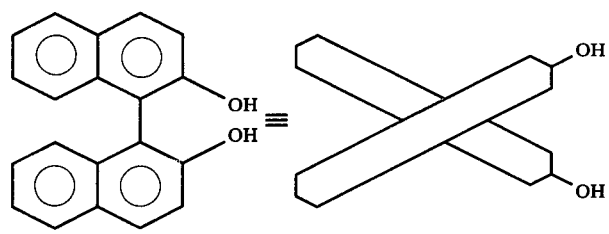
(S)-18
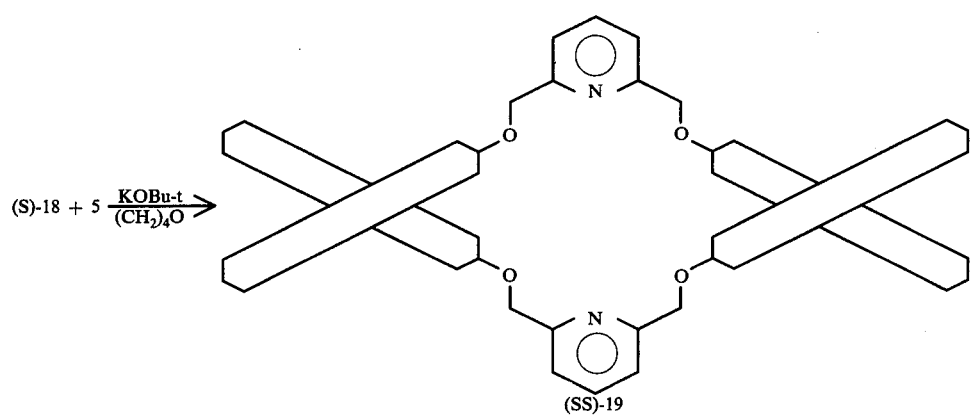
(S)-18 + 5 $\xrightarrow{\text{KOBu-t}}_{(CH_2)_4O}$
(SS)-19
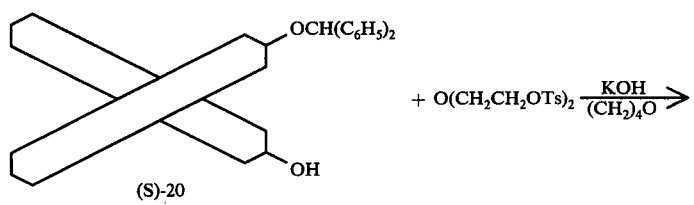
+ O(CH$_2$CH$_2$OTs)$_2$ $\xrightarrow{\text{KOH}}_{(CH_2)_4O}$
(S)-20
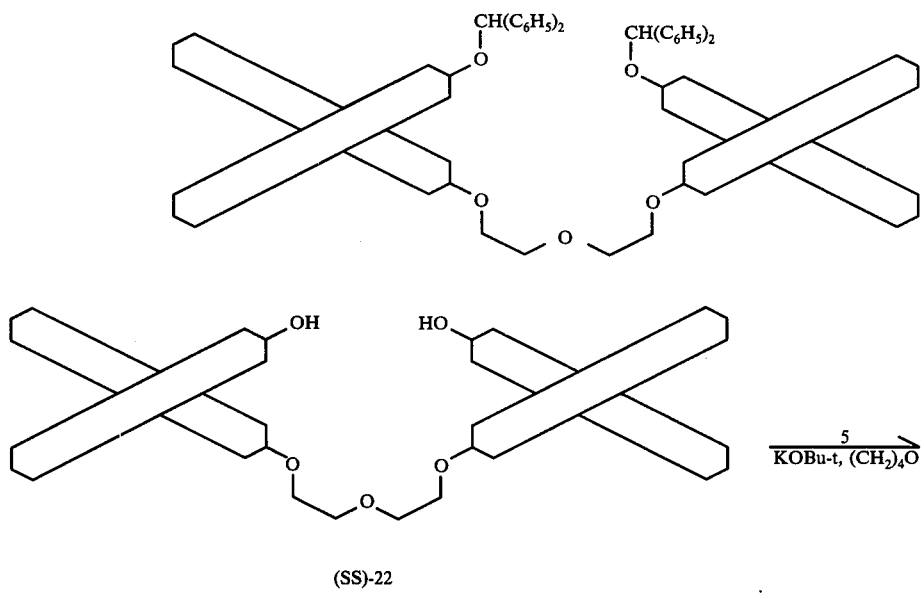
$\xrightarrow{5}_{\text{KOBu-t, (CH}_2)_4\text{O}}$
(SS)-22

-continued
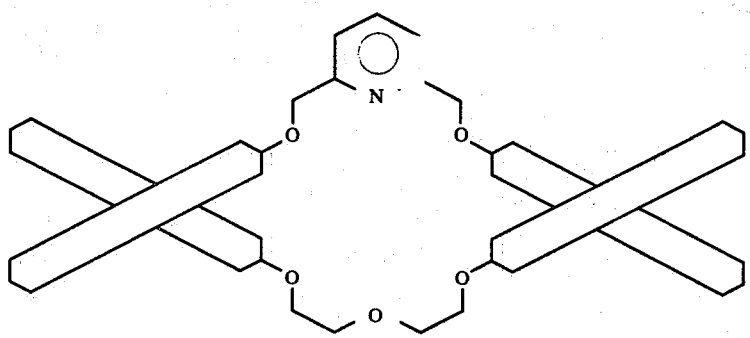
In a similar series of reactions, (SS)-23a was prepared.
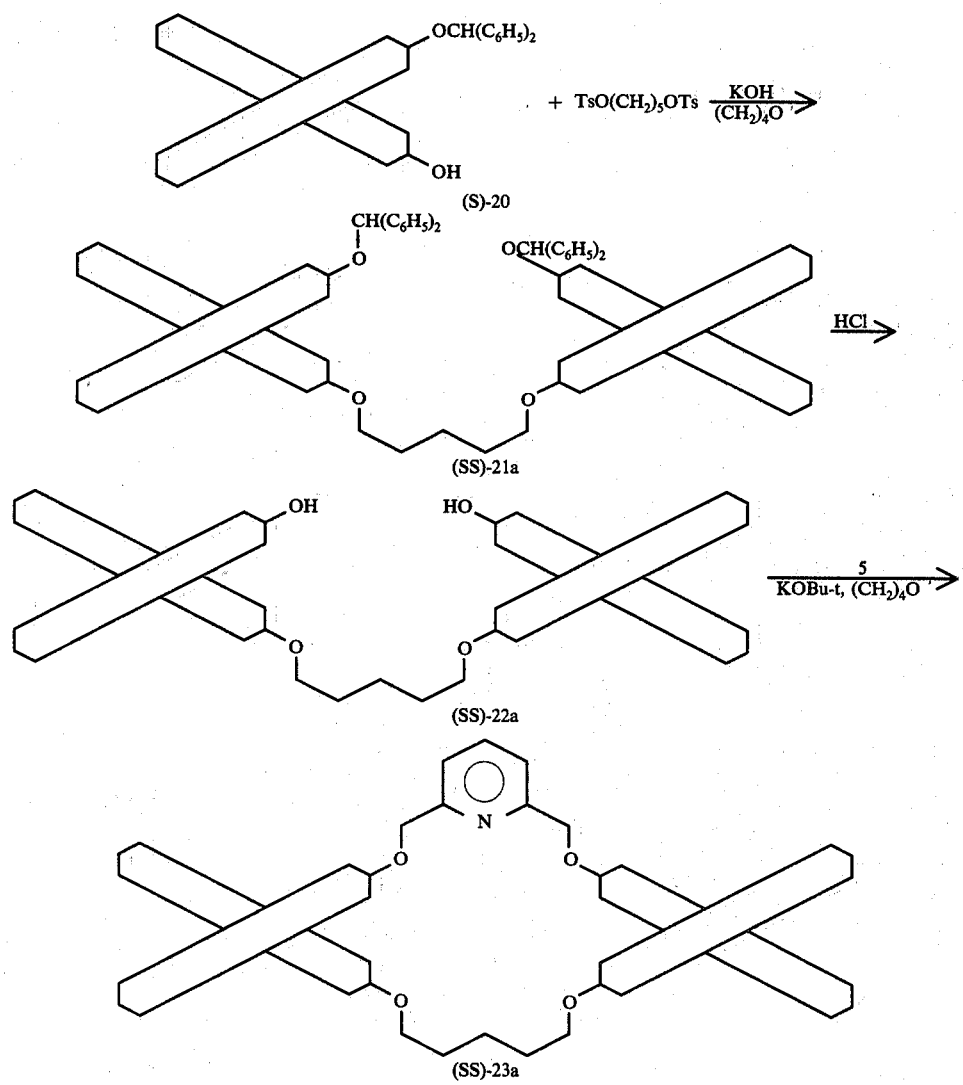
In reactions similar to 1 → 11, 1 is treated with base and diethyleneglycol, triethyleneglycol, pentaethyleneglycol and heptaethyleneglycol ditosylates to give respectively, cycles 24–28.
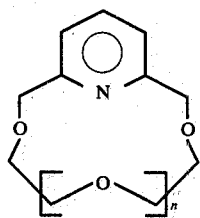

-continued
24, n = 1
25, n = 2
26, n = 4
27, n = 5
28, n = 6

In reactions similar to 4 → 12, 4 is treated with diethyleneglycol, triethyleneglycol and tetraethyleneglycol to give respectively, multiheteromacrocycles, 29–31.

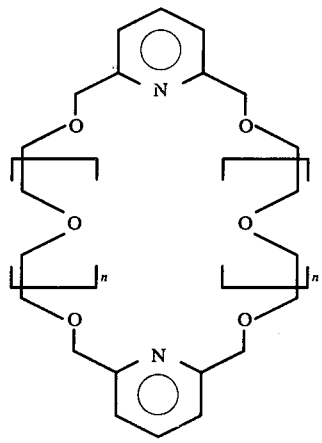

29, n = 1
30, n = 2
31, n = 3

In reactions similar to 10 → 14, 10 is treated with ethyleneglycol, triethyleneglycol, tetraethyleneglycol, pentaethyleneglyol and hexaethyleneglycol ditosylates to give respectively, multiheteromacrocycles 32–36.

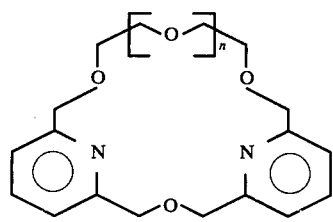

32, n = 0
33, n = 2
34, n = 3
35, n = 4
36, n = 5

The furane-containing multiheteromacrocycles involved as starting materials, 37–40 and 43, which are known compounds. Compounds 41, 42 and 44 were prepared by the indicated sequences.

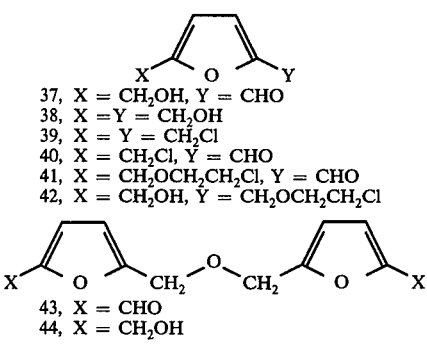

37, X = CH₂OH, Y = CHO
38, X = Y = CH₂OH
39, X = Y = CH₂Cl
40, X = CH₂Cl, Y = CHO
41, X = CH₂OCH₂CH₂Cl, Y = CHO
42, X = CH₂OH, Y = CH₂OCH₂CH₂Cl

43, X = CHO
44, X = CH₂OH

-continued

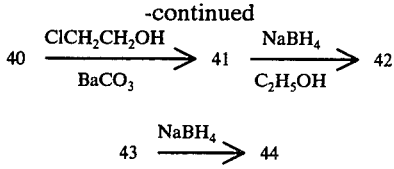

Furane-containing multiheteromacrocycles were prepared from open-chain compounds by the sequences formulated.

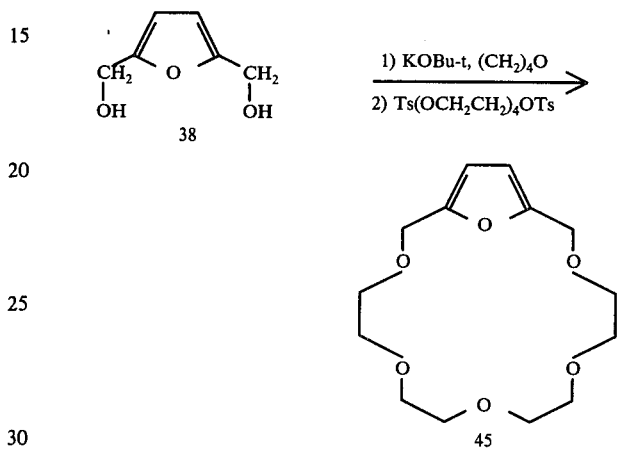

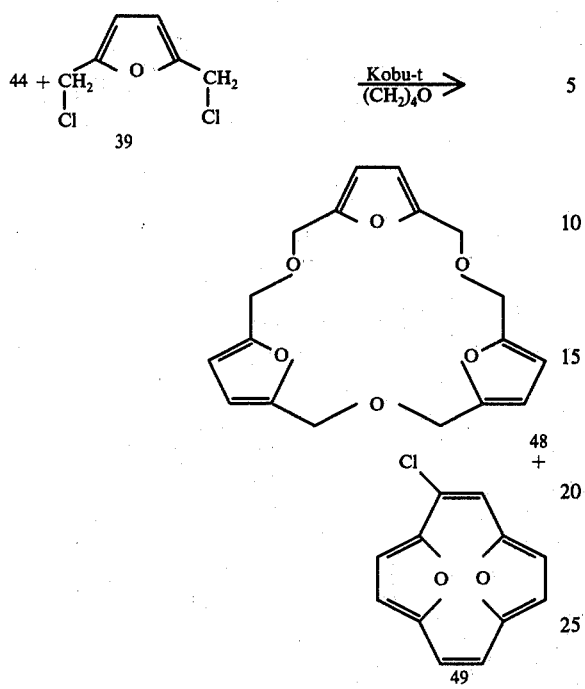

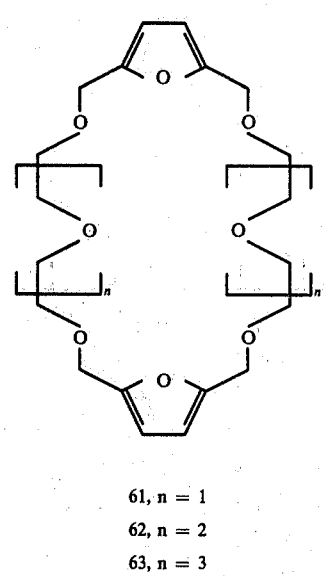

61, n = 1
62, n = 2
63, n = 3

In reactions similar to 44 → 47, 44 is treated with base and ethyleneglycol, triethyleneglycol, tetraethyleneglycol, pentaethyleneglycol and hexaethyleneglycol ditosylates to give respectively, multiheteromacrocycles 64–68.

In reactions similar to 38 → 45, 38 is treated with base and diethyleneglycol, triethyleneglycol, pentaethyleneglycol, hexaethyleneglycol and heptaethyleneglycol ditosylates to give respectively, multiheteromacrocycles 50–54.

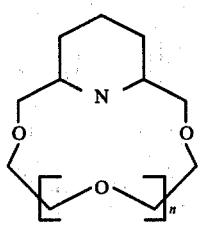

50, n = 1
51, n = 2
52, n = 4
53, n = 5
54, n = 6

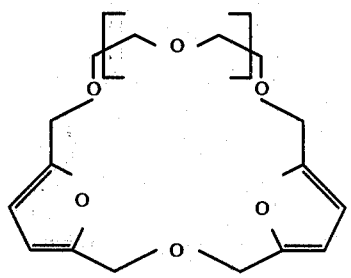

64, n = 0
65, n = 2
66, n = 3
67, n = 4
68, n = 5

In reactions similar to 40 → 41, 40 is treated with monochlorodiethyleneglycol, monochlorotriethyleneglycol and monochlorotetraethyleneglycol to give respectively 55, 56 and 57. In reactions similar to 41 → 42, 55, 56 and 57 are reduced with sodium borohydride in ethanol to give respectively 58, 59 and 60. In reactions similar to 42 → 46, 58, 59 and 60 are treated with sodium hydride in dimethylformamide to give the respective multiheteromacrocycles 61, 62 and 63.

In reaction similar to the conversion 38 → 39, 44 is treated with thionyl chloride to give 69. In a reaction similar to 44 + 39 → 48, treatment of 44 with base and 69 gives 70.

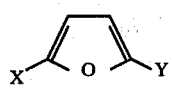

55, X = CHO, Y = CH₂(OCH₂CH₂)₂Cl
56, X = CHO, Y = CH₂(OCH₂CH₂)₃Cl
57, X = CHO, Y = CH₂(OCH₂CH₂)₄Cl
58, X = CH₂OH, Y = CH₂(OCH₂CH₂)₂Cl
59, X = CH₂OH, Y = CH₂(OCH₂CH₂)₃Cl
60, X = CH₂OH, Y = CH₂(OCH₂CH₂)₄Cl

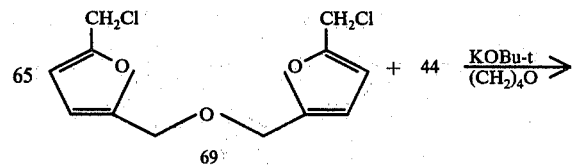

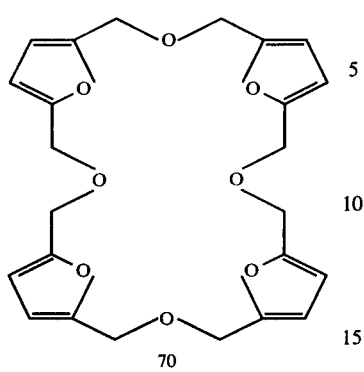

70

Catalytic reduction of furane-containing multiheteromacrocycle 45 with hydrogen and palladium-on-carbon gave the tetrahydrofurane-containing multiheteromacrocycle, 71. Similarly, furane-containing cycles 50–54, 46, 61–63, 47, 64–68, 48 and 70 are catalytically reduced to give respectively tetrahydrofurane-containing cycles, 72–88.

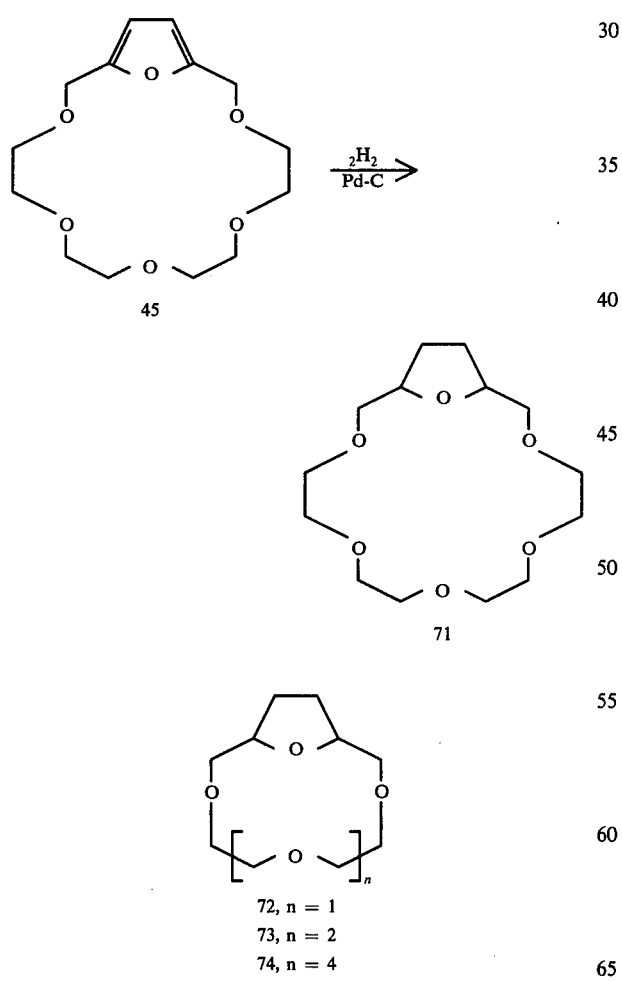

72, n = 1
73, n = 2
74, n = 4
75, n = 5
76, n = 6

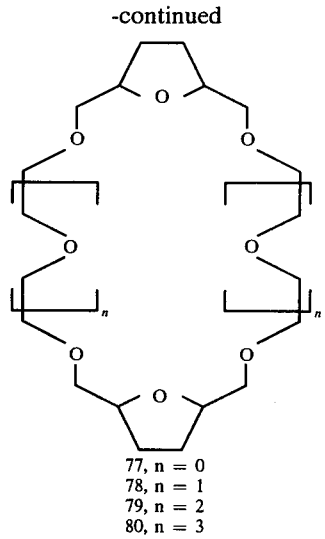

77, n = 0
78, n = 1
79, n = 2
80, n = 3

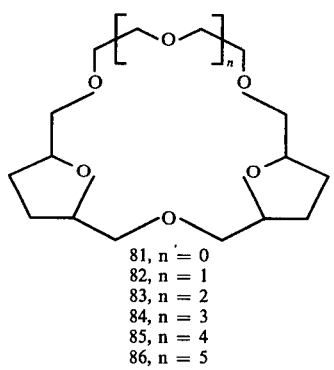

81, n = 0
82, n = 1
83, n = 2
84, n = 3
85, n = 4
86, n = 5

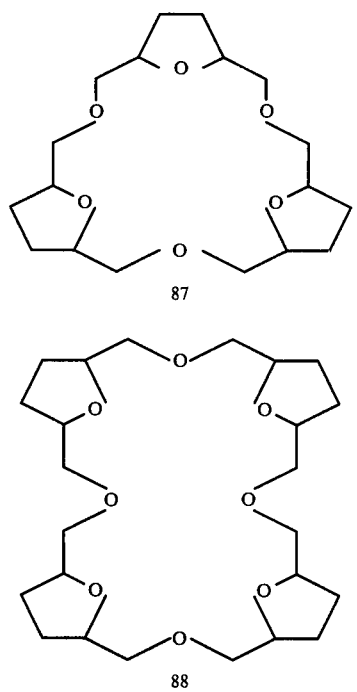

87

88

The furane-containing multiheteromacrocycles readily undergo Diels-Alder reactions when treated with dienophiles. For example, treatment of 45 with dimethyl acetylenedicarboxylic ester gave polycyclic compound 89.

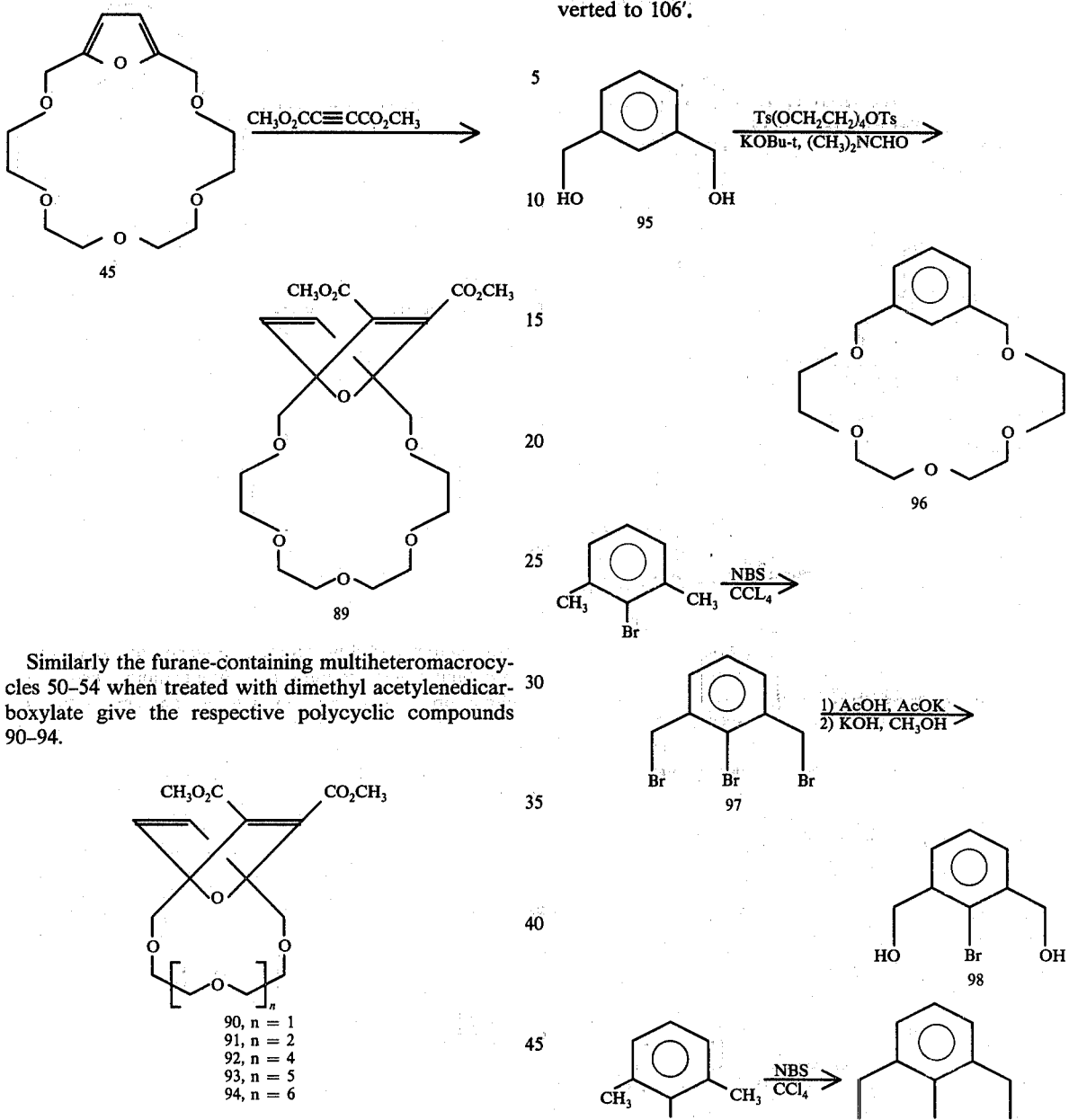

Similarly the furane-containing multiheteromacrocycles 50-54 when treated with dimethyl acetylenedicarboxylate give the respective polycyclic compounds 90-94.

Multiheteromacrocycles containing m-xylyl units were prepared as follows. Xylyl alcohol, 95, when treated with tetraethyleneglycol ditosylate in dimethylformamide and potassium tert-butoxide gave multiheteromacrocycle, 96. Treatment of 2-bromo-1,3-dimethylbenzene with N-bromosuccinimide (NBS) gave tribromide 97, which was converted to cycle 102 with base and tetraethyleneglycol. Cycle 102 was also prepared by converting 97 to diol 98, which when treated with tetraethyleneglycol ditosylate gave 102. The chlorocompound 99 was prepared from 2-chloro-1,3-dimethylbenzene by treatment with NBS. Cyclization of 99 with tetraethyleneglycol and base gave 103. Ester 100 was prepared by treating methyl 2,6-dimethylbenzoate with NBS. Diester 101 was prepared from dimethyl 2,6-dimethylterephthalate and NBS. Cyclization of 100 with tetraethyleneglycol and base gave 104, and of 101 with the same reagents, gave 106. Hydrolysis of ester 104 gave acid 105. Similar hydrolysis of 106 gives 107. In like manner, 101' was prepared and converted to 106'.

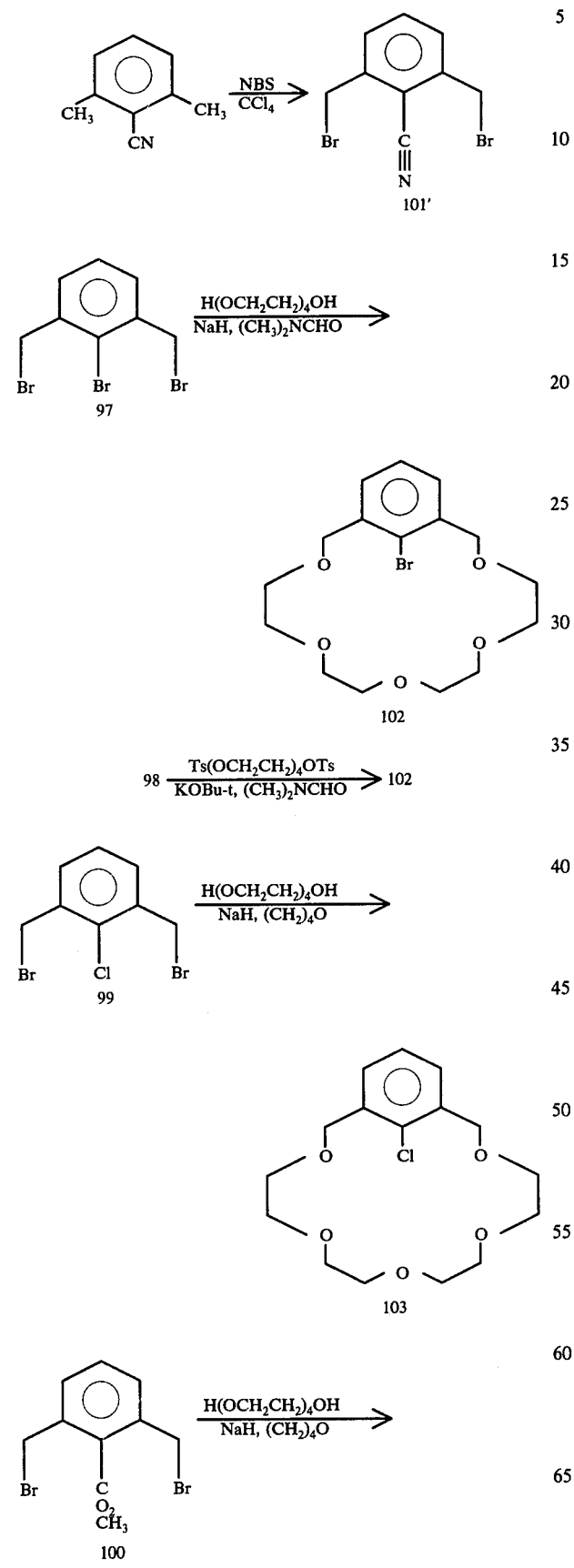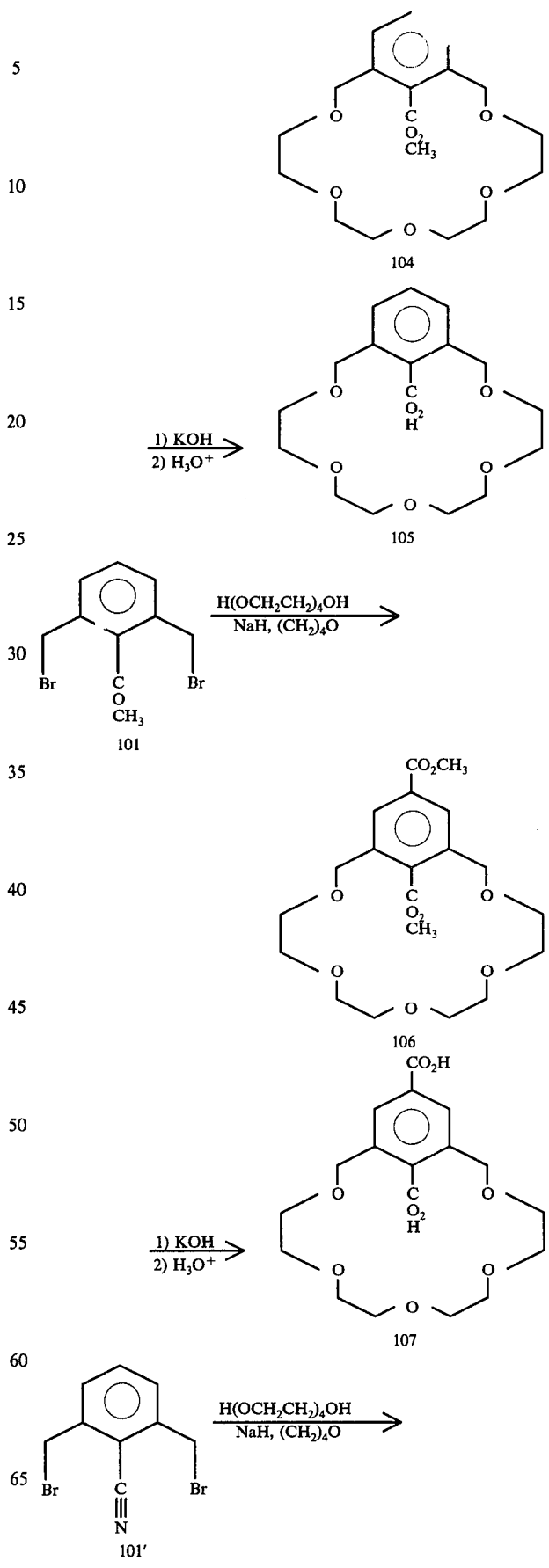

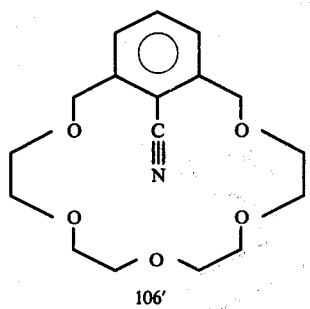

106'

Binaphthyl and m-xylyl units were combined in the following syntheses. Treatment of (SS)-22 with base and 1,3-bis-bromomethylbenzene gave (SS)-108. From (S)-20 and 1,3-bis-bromomethylbenzene was obtained (SS)-109, which was freed of its benzhydryl groups with acid to give (SS)-110. With base and 2,6-bis-chloromethylpyridine (5), (SS)-110 produced (SS)-111. Throughout these syntheses, the (R)binaphthyl unit can be substituted for the (S)-enantiomer.

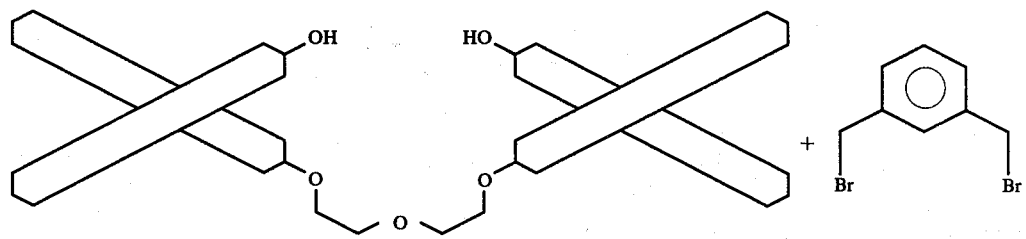

(SS)-22

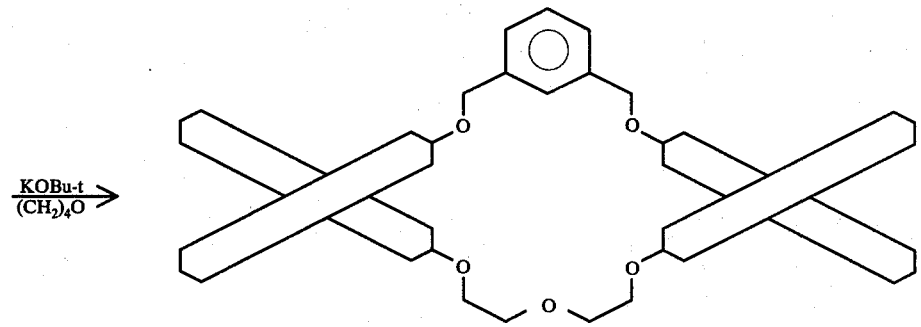

(SS)-108

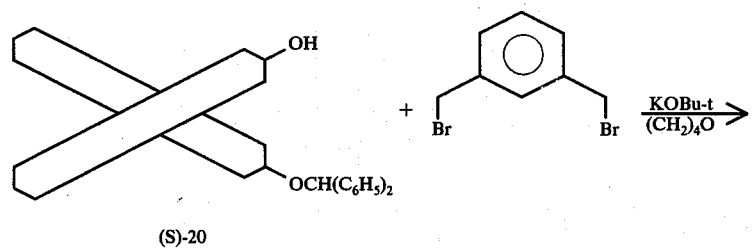

(S)-20

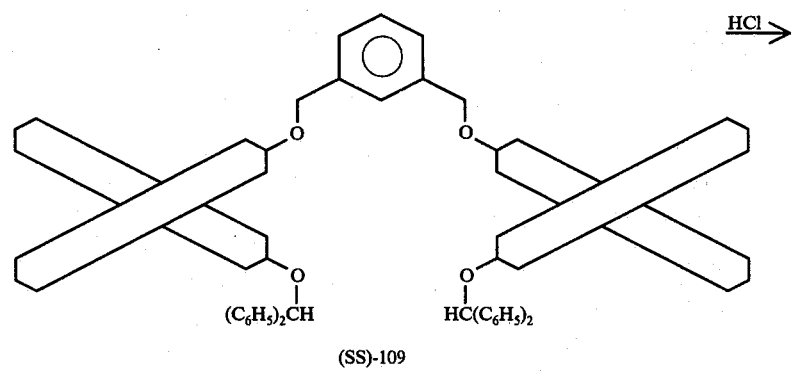

(SS)-109

-continued
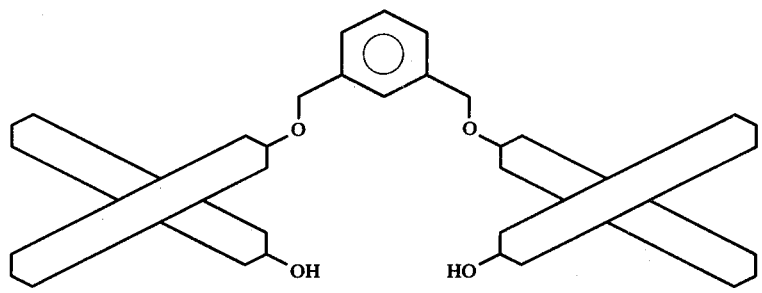
(SS)-110
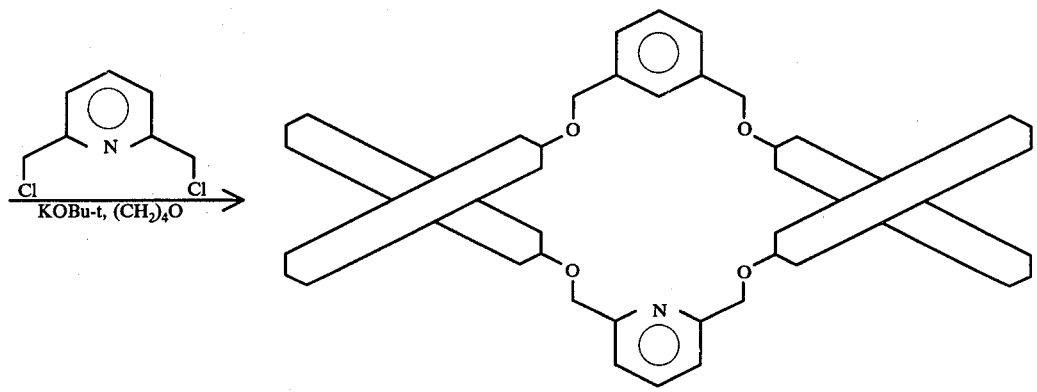
(SS)-111
By procedures similar to the syntheses of (SS)-108 and of 104 and 105, cycles (SS)-112 and (SS)-113 are prepared as formulated.
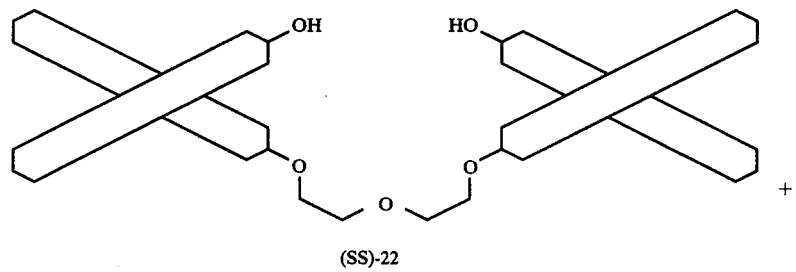
(SS)-22   +
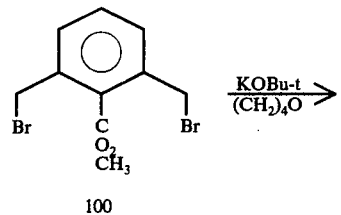
100

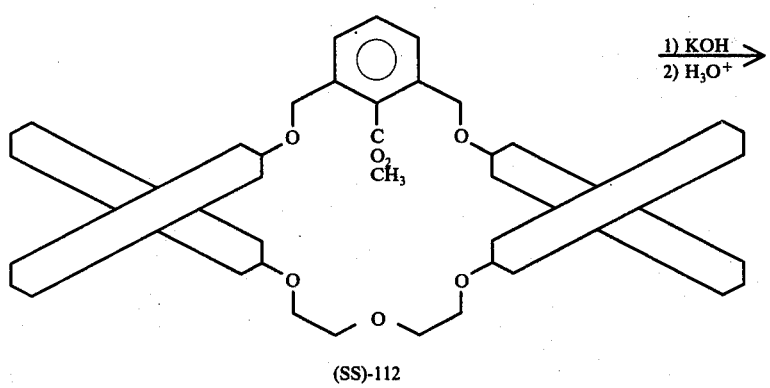

(SS)-112

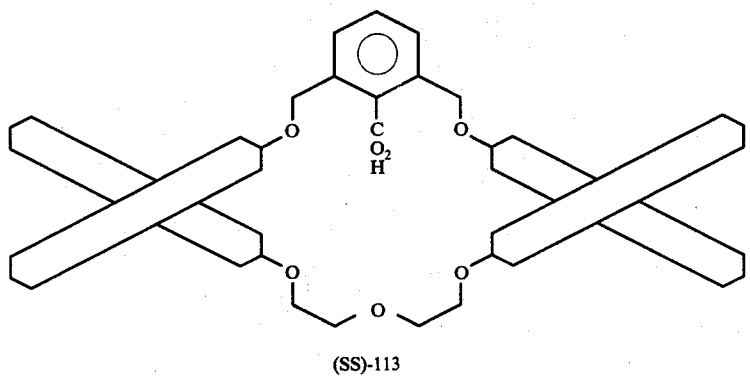

(SS)-113

By procedures similar to the syntheses of 96, 102, 103, 104–107, and by use of the appropriate ethylglycol or polyethyleneglycol or their corresponding tosylates, cycles 114–148 are prepared.

| No. | n | R | R' |
|---|---|---|---|
| 114 | 1 | H | H |
| 115 | 2 | H | H |
| 116 | 4 | H | H |
| 117 | 5 | H | H |
| 118 | 6 | H | H |
| 118a | 7 | H | H |
| 119 | 1 | Cl | H |
| 120 | 2 | Cl | H |
| 121 | 4 | Cl | H |
| 122 | 5 | Cl | H |
| 123 | 6 | Cl | H |
| 123a | 7 | Cl | H |
| 124 | 1 | Br | H |
| 125 | 2 | Br | H |
| 126 | 4 | Br | H |
| 127 | 5 | Br | H |
| 128 | 6 | Br | H |
| 128a | 7 | Br | H |
| 129 | 1 | $CO_2CH_3$ | H |
| 130 | 2 | $CO_2CH_3$ | H |
| 131 | 4 | $CO_2CH_3$ | H |
| 132 | 5 | $CO_2CH_3$ | H |
| 133 | 6 | $CO_2CH_3$ | H |
| 133a | 7 | $CO_2CH_3$ | H |
| 134 | 1 | $CO_2H$ | H |
| 135 | 2 | $CO_2H$ | H |
| 136 | 4 | $CO_2H$ | H |
| 137 | 5 | $CO_2H$ | H |

| No. | n | R | R' |
|---|---|---|---|
| 138 | 6 | $CO_2H$ | H |
| 138a | 7 | $CO_2H$ | H |
| 139 | 1 | $CO_2CH_3$ | $CO_2CH_3$ |
| 140 | 2 | $CO_2CH_3$ | $CO_2CH_3$ |
| 141 | 4 | $CO_2CH_3$ | $CO_2CH_3$ |
| 142 | 5 | $CO_2CH_3$ | $CO_2CH_3$ |
| 143 | 6 | $CO_2CH_3$ | $CO_2CH_3$ |
| 143a | 7 | $CO_2CH_3$ | $CO_2CH_3$ |
| 144 | 1 | $CO_2H$ | $CO_2H$ |
| 145 | 2 | $CO_2H$ | $CO_2H$ |
| 146 | 4 | $CO_2H$ | $CO_2H$ |
| 147 | 5 | $CO_2H$ | $CO_2H$ |
| 148 | 6 | $CO_2H$ | $CO_2H$ |
| 148a | 7 | $CO_2H$ | $CO_2H$ |

Cycles 96, 102–107 and their analogues, cycles 114–148a serve as starting materials for preparing compounds containing other functional groups either pointed inward toward (R groups), or outward away (R' groups) from the hole. The reaction sequences are exemplified with the cycles containing 18 atoms in their major ring, but are equally applicable to those with smaller or larger rings. The sequence, 105 → 149 → 150 → 151 → 152 provides the compounds with R' = H and R = $CONH_2$, $NH_2$, OH and $OCH_3$. Analogues of 149 through 152 of general formula 153 with n = 1, 2, 4, 5, 6, and 7,

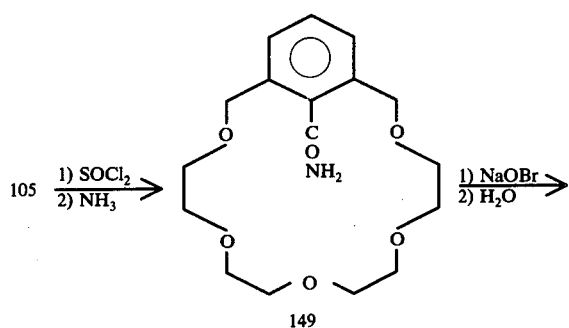
105
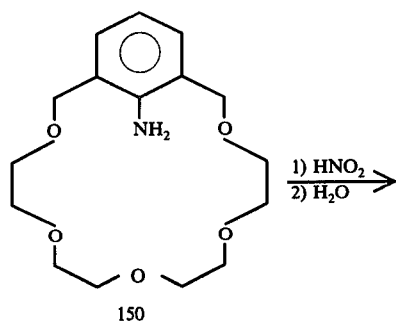
149
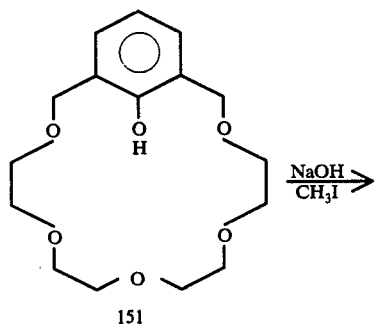
150
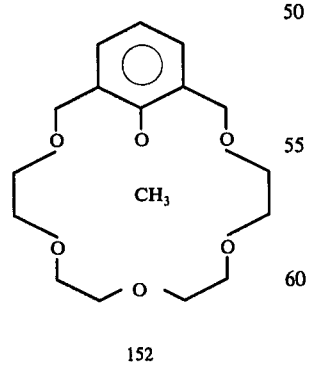
151
152
and R = CONH$_2$, NH$_2$, OH and OCH$_3$ are similarly prepared.
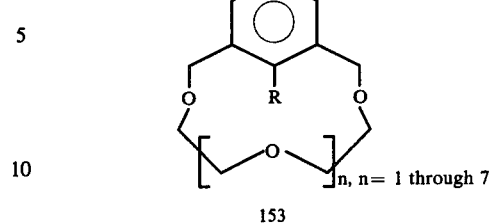
153
The sequence 106 → 154 → 155 → 156 → 157 provides a compound containing two carboxyl groups, one pointing into the hole, the other in the proper conformation reaches the edge of the hole. The first step involves hydrolysis of only the less hindered ester.
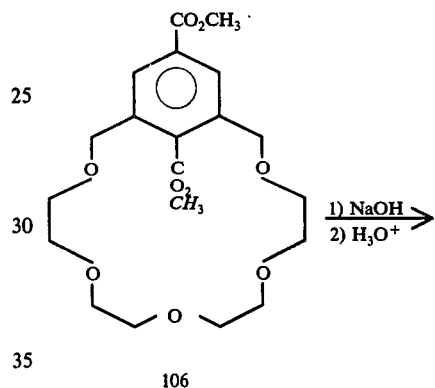
106
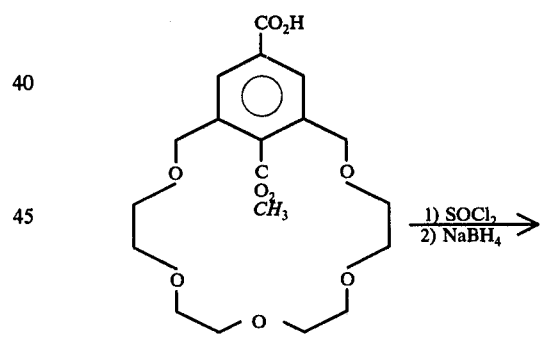
154
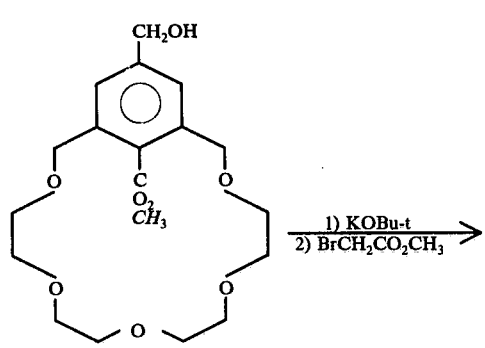
155

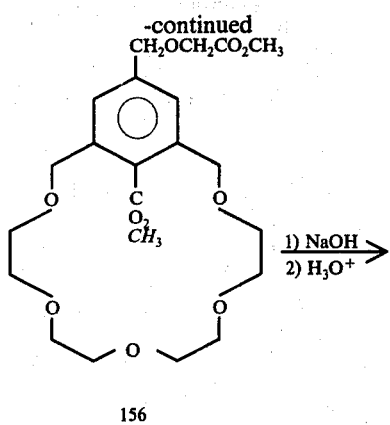

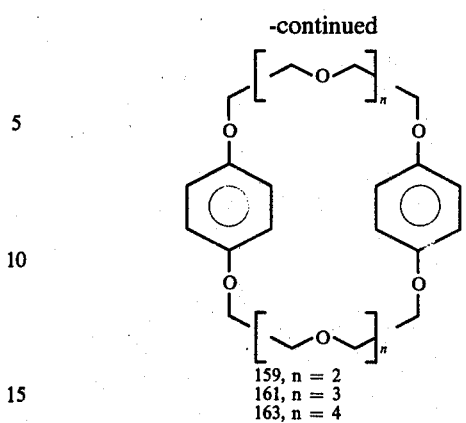

Similarly, multiheteromacrocycles 164–171 are prepared by the sequences shown.

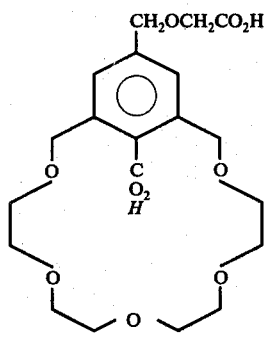

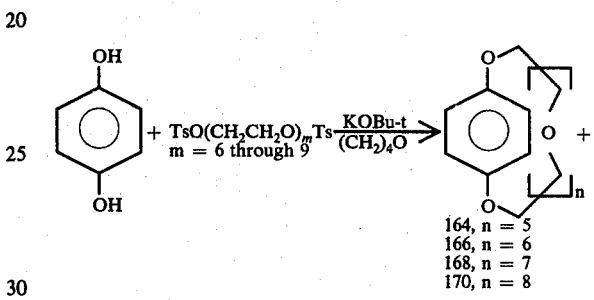

Multiheteromacrocycles 158–163 were prepared from hydroquinone, base, and the appropriate polyethyleneglycol ditosylates. Although 158 and 160 were detected in the reaction mixtures, they were not characterized.

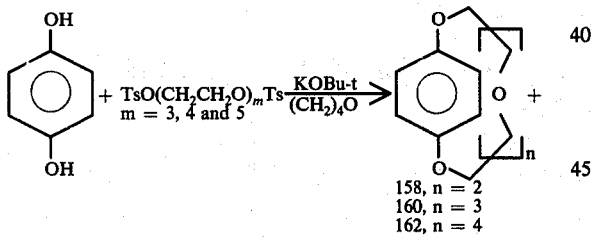

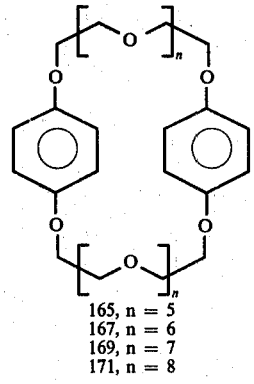

Open-chain polyether compound 172, a model for cycle 173, was prepared as formulated. Multiheteromacrocycles, 174 and 174a, that contain the pentamethylene unit, were prepared as formulated.

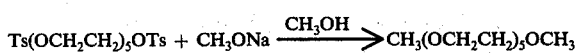

172

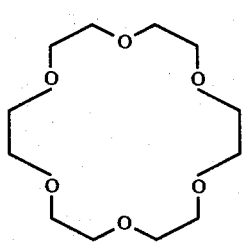

173

-continued

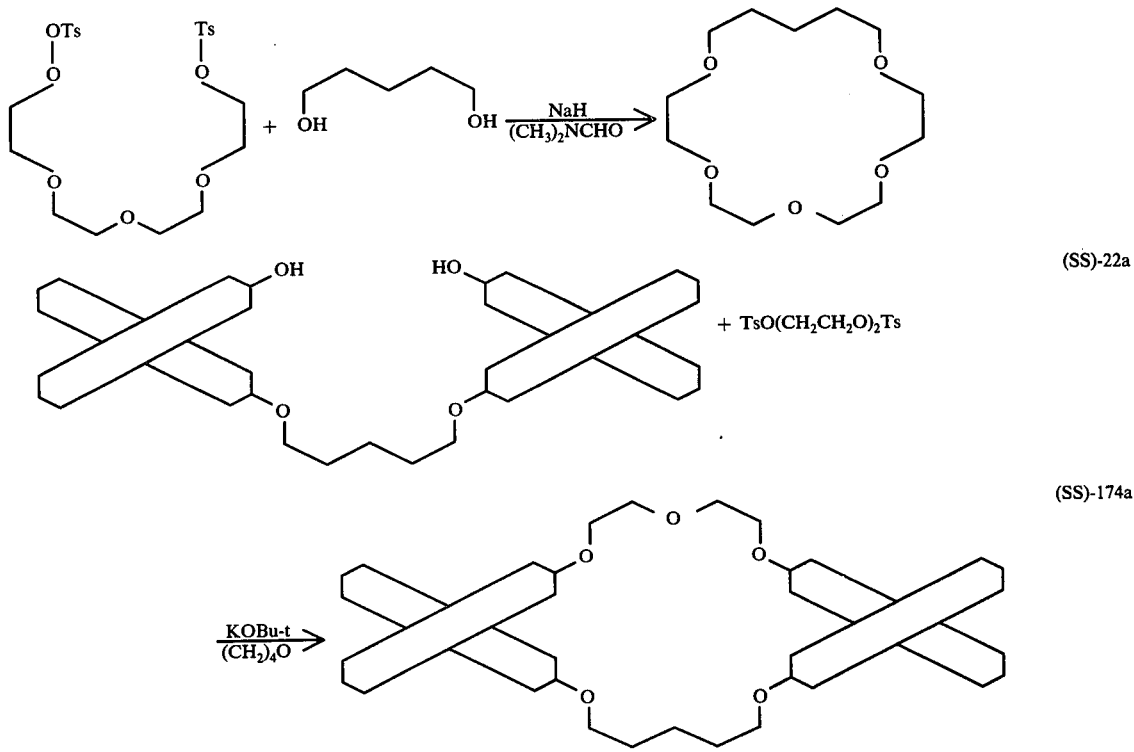

DETAILED DESCRIPTION OF THE INVENTION

General

Racemic 2,2'-dihydroxy-1,1'-binaphthyl (18) was resolved as before [Tetrahedron Lett., 3617 (1971)] to give optically pure $(+)-(R)-18$, m.p. 207.5°–208.5°, $[\alpha]_D^{25} +34.1°$ (C 1.0, $(CH_2)_4O$), and $(-)-(S)-18$, m.p. 207°–208°, $[\alpha]_D^{25} -34.3°$ (C 1.0, $(CH_2)_4O$). The absolute configurations of these isomers are established (Tetrahedron, 27, 5999 (1971)) and are formulated both in a conventional and a more illustrative form, which will be used here and elsewhere. Although optically stable at 100° for 24 hours as a solution in dioxane-water, $(-)-18$ racemized 72% with HCl ($\sim 1.2$ N) present in the same solution at 100° for 24 hours, and 69% in butanol-0.67 M in potassium hydroxide at 118° for 23 hours.

Preparation

To a solution of 28.6 g. of optically pure $(-)-(S)-18$, 11.76 g. of potassium tert-butoxide and 750 ml. of pure tetrahydrofuran stirred under nitrogen was added 26 g. of benzhydryl bromide dissolved in 250 ml. of tetrahydrofuran. The resulting solution was stirred and refluxed for 12 hours. The solvent was evaporated under vacuum, and the residue was shaken with 500 ml. of ice water and 500 ml. of dichloromethane. The organic layer was washed with 10% aqueous sodium hydroxide solution to remove any unused 18. The organic layer was washed with water, dried, evaporated and chromatographed on 700 g. of alumina. The column was washed with 2.3 liters of 15% dichloromethane in pentane, and the product eluted with dichloromethane-pentane, and the product eluted with dichloromethane-pentane (4 liter, 1:1), dichloromethane (1 liter) and 5% ethanol in dichloromethane (2 liters) to give 33 g. (73%) of $(+)-(S)-20$ as a foam, $[\alpha]_{589}^{25} +18.7°$, $[\alpha]_{578}^{25} +19.6°$, $[\alpha]_{546}^{25} +21.3°$ (C 0.55 CHCl₃).

Anal. Calcd for $C_{33}H_{24}O_2$: C, 87.58; H, 5.35. Found: C, 87.49; H, 5.57.

In the first of the following Examples, the syntheses of the new compounds are described. In the last Examples, their properties and uses are indicated. The temperatures are given in degrees centigrade.

EXAMPLE 1

Preparation of Pyridine Unit-Containing Host Compounds

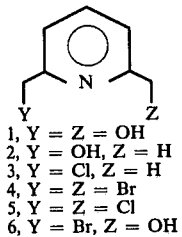

1, Y = Z = OH
2, Y = OH, Z = H
3, Y = Cl, Z = H
4, Y = Z = Br
5, Y = Z = Cl
6, Y = Br, Z = OH

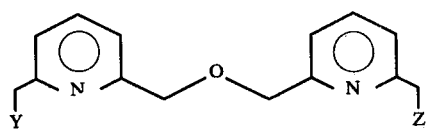

7, Y = Z = H
9, Y = Z = OAc
10, Y = Z = OH

Procedure 1

Procedure 1 reports the syntheses of the new open-chain starting materials for the preparation of the multiheteromacrocycles containing the pyridyl unit. Compound 6 was prepared as follows. Diol 1 [J. Amer.

*Chem. Soc.*, 76, 1286 (1954)], 10.0 g., was heated at reflux in 100 ml. of 48% aqueous hydrobromic acid for 1.0 hour. The solution was cooled to 0°, neutralized slowly with 40% aqueous sodium hydroxide, diluted to 300 ml., and extracted with 500 ml. of dichloromethane in five portions. The extract was dried, evaporated (vacuum) and the residue was chromatographed on silica gel (200 g.). Column elution with 2 liters of dichloromethane gave 3.0 g. (16%) of 4, m.p. 85°–89° (dec.) [*J. Chem. Soc.*, 3594 (1955)]. Elution with 2 liters of wet ether gave 6.0 g. (41%) of 6, m.p. 74°–78° (dec.), whose pmr spectrum was consistent with the assigned structure, and whose 70 eV mass spectrum gave a parent ion peak at 201.

Anal. Calcd for $C_7H_8BrNO$: C, 41.61; H, 3.99. Found: C, 41.78; H, 4.04.

Compounds 7, 9 and 10 were prepared as follows. To alcohol 2 [*J. Amer. Chem. Soc.*, 76, 1286 (1954)], 10 g., dissolved in 200 ml. of tetrahydrofuran at 25° was added 4.3 g. of 50% sodium hydride in mineral oil. The mixture was stirred 15 minutes, and 11.3 g. of 3 [*J. Chem. Soc.*, 3594 (1958)] dissolved in 50 ml. of dry tetrahydrofuran was added. After stirring for 13 hours, the mixture was quenched by addition of a small amount of water, and the solvent was evaporated under vacuum. The residue was mixed with 100 ml. of dichloromethane and 50 ml. of water. The organic phase was dried, evaporated under vacuum and chromatographed on 200 g. of silica gel with dichloromethane elution. Fractions 5–22 (500 ml. each) contained 13.4 g. (74%) of 7, m.p. 77°–78° (after recrystallization), pmr spectrum was as expected (i.e. it was consistent with the assigned structure) mass spectrum (70 eV, m/e 228 as molecular ion.

Anal. Calcd for $C_{14}H_{16}N_2O$: C, 73.66; H, 7.06. Found: C, 73.83; H, 6.90.

A solution of 9.0 g. of 7, 100 ml. of glacial acetic acid and 10 ml. of 30% aqueous hydrogen peroxide was heated at 70°–80° and stirred for 2 hours. An additional 10 ml. of 30% aqueous hydrogen peroxide was added, and the resulting mixture was heated at 70°–80° for 12 hours. The mixture was cooled and evaporated under vacuums. Water (50 ml.) was added to the residue, and the solution was again evaporated under vacuum. The residue was dissolved in chloroform, the solution was washed with 10% aqueous potassium carbonate soluton, dried, and the solvent was evaporated under vacuum to give 8.80 g. (85%) of crude di-N-oxide 8, m.p. 161°–173°.

A solution of 2.7 g. of crude 8 in 50 ml. of acetic anhydride was heated on a steam bath for 9 hours. The solvent was evaporated under vacuum, and the residue was chromatographed on 200 g. of silica gel with ethyl acetate as eluting agent. The middle fractions crystallized to give 0.63 g. of crude diacetate 9, m.p. 85°–95° (95% pure by pmr). The material was recrystallized from ethanol to give 9 as white plates, m.p. 97°–98.5°; osmometric molecular weight 352 (calculated = 344).

Anal. Calcd for $C_{18}H_{20}N_2O_5$: C, 62.78; H, 5.85. Found: C, 62.97; H, 5.97.

Hydrolysis of diacetate 9 in the usual way, i.e., with sodium hydroxide in refluxing 95% ethanol (8 hours) gave 90% of crude diol 10, which was used directly without further purification.

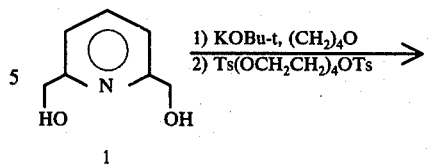

1

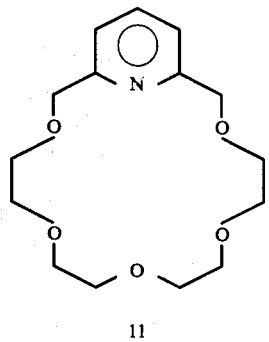

11

Procedure 2

Procedure 2 involves the synthesis of 11, and illustrates a means of incorporating one pyridyl unit into a cycle. A solution of 6.95 g. of 1, 12 g. of potassium tertbutoxide and 27 g. of tetraethyleneglycol ditosylate dissolved in 200 ml. of tetrahydrofuran was heated at reflux with stirring for 1 hour. Water (5 ml.) was added. After 20 hours of refluxing, the solution was cooled, and the potassium tosylate that precipitated was collected (16.2 g., 77%). The solvent was evaporated from the filtrate, and the residue was chromatographed on 400 g. of alumina. Elution of the column with 1% ethanol in dichloromethane gave 5.1 g. (29%) of 11, which was crystallized from dichloromethane-pentane, m.p. (sealed capiliory) 40°–41°, mass spectrum (70 eV), m/e 297 (molecular ion), pmr spectrum (60 MHz, $CDCl_3$), δ: 3.55 and 3.65 (s, s, $CH_2CH_2O$, 18H); 4.70 (s, $ArCH_2$, 4H); 6.0–7.66 (6 lines, $A_2B$, ArH, 3H).

Anal. Calcd for $C_{15}H_{23}NO_5$: C, 60.59; H, 7.80. Found: C, 60.69; H, 7.80.

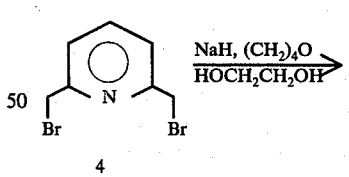

4

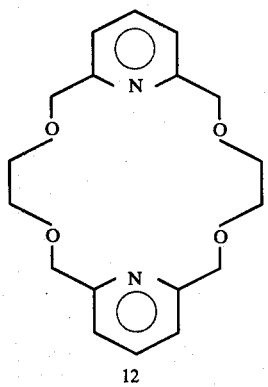

12

Procedure 3

Procedure 3 involves the synthesis of 12, and illustrates a means of incorporating two pyridyl units into a cycle. To a solution of 0.45 g. of ethyleneglycol in 100 ml. of tetrahydrofuran was added 0.80 g. of 50% sodium hydride in oil. The mixture was stirred for 30 minutes at 25°, and a solution of 1.9 g. of dibromide 4 in 100 ml. of dry tetrahydrofuran was added dropwise. The mixture was stirred at 25° for 70 hours, 30 ml. of water was added, and the solvent was evaporated under vacuum. The residue was dissolved in water, and the aqueous solution was washed with 150 ml. of dichloromethane in three portions. The combined extracts were evaporated under vacuum, and the residue was sublimed at 0.1 Torr, 130°–140°. The sublimate was recrystallized from dichloromethane-pentane to give 243 mg. (21%) of 12, m.p. 147°–148°, pmr spectrum (60 MHz, CDCl$_3$) δ: 7.1-7.7 (m, ArH, 6H); 4.53 (s, ArCH$_2$, 8H); 3.73 (s, OCH$_2$, 8H), 70 eV mass spectrum, m/e 330 (molecular ion).

Anal. Calcd for C$_{18}$H$_{22}$N$_2$O$_4$: C, 65.44; H, 6.71. Found: C, 65.58; H, 6.83.

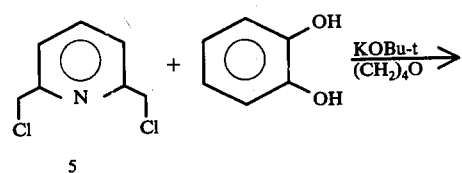

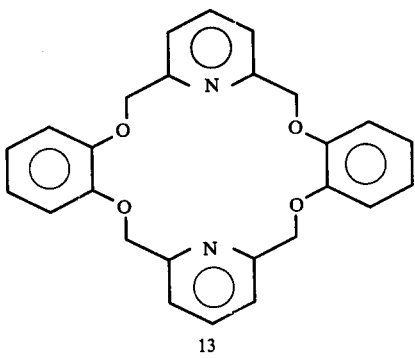

Procedure 4

Procedure 4 records the synthesis of 13 which illustrates the incorporation of pyridyl and o-phenylene units into the same cycles. To a solution of catechol (2.75 g.) and potassium hydroxide (6.16 g.) in tetrahydrofuran (450 ml.) was added 5 (+.40 g.) dissolved in 50 ml. of tetrahydrofuran. The resulting solution was stirred and heated at reflux for 24 hours, evaporated under vacuum, and chromatographed on alumina. Elution of the column with dichloromethane gave 13, 0.94 g. (9%), m.p. 184°–186° (from dichloromethane), mass spectrum (70 eV), molecular ion at m/e = 426.

Anal. Calcd for C$_{26}$H$_{22}$N$_2$O$_4$: C, 73.22; H, 5.20. Found: C, 73.13; H, 5.32.

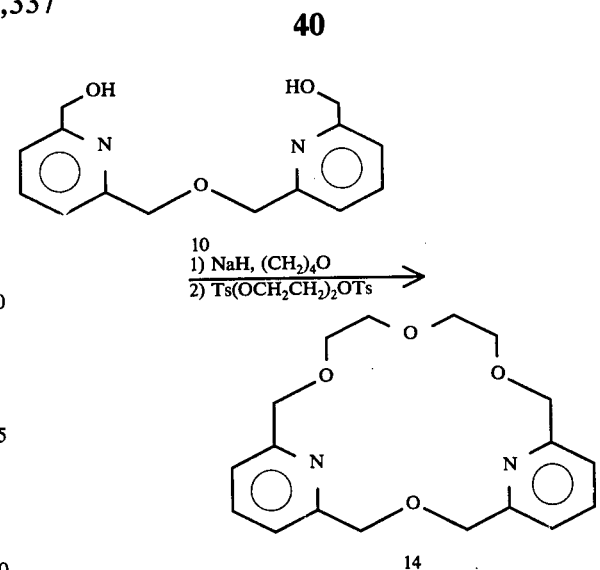

Procedure 5

Procedure 5 records the synthesis of 14 which illustrates the incorporation of two pyridyl units separated by one CH$_2$OCH$_2$ unit into cycles. To a stirred mixture of 0.77 g. of diol 10 (80% pure by pmr) and 0.75 g. of potassium tert-butoxide in 200 ml. of dry tetrahydrofuran under nitrogen was added 1.5 g. of diethyleneglycol ditosylate. The mixture was stirred at 25° for 3 days. An additional 0.10 g. of potassium tert-butoxide was added, and the mixture was heated to reflux for 4 hours. The solvent was evaporated under vacuum, and the residue was dissolved in chloroform. The chloroform solution was washed with water, dried and evaporated. The residue was chromatographed on 300 g. of alumina with benzene-ethanol as eluting solvent. Cycle 14 was obtained as an oil which was subjected to gel permeation chromatography (Bio Beads SX-8) to give 0.15 of a mixture of 80% 14 and an impurity identified by its pmr spectrum as probably

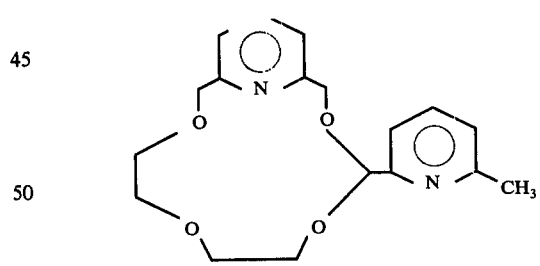

The identity of 14 was established by its gel permeation chromatography retention volume in relation to that of cycles 11, 12 and 15, and particularly by its 60 MHz pmr spectrum in CDCl$_3$, δ: 6.9–7.7 (m, ArH, 6H); 4.7 (s, ArCH$_2$, 4H); 4.5 (s, ArCH$_2$, 4H); 3.6 (s, CH$_2$CH$_2$O, 8H).

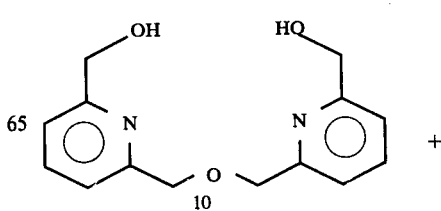

-continued

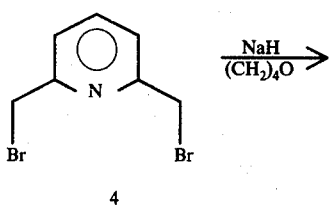

4

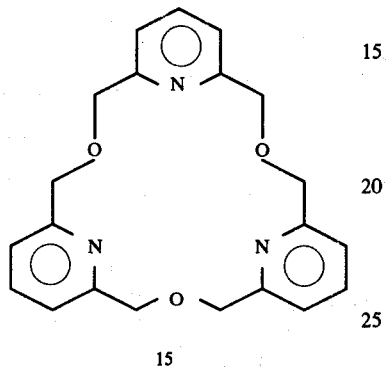

15

Procedure 6

Procedure 6 records the synthesis of 15 from 10 and 4. To a solution of 1.07 g. of diol 10 in 200 ml. of tetrahydrofuran was added 0.50 g. of 50% sodium hydride suspended in oil, and the mixture was stirred at 25° for 30 min. A solution of 1.2 g. of dibromide 4 in 100 ml. of dry tetrahydrofuran was added over 1 hour, and the mixture was stirred for 13 hours at 25°, and mixed with water. The solvent was evaporated under vacuum, and the residue was chromatographed on 250 g. of alumina. Products were eluted with 5 liters of dichloromethane and 2 liters of 1% ethanol in dichloromethane. The latter fractions contained 15, which was submitted to gel permeation chromatography on Bio Beads SX-8 (149 ml. retention volume) to give 0.480 g. (32%) of 15, which was recrystallized from dichloromethanepentane, m.p. 125°–128° (dec), osmometric molecular weight, 359 (calculated 363), 60 MHz pmr spectrum in CDCl$_3$, δ: 7.1–7.8 (m, ArH, 9H): 4.6 (s, ArCH$_2$, 12H).

Anal. Calcd for C$_{21}$H$_{21}$N$_3$O$_3$: C, 69.40; H, 5.82. Found: C, 69.18; H, 6.03.

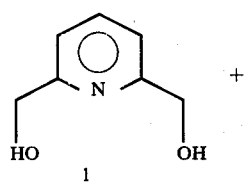

1

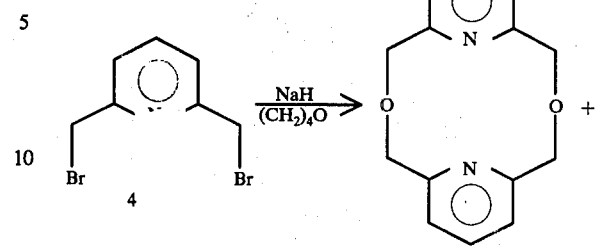

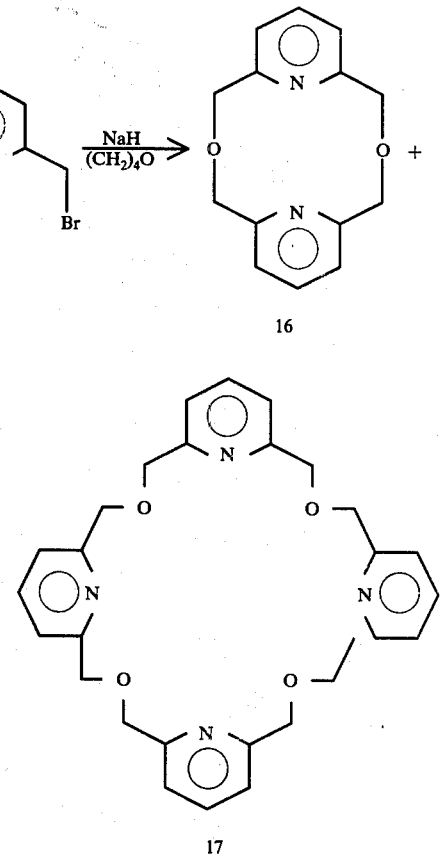

Procedure 7

Procedure 7 records the synthesis of 16 and 17 from 1 and 4. To a solution of 1.4 g. of diol 1 in 100 ml. of dry tetrahydrofuran was added 1.10 g. of 50% sodium hydride in oil. After the mixture had stirred for 45 minutes at 25°, a solution of 2.6 g. of 4 in 100 ml. of dry tetrahydrofuran was added, and the mixture was stirred for 100 hours at 25°. Water (2 ml.) was added, the mixture was filtered, the residue was washed with dichloromethane, and the combined filtrates were evaporated under vacuum. The residue was chromatographed on 100 g. of alumina with 1% ethanol in dichloromethane. Cycles 16 and 17 eluted in early fractions. The combined fractions were chromatographed on 500 g. of silica gel with dichloromethane-ethanol as eluting agent. The first eluting cycle was 17, 320 mg. m.p. 170°–173°. The second eluting fraction contained a mixture of 16 and 17, which were separated by gel permeation chromatography (Bio Beads SX-8) to give 160 mg. of 17, and 20 mg. (1%) of 16. Cycle 16 was identified by comparison (m.p., pmr, retention volume) with authentic material prepared in Procedure 8. Cycle 17, 20%, gave m.p. 173°–176° (dec.), 60 MHz pmr spectrum in CDCl$_3$, δ: 7.1–7.7 (m, ArH, 12H); 4.6 (s, ArCH$_2$, 16H), and osmometric molecular weight 466, calculated 484.

Anal. Calcd for C$_{28}$H$_{28}$N$_4$O$_4$: C, 69.40; H, 5.82. Found: C, 69.34; H, 6.00.

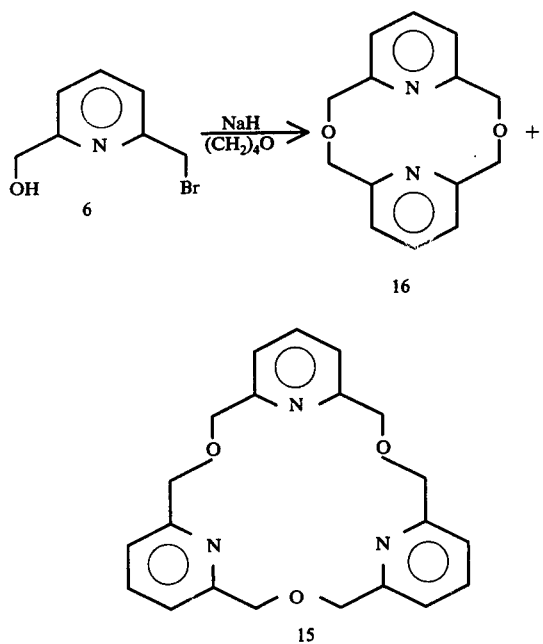

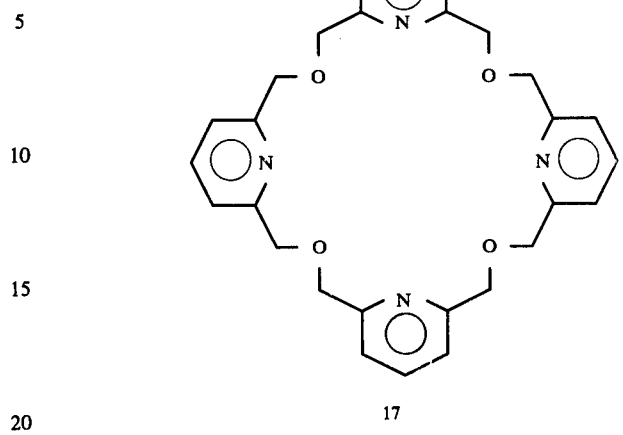

Procedure 8

Procedure 8 records the synthesis of 16, 15 and 17 from 6. A mixture of 5.3 g. of 6, 1.5 g. of 50% sodium hydride in oil, and 500 ml. of dry tetrahydrofuran was stirred at 25° for 100 hours. Water, 3 ml., was added, the mixture was filtered, the cake was washed with dichloromethane, and the filtrate was evaporated under vacuum. The residue was chromatographed on 60 g. of alumina with dichloromethane as eluting agent. The early eluting material was rechromatographed on 200 g. of silica gel with dichloromethane-ethanol as eluting agent. The cycles eluted in the order, 17 (172 mg. or 6%), 15 (30 mg. or 1%) and 16 (202 mg. or 6.5%), m.p. 170–175 (dec.). The samples of 17 and 15 were found identical in all respects (m.p., pmr and gel permeation retention volumes) with authenic material. The sample of 16 was recrystallized from dichloromethanepentane to give material, m.p. 172°–175° (dec.), pmr spectrum (60 MHz) in $CDCl_3$, δ: 6.7-7.4 (m, ArH, 6H); 4.6 (s, $ArCH_2$, 8H), osmometric molecular weight 239 (calculated 242).

Anal. Calcd for $C_{14}H_{14}N_2O_2$: C, 69.40; H, 5.82. Found: C, 69.45; H, 5.83.

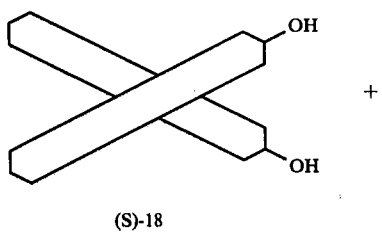

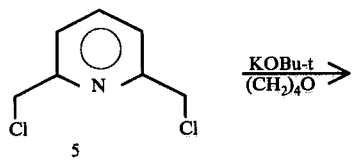

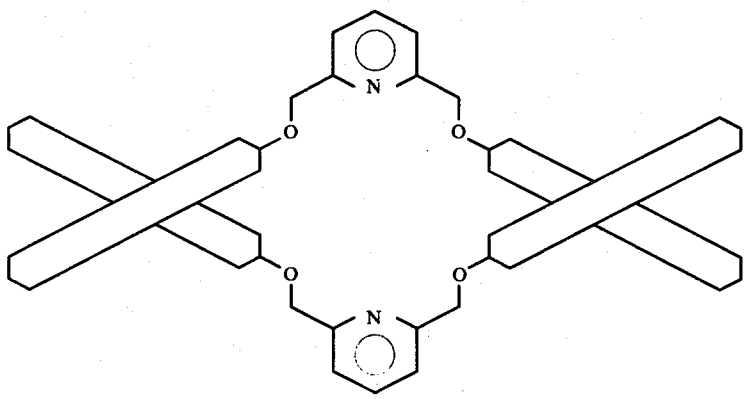

(SS)-19

Procedure 9

Procedure 9 records the preparation of (SS)-19. To a solution of 14.3 g. of optically pure (S)-1,1-binaphthyl [*J. Amer. Chem. Soc.*, 95, 2692 (1973)] in tetrahydrofuran (500 ml.) was added 12.3 g. of potassium tert-butoxide in one portion, which was washed in with 350 ml. of tetrahydrofuran. The solution became a slurry during 15 minutes of stirring at 25°. A solution of 8.8 g. of 5 was added in one portion, and the reaction mixture was stirred and heated under reflux in a nitrogen atmosphere for 96 hours, and cooled. The brown solution was decanted from the precipitated semi solid mass and evaporated to 150 ml. The solution deposited (crystalline) 3.7 g. of (SS)-19·2($CH_2$)$_4$O (pmr integration). The filtrate from the crystals was mixed with the original residue, the solvent was evaporated, and the residue was partitioned between water and dichloromethane. The organic layer was evaporated, and the residue was dissolved in 150 ml. of tetrahydrofuran. The crystals of solvate of (SS)-19 that separated were collected to give 3.6 g. of material, which was combined with the original material to give 7.2 g. (31%), m.p. (dried at 25° for 48 hours) 295–298° (dec.), mass spectrum (70 eV) gave molecular ion for (SS)-19 at m/e = 778, $[\alpha]_{589}^{25}$ −250°, $[\alpha]_{578}^{25}$ −264°, $[\alpha]_{546}^{25}$ −319°, $[E]_{436}^{25}$ −772° (c 1.1, $CHCl_3$, corrected for solvate), pmr (100 MHz, $CDCl_3$), δ: 6.8–7.9 (m, naphthalene ArH and pyridine-γ-H, 26H); 6.32 and 6.40 (s,s, pyridine-β-H, 4H); 4.82 (s, $ArCH_2$, 8H); 3.66 and 1.76 (m, m, tetrahydrofuran, 16H).

Anal. Calcd for $C_{54}H_{38}N_2O_4 \cdot C_8H_{16}O_2$: C, 80.69; H, 5.86. Found: C, 80.50; H, 6.06.

The solvate was dissolved in dichloromethane, the solution was evaporated, and the oil was dried to a foam at 120° and 0.1 mm, pmr spectrum (100 MHz in $CDCl_3$), δ: 4.82 (s, $ArCH_2$, 8H); 6.32–7.9 (m, ArH, 30).

Anal. Calcd for $C_{54}H_{38}N_2O_4$: C, 83.27; H, 4.92. Found: C, 83.20; H, 5.03.

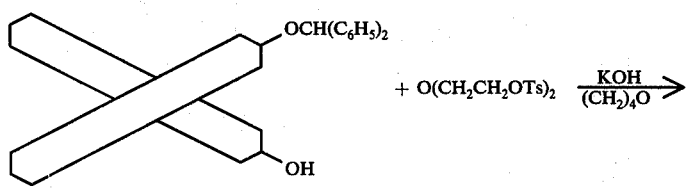

(S)-20

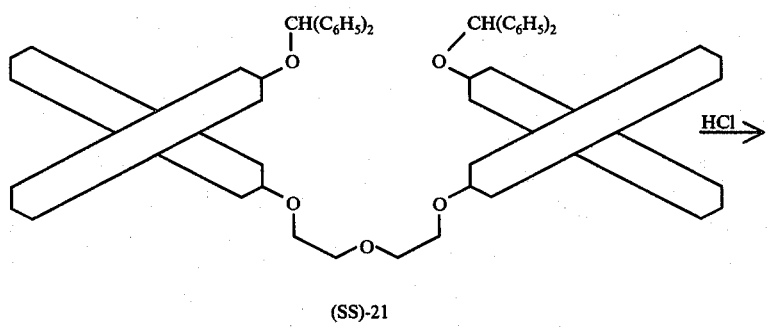

(SS)-21

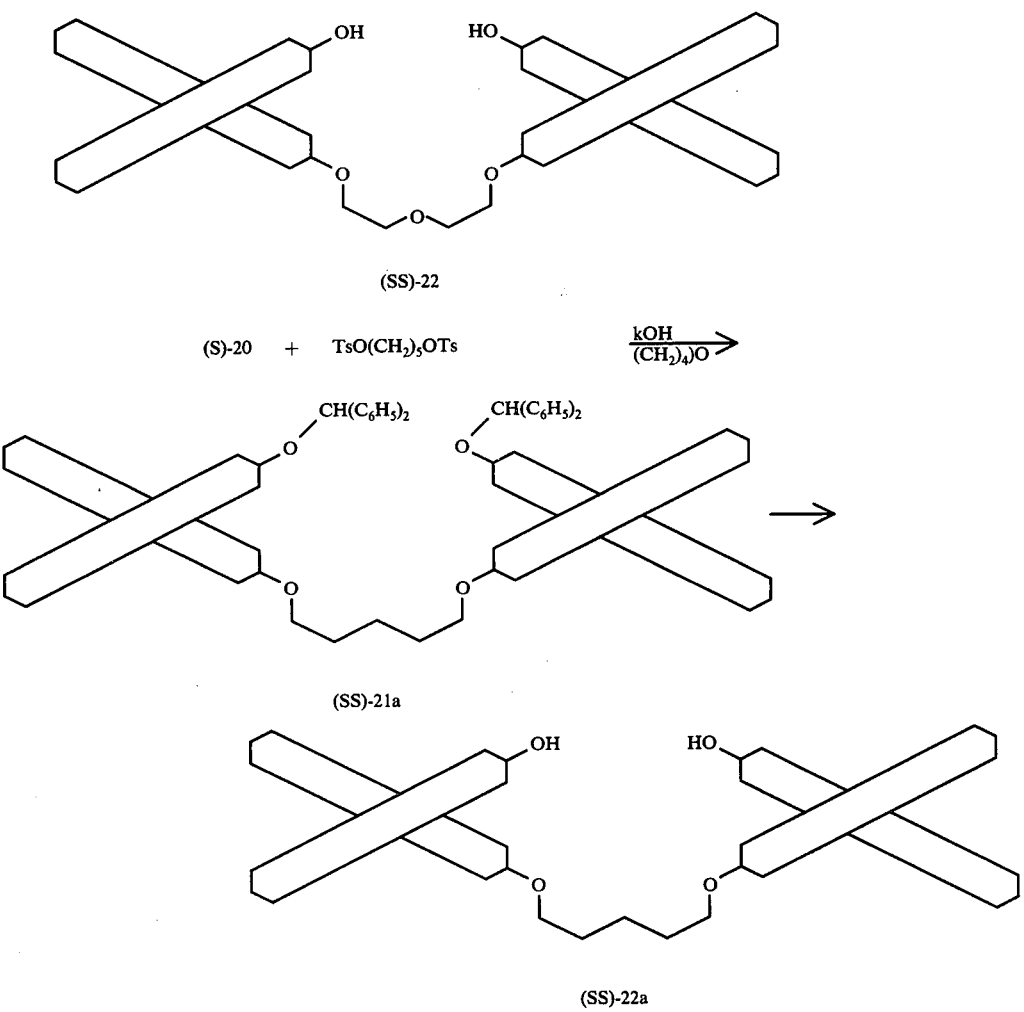

(SS)-22

(S)-20 + TsO(CH₂)₅OTs $\xrightarrow[\text{(CH}_2)_4\text{)O}]{\text{kOH}}$ (SS)-21a (SS)-22a

Procedure 10

Procedure 10 records the preparation of (SS)-21, (SS)-21a, (SS)-22 and (SS)-22a. Optically pure (S)-20, 9.05 g., 4.14 g. of diethyleneglycol ditosylate and 1.45 g. of potassium hydroxide in 5 ml of water was mixed with 200 ml. of tetrahydrofuran, and the solution was refluxed for 36 hours. The solution was cooled slightly, and 2 ml. of 50% aqueous potassium hydroxide and 2 g. of diethyleneglycol ditosylate were added, and refluxing was resumed for 12 hours. The mixture was cooled, filtered, and the filtrate was evaporated under vacuum. The residue was chromatographed on alumina, with dichloromethane in pentane as eluting agent. The product, (SS)-21, was eluted in two successive one liter fractions (40% dichloromethane by volume), 7.15 g. (73%), as a white foam. The compound's mass spectrum (70 eV) gave a molecular ion at m/e = 974, $[\alpha]_{578}^{25}$ −3.04, $[\alpha]_{546}^{25}$ −5.18°, $[\alpha]_{436}^{25}$ −30.25°(c 1, CHCl₃), and a pmr spectrum consistent with the assigned structure.

Anal. Calcd for C₇₀H₅₄O₅: C, 86.21; H, 5.58. Found: C, 86.08; H, 5.69.

A solution of 4.35 g. of (SS)-21a in 50 ml. dichloromethane, 50 ml. of methanol and 5 ml. of concentrated hydrochloric acid was stirred 24 hours at 25°. The solution was shaken with 200 ml. of dichloromethane and 200 ml. of ice water, and the organic phase was washed with water, dried and evaporated. The mixture of (SS)-22 and benzhydryl methyl ether produced was used directly in the next step (preparation of (SS)-23, see Procedure 11).

Compound (SS)-21a was prepared by the same procedure used to obtain (SS)-21 except that pentamethyleneglycol ditosylate was substituted for diethyleneglycol ditosylate. Compound (SS)-21a, a white foam, was obtained in 55% yield, gave a mass spectrum (70 eV) molecular ion at m/e = 972, $[\alpha]_{578}^{25}$ −20.8°, $[\alpha]_{546}^{25}$ −25.5°, $[\alpha]_{436}^{25}$ −69.3°(c 0.8, CHCl₃), and a pmr spectrum consistent with its assigned structure.

Anal. Calcd for C₇₁H₅₆O₄: C, 87.62; H, 5.80. Found: C, 87.32; H, 5.58.

Acid hydrolysis of (SS)-21a to give (SS)-22a mixed with benzhydryl methyl ether was carried out by the same procedure used to produce (SS)-22 from (SS)-21. The mixture was used directly in the preparation of (SS)-23a.

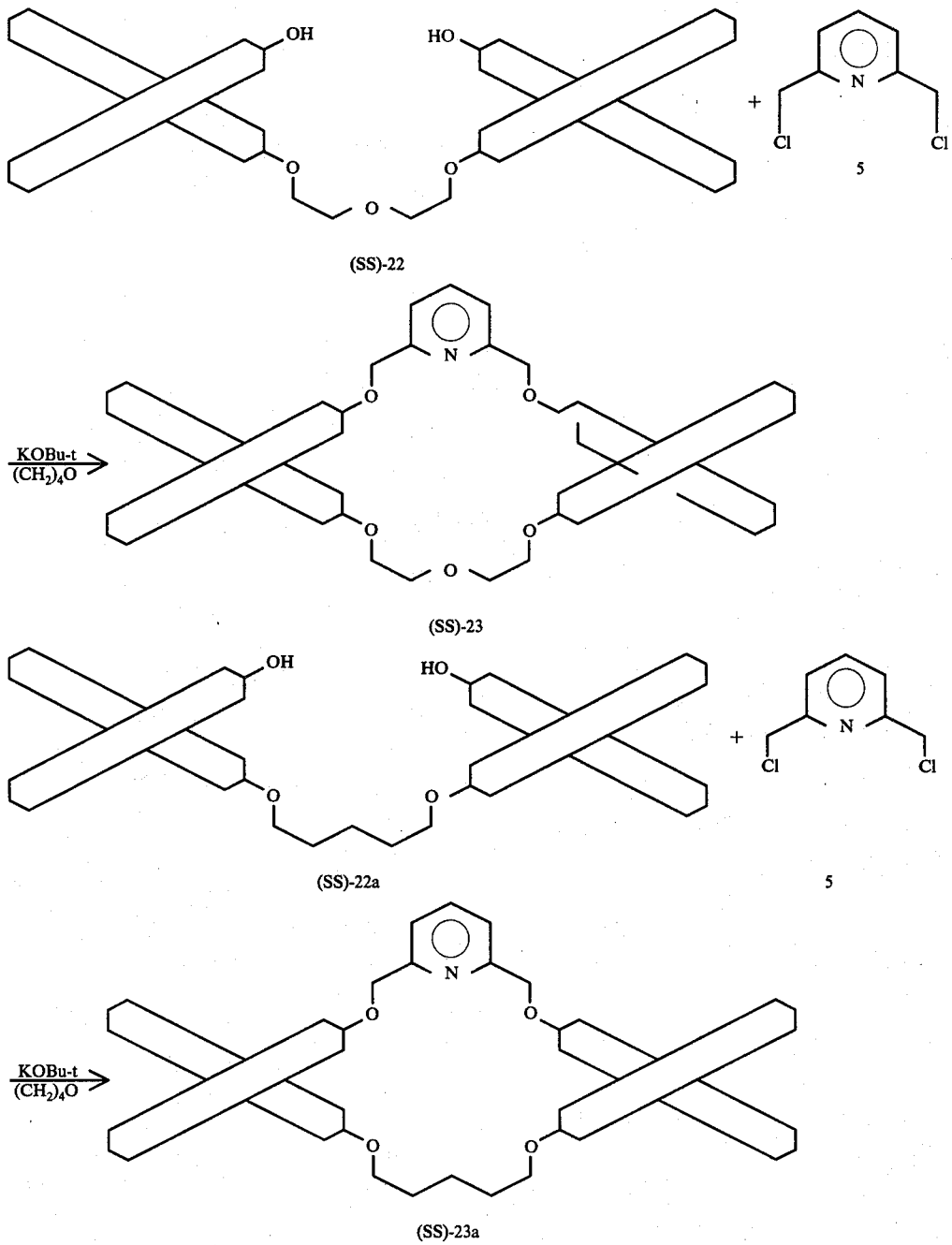

Procedure 11

Procedure 11 reports the preparation of (SS)-23 and (SS)-23a. The mixture of benzhydryl methyl ether and (SS)-22 produced from 7.65 g. of (SS)-21 was dissolved in 100 ml. of tetrahydrofuran, and mixed with 1.93 g. of potassium tert-butoxide, 1.4 g. of 5 and an additional 100 ml. of tetrahydrofuran. The solution was refluxed for 24 hours, the mixture was cooled, filtered, and the filtrate was evaporated. The residue was chromatographed on 250 g. of alumina. Elution of the column with one liter of 1:9 dichloromethane-pentane removed the benzhydryl methyl ether. The product, (SS)-23, was eluted with 2:3 dichloromethanepentane, weight 2.54 g. (44%), after drying at 110° for 20 hours (foam), $[\alpha]_{578}^{25}$ −242°, $[\alpha]_{546}^{25}$ −288°, $[\alpha]_{436}^{25}$ −665° (c 0.7, CHCl$_3$), pmr spectrum (100 MHz in CDCl$_3$), δ: 7.0–7.9 (m, naphthalene ArH and pyridine—γ—H, 25H); 6.68, 6.76 (s, s, pyridine-β-H, 2H); 4.89 (s, ArCH$_2$, 4H); 3.62 (pseudo-t, ArOCH$_2$, 4H); 2.9 (m, CH$_2$OCH$_2$, 4H).

Anal. Calcd for C$_{51}$H$_{39}$N$_5$: C, 82.12; H, 5.27. Found: C, 82.33; H, 5.43.

Cycle (SS)-23a was similarly prepared. A solution of a mixture of (SS)-22a and benzhydryl methyl ether prepared by methanolysis of 4.5 g. of optically pure (SS)-21a in 200 ml. of tetrahydrofuran was mixed with 2.02 g. of 5 and 1.14 g. of potassium tert-butoxide. The resulting mixture was refluxed for 48 hours, and the product isolated by extraction and chromatography, weight 1.5 g. (29%), white foam after drying at 145° and 0.01 mm, mass spectrum (70 eV) molecular ion at m/e =743, $[\alpha]_{589}^{25}$ −240°, $[\alpha]_{578}^{25}$ −250°, $[\alpha]_{546}^{25}$ −301°,

[α]₄₃₆²⁵ −702° (c 0.5, CHCl₃), pmr spectrum (60 MHz) in CDCl₃, δ: 7.0-7.9 (m, naphthalene ArH, and pyridine ArH-γ, 25H); 6.62, 6.73 (s, s, pyridine ArH-β, 2H); 4.88 (s, ArCH₂, 4H); 3.52 (broad s, ArOCH₂, 4H); 0.8 (broad s, CH₂(CH₂)₃CH₂, 6H).

Anal. Calcd for C₅₂H₄₁NO₄: C, 83.96; H, 5.56. Found: C, 83.98; H, 5.69.

EXAMPLE 2

Preparation of Furan Unit-Containing Host Compounds

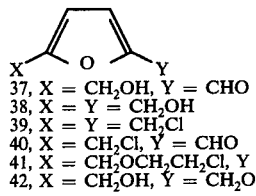

37, X = CH₂OH, Y = CHO
38, X = Y = CH₂OH
39, X = Y = CH₂Cl
40, X = CH₂Cl, Y = CHO
41, X = CH₂OCH₂CH₂Cl, Y = CHO
42, X = CH₂OH, Y = CH₂OCH₂CH₂Cl

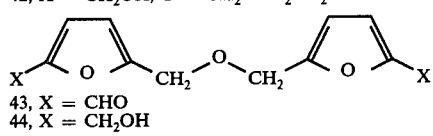

43, X = CHO
44, X = CH₂OH

Procedure 1

Procedure 1 deals with the starting materials for preparation of the furan-containing cycles. Compound 37 was prepared from sucrose [J. Chem. Soc., 667 (1944)]. Reduction of 37 with sodium borohydride gave 38 [J. Chem. Soc., 3917 (1963)]. Dropwise addition with stirring of a solution of 38 in 2,6-lutidine to a stirred solution of thionyl chloride in ethyl acetate at −20° gave a frozen solid that was warmed to 75° and stirred for 1 hour. Water and pentane were added, and the unstable 39 [British Pat. No. 911,221; Chem. Abstr., 58, 9027f (1963)] was isolated at low temperature without distillation, and was used immediately. Compound 40 was also prepared from sucrose [J. Chem. Soc., 667 (1944); Can. J. Chem., 37, 1056 (1959)]. Water was azeotropically distilled (4 hours) from 37 in toluene-containing 0.2% p-toluenesulfonic acid to give after chromatographic purification, 43 [British Pat. No. 887,360; Chem. Abstr., 57, 2196b (1962)].

New compound 41 was prepared as follows. Chloroaldehyde 40, 13.9 g., was added to 210 ml. of 2-chloroethanol containing 28 g. of barium carbonate. The mixture was stirred at 70° for 16 hours. The solution was cooled, filtered, and 200 ml. of dichloromethane was added. The mixture was washed with water three times. The organic layer was dried, the solvent was evaporated followed by the excess 2-chloroethanol (under vacuum), and the residue was distilled at 0.4 mm, b.p. 117°, weight 15.1 g. (87%), mass spectrum (70 eV) molecular ion at m/e = 188, pmr (100 MHz in CDCl₃), δ: 3.72 (m, OCH₂CH₂Cl, 4H); 4.62 (s, ArCH₂, 2H); 6.57 (d, J = 3.5 Hz, 3-ArH, 1H); 7.22 (d, J = 3.5 Hz, 4-ArH, 1H); 9.62 (s, CHO, 1H).

Anal. Calcd for C₈H₉ClO₃: C, 50.95; H, 4.81. Found: C, 50.90; H, 4.81.

New compound 42 was prepared as follows. Chloroaldehyde 41, (8.7 g) was dissolved in 300 ml. of absolute ethanol, 1.75 g. of sodium borohydride was added, and the resulting solution was stirred at 25° for 2 days. The solution was acidified with concentrated hydrochloric acid, solid sodium bicarbonate was added immediately; the mixture was filtered, the solvent was evapo-rated from the filtrate, and the residue was distilled to give 8.5 g. (97%) of chloroalcohol 42, b.p. 104°-105° at 0.2 mm, mass spectrum (70 eV) gave a molecular at m/e = 190.

Anal. Calcd for C₈H₁₁ClO₃: C, 50.40; H, 5.80; Cl, 18.59. Found: C, 50.32; H, 5.86; Cl, 18.32.

New compound 44 was prepared as follows. Dialdehyde ether 43, 7.8 g., was dissolved in 230 ml. of absolute ethanol, 2.5 g. of sodium borohydride was added, the mixture was stirred at 25° for 4 hours, and refluxed for 4 hours. The solution was cooled, the mixture was acidified with concentrated hydrochloric acid, solid sodium bicarbonate was immediately added, the mixture was filtered, and the solvent was evaporated from the filtrate. The residue was crystallized from chloroform to give 7.5 g. (98%) of diol 44, m.p. 92°-93°, mass spectrum (70 eV) molecular ion at m/e = 236, pmr (100 MHz, (CD₃)₂CO), δ: 3.0 (s, OH, 2H); 4.42 (s, CH₂OCH₂, 4H); 4.49 (s, CH₂OH, 4H); 6.20 (d, J = 2.9 Hz, 3-Ar-H, 2H); 6.30 (d, J = 2.9 Hz, 4-Ar-H, 2H).

Anal. Calcd for C₁₂H₁₄O₅: C, 60.50; H, 5.92. Found: C, 60.55; H, 6.07.

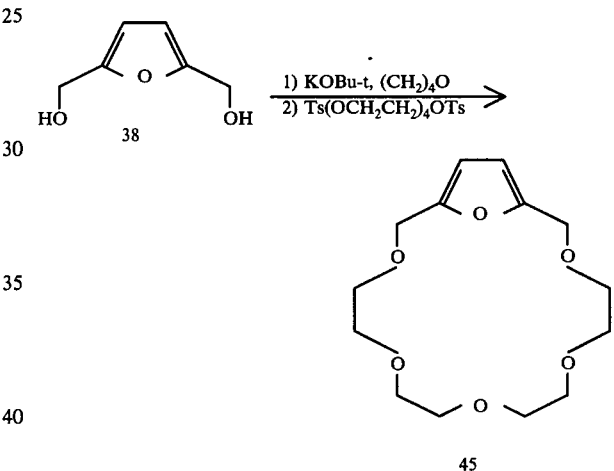

Procedure 2

Procedure 2 records the preparation cycle 45, and exemplified the synthesis of other analogues that contain one furan unit. In a nitrogen atmosphere, 54 g. of tetraethyleneglycol ditosylate in 200 ml. of tetrahydrofuran was added dropwise to one liter of tetrahydrofuran containing 12.5 g. of diol 38 and 24 g. of potassium tert-butoxide. The solution was stirred at 25° for 12 hours, refluxed for 12 hours, cooled, dried and the solvent was evaporated. The residue was chromatographed on 1 Kg of a alumina with dichloromethane-ether (1:1) as eluting agent to give 10 g. (36%) of 45, m.p. ~0°, mass spectrum (70 eV), molecular ion at m/e 286, pmr (100 MHz, CDCl₃), δ: 3.60 (s, OCH₂CH₂O, 16H); 4.46 (s, ArCH₂O, 4H); 6.11 (s, ArH, 2H).

Anal. Calcd for C₁₄H₂₂O₆: C, 58.73; H, 7.74. Found: C, 58.43; H, 7.88.

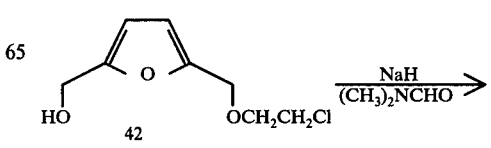

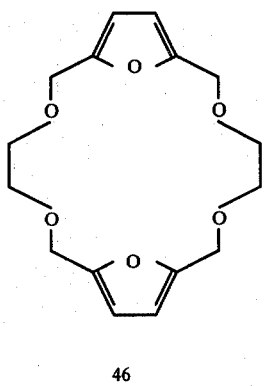

Procedure 3

Procedure 3 records the synthesis of cycle 46, and exemplifies the synthesis of the other analogues that contain two furan units located 180° from one another. In a nitrogen atmosphere, sodium hydride, 0.75 g., was slowly added to 500 ml. of dimethylformamide containing 4 g. of 42. The solution was stirred at room temperature for 2 days, 500 ml. of dichloromethane was added, and the solution was extracted with water to remove the dimethylformamide. The dichloromethane solution was dried, evaporated, and the 4.4 g. of residue was chromatographed on 120 g. of alumina with dichloromethane as eluent to give 1 g. (28%) of vinyl ether derived from 42, followed by 0.40 g. (11%) of cycle 46, m.p. 109°–111°. The compound gave a molecular ion at $m/e = 308$ in its mass spectrum, and a 100 MHz spectrum in CDCl$_3$, δ: 3.57 (s, OCH$_2$CH$_2$O, 8H); 4.44 (s, ArCH$_2$O, 8H); 6.20 (s, ArH, 4H).

Anal. Calcd for C$_{16}$H$_{20}$O$_6$: C, 62.32; H, 6.54. Found: C, 62.15; H, 6.69.

100 ml. of tetrahydrofuran was added dropwise to 200 ml. of tetrahydrofuran containing 3.7 g. of diol 44 and 4.05 g. of potassium tert-butoxide. The mixture was stirred at 25° for 24 hours, more ditosylate (0.66 g.) was added, and the solution was refluxed for 6 hours. The solution was cooled, filtered, and the solvent was evaporated from the filtrate to give 7 g. of residue, which was chromatographed on 300 g. of alumina with dichloromethane as eluting agent. Product, 1.7 g. (35%) of 97 was eluted which was recrystallized from dichloromethane-pentane to give m.p. 69°–70°, mass spectrum (70 eV) molecular ion at $m/e = 308$, pmr spectrum (100 MHz in CDCl$_3$), δ: 3.64 (s, OCH$_2$CH$_2$O, 8H); 4.48 (s, ArCH$_2$, 8H); 6.22 (AB quartet, J$_{AB}$ ~ 3.4 Hz, ArH, 4H).

Anal. Calcd for C$_{12}$H$_{20}$O$_6$: C, 62.32; H, 6.54. Found: C, 62.25; H, 6.36.

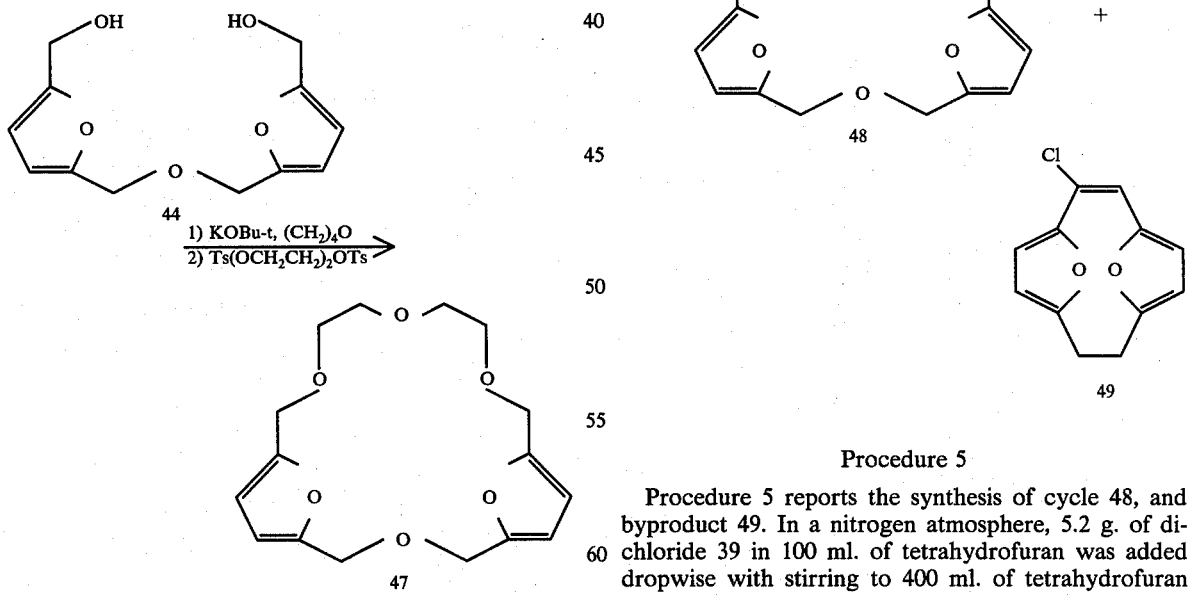

Procedure 4

Procedure 4 reports the synthesis of cycle 47, and exemplifies the synthesis of macrocycles containing two furanyl units separated by a Ch$_2$OCH$_2$ unit. In a nitrogen atmosphere, 6.6 g. of diethyleneglycol ditosylate in

Procedure 5

Procedure 5 reports the synthesis of cycle 48, and byproduct 49. In a nitrogen atmosphere, 5.2 g. of dichloride 39 in 100 ml. of tetrahydrofuran was added dropwise with stirring to 400 ml. of tetrahydrofuran containing 7.5 g. of diol 44 and 7.8 g. of potassium tert-butoxide. The solution gradually turned dark red. The mixture was stirred at 25° for 2 days, filtered, and the solvent was evaporated from the filtrate to give 10.7 g. of dark red residue. This material was chromatographed on 230 g. of silica gel with dichloromethane to give 1.2 g. of a dark red oil, 5.2 g. (70%) of diol 44, and 1 g. of solid which was recrystallized from dichloromethane-pentane to give 48 (10% based on starting diol, or 32% based on consumed diol), m.p. 124°–126°, mass spectrum (70 eV) molecular ion at m/e =330, pmr spectrum (100 MHz in CDCl₃), δ: 4.47 (s, CH₂, 12H); 6.27 (s, ArH, 6H).

Anal. Calcd for $C_{18}H_{18}O_6$: C, 65.45; H, 5.49. Found: C, 65.56; H, 5.65.

The red fraction was purified by gel permeation chromatography (Bio-Rad SX-8 packing, ⅜ inch by 18 foot column, tetrahydrofuran as solvent, 3ml. per min. flow rate, pressure 350 psi, 2 ml. injection with 0.1 to 0.5 g. per injection). Compound 49 was isolated as a slightly yellow liquid, weight 1.0 g. (29%), mass spectrum (70 eV) molecular ion m/e = 220, pmr spectrum at 30° (100 MHz, CDCl₃), 2.0–3.5 (very broad s, CH₂, 4H); 6.14 and 6.17 (two overlapping d, $J_{3,2} = J_{6,7} = 3.4$ Hz, $H^3$ and $H^6$, 2H); 6.55 (d of d, $J_{2,3} = 3.4$ Hz, $J_{2,1} = 0.7$ Hz, $H^2$, 1H); 6.77 (d, $J_{1,2} = 0.7$ Hz, $J_{1,2} = 0.7$ Hz, $H^1$, 1H); 6.88 (d, $J_{7,6} = 3.4$ Hz, $H^7$, 1H). The broad singlet became a sharp singlet at δ 2.60 (coalescence temperature about 30°), and separated into an AB quartet below 0°, $v_A = 2.03$, $v_B = 3.23$, $J_{AB} = 10$ Hz. Apparently the members of each pair of vicinal protons have the same chemical shifts, but the geminal protons do not for conformational reasons. The ring-system conformations inhibit equilibration of the geminal protons below 30°. Compound 49 undoubtedly arises from ring closure of a diradical formed by head-to-head dimerization of a triene (formed from 39 by base-catalyzed elimination) followed by elimination of one mole of hydrochloric acid from the product [J. Amer. Chem. Soc., 82, 1428 (1960); ibid., 88, 515 (1966)].

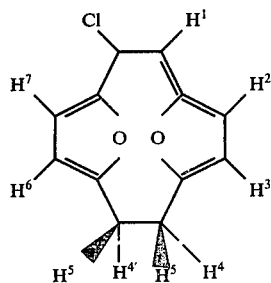

EXAMPLE 3

Preparation of Tetrahydrofuran Unit-Containing Host Compounds.

Many naturally occurring antibiotics, generally isolated from various Streptomyces strains, uncouple oxidative phosphorylation in rat liver mitochondria, and have been shown to affect ion permeability through both natural and synthetic membranes [Science, 178, 24 (1972); Helv. Chim. Acta, 54, 286 (1971); "Antibiotics, I", D. Gottlieb and P. D. Shaw, ed., Springer-Verlag, New York, 1967, p. 649; J. Membrane Biol., 1, 294 (1969)]. Many of these antibiotics contain one or several tetrahydrofuran units (e.g. the actins, grisorixin and nigericin), and are either multiheteromacrocycles, or form cycles through hydrogen bonding. This example indicates how the furan-containing units of the multiheteromacrocycles of Example 2 can be converted to the tetrahydrofuran-containing multiheteromacrocycles, which Example 8 indicates are excellent complexing agents.

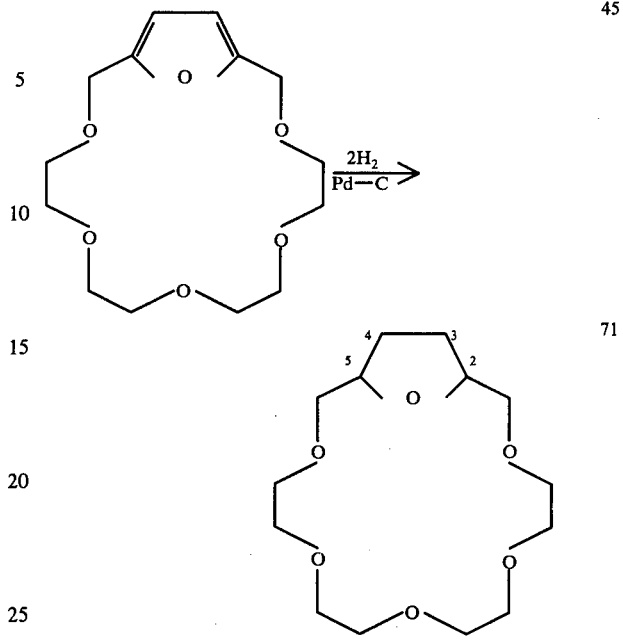

Procedure 1

Procedure 1 reports the reduction of 45 to 71, and exemplifies a general procedure by which all furan units of multiheteromacrocycles can be reduced to their corresponding tetrahydrofuran-containing multiheteromacrocycles. A mixture of 200 mg. of 45, 100 ml. of absolute ethanol and 30 mg. of 10% palladium on charcoal was stirred for 1 hour at 25° in an atmosphere of hydrogen. The hydrogen uptake had stopped. The mixture was filtered, the solvent evaporated, and the 200 mg. of residue was submitted to preparative glc chromatography [5% SE-30 on Fluoropak (>20 mesh), 6 g. per foot, 6 foot column at 260°, retention time 12 minutes]. The product, 71, emerged as a single band, mass spectrum (70 eV) molecular ion m/e = 290, pmr (100 MHz, CDCl₃, δ: 1.90 (m, $H^3$ and $H^4$, 4H, collapses to a slightly broadened singlet upon irradiating at 4.1); 3.60 (m, CH—CH₂—O, 4H), 3.68 (s, $OCH_2CH_2O$, 16H); 4.1 (m, $H^2$ and $H^5$, 2H, collapses to a triplet, J = 4.5Hz, upon irradiation at 1.90).

Anal. Calcd for $C_{14}H_{26}O_6$: C, 57.91; H, 9.03. Found: C, 58.00; H, 9.16.

When complexed with Eu (PPM)₃, the methine region of the pmr spectrum of 71 splits into two broad overlapping peaks, which fact indicates the compound to be a mixture of cis-trans isomers.

EXAMPLE 4

Preparation of Diels-Alder Adducts of Furan-Containing Host Compounds

The Diels-Alder adducts of the furan-containing host compounds are themselves strong complexing agents, and also serve as highly versatile starting materials for preparation of a large number of arm containing host compounds. This example indicates how the furan-containing units of the multiheteromacrocycles of Example 3 can be converted to their Diels-Alder adducts.

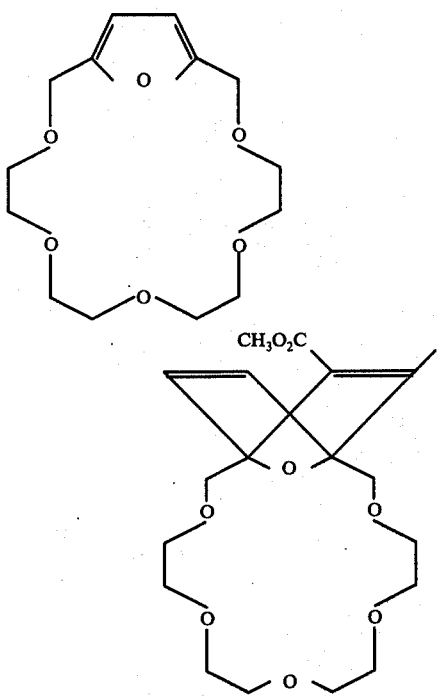

Procedure 1

Procedure 1 reports the addition of dimethyl acetylene dicarboxylic ester to 45 to give 89, and exemplifies a general procedure by which furan units of multiheteromacrocycles can be converted to the product of their Diels-Alder addition reactions. A solution of 1.0 g. of 45, 3.0 g. of dimethyl acetylenedicarboxylic ester in 20 ml. of toluene was heated to 110° for 15 hours. The solvent was evaporated, and the residue was subjected to gel permeation chromatography with tetrahydrofuran as solvent to give 89 as an oil, 1.1 g. (75%), mass spectrum (70 eV) molecular ion at $m/e = 428$, pmr (100 MHz in $CDCl_3$), $\delta$: 3.58 (s, $OCH_2CH_2O$, 16H); 3.72 (s, $CH_3$, 6H); 4.17 (AB quartet, $J_{AB} \sim 11$Hz, $\Delta\delta \sim 7$Hz, $C—CH_2—O$, 4H), 6.94 (s, CH=CH, 2H).

Anal. Calcd for $C_{20}H_{28}O_{10}$: C, 56.07; H, 6.59. Found: C, 56.00; H, 6.42.

The temperature dependent pmr spectrum of 89 was demonstrated by these data.

| Solvent | Temp °C | Δδ (separation of inner two lines of AB quartet) |
|---|---|---|
| $C_6H_5Cl$ | 25 | 14 Hz |
| $C_6H_5Cl$ | 60 | 10 HZ |
| $C_6H_5Cl$ | 80 | 8 Hz |
| $C_6H_5Cl$ | 127 | 5 Hz |
| o-$C_6H_4Cl_2$ | 25 | 13 Hz |
| o-$C_6H_4Cl_2$ | 116 | 5 Hz |
| o-$C_6H_4Cl_2$ | 136 | 4 Hz |
| o-$C_6H_4Cl_2$ | 163 | 3 Hz |

EXAMPLE 5

Preparation of m-Xylyl Unit-Containing Host Compounds

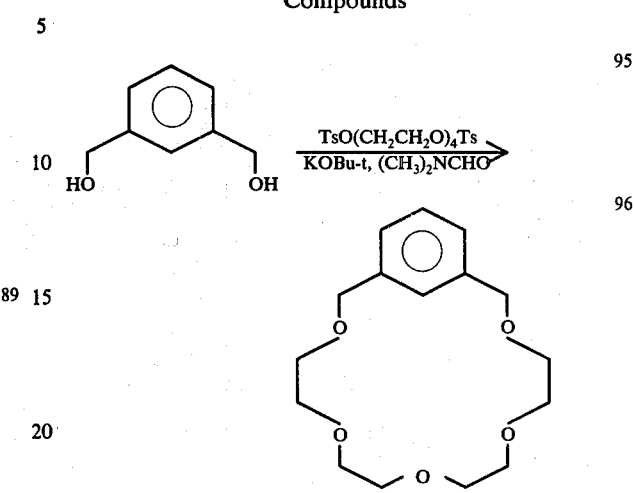

Procedure 1

Procedure 1 reports the preparation of cycle 96. To a solution of 5.52 g. of diol 95 [Can. J. Research, 23b, 106 (1945)] in 400 ml. of dry dimethylformamide was added 9.43 g. of potassium tert-butoxide, and the solution was stirred at 25° for 1 hour. A solution of 20.1 g. of tetraethyleneglycol ditosylate in 100 ml. of dry dimethylformamide was added, and the solution was stirred at 25° for 3 days. The solvent was evaporated under vacuum, and the residue was shaken with a mixture of 3% hydrochloric acid and dichloromethane. The organic layer was washed with water, dried, and the solvent was evaporated. The residual oil was chromatographed on silica gel. Elution of the column with ether gave 96, 3.6 g. (30%) as an oil that crystallized, and was recrystallized from pentane, m.p. 44°–46°, mass spectrum (70 eV) molecular ion at $m/e = 296$, pmr spectrum (60 MHz, $CDCl_3$), $\delta$: ~3.73 (d, $OCH_2CH_2O$, 16H); 4.65 (s, $ArCH_2O$, 4H); 7.1–7.3 (m, ArH, 3H); 7.7 (broad s, ArH, 1H).

Anal. Calcd for $C_{16}H_{24}O_5$: C, 64.84; H, 8.16. Found: C, 65.00; H, 8.06.

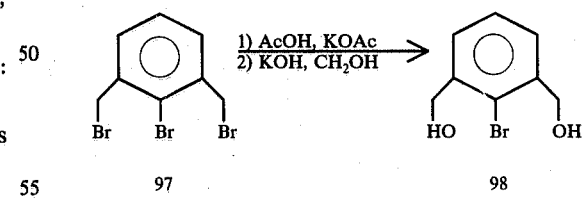

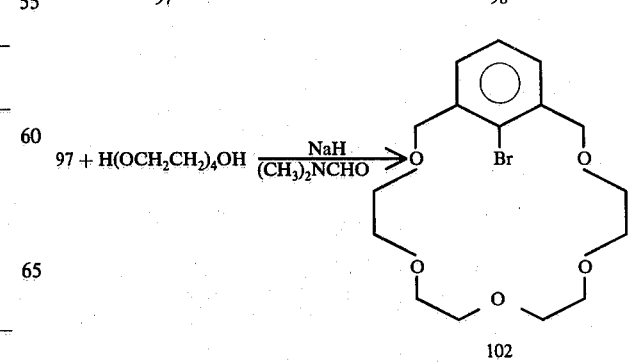

-continued

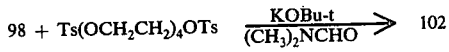

Procedure 2

Procedure 2 records two preparations of cycle 102. In the first, sodium hydride, 1.62 g., was added to a solution of 2.91 g. of tetraethyleneglycol in 150 ml. of dry dimethylformamide at 25°. After 45 minutes of stirring, tribromide 97 [*Chem. Ber.*, 102, 1734 (1969)], 5.14 g. in 15 ml. of dry dimethylformamide was added, and the resulting mixture was stirred at 25° for 4 days. The reaction mixture was evaporated under vacuum to dryness, and the residue was shaken with a mixture of 3% aqueous hydrochloric acid and dichloromethane. The organic layer was washed with water, dried, evaporated and chromatographed on silica gel. Elution of the column with benzene gave 350 mg. (7%) of 102 as a colorless liquid, mass spectrum (70 eV) molecular ions at $m/e = 374$ and 376, pmr spectrum (60 MHz in $CDCl_3$), $\delta$: 3.6 and 3.5 (two peaks, $OCH_2CH_2O$, 16H); 4.67 (s, $ArCH_2O$, 4H); 7.25 (m, ArH, 3H).

Anal. Calcd for $C_{16}H_{23}O_5Br$: C, 51.21; H, 6.18. Found: C, 51.22; H, 6.30.

Tribromide 97 was converted to its diacetate by refluxing 97 in a potassium acetate solution (0.5 M) in glacial acetic acid for 24 hours. The solvent was distilled through a short column, and the residue was dissolved in dichloromethane. The solution was washed with water, dried, and the solvent was evaporated. The residual oil was refluxed in 90% methanol-potassium hydroxide (1M) for 24 hours, the solvent was evaporated, and the residual oil was dissolved in dichloromethane to give a solution that was washed with water, dried and evaporated. The residual oil, 98 (94%) was used in the next step without further purification or characterization.

Cycle 102 was prepared from 98 as follows. To a solution of 6.08 g. of diol 98 and 14.1 g. of tetraethyleneglycol ditosylate in 250 ml. of dry dimethylformamide was added 6.0 g. of potassium tert-butoxide, and the solution was stirred for 4 days at 25°. Cycle 102 was isolated as in the above preparation, weight 750 mg. (7%). Its properties were identical to those of the sample prepared directly from 97.

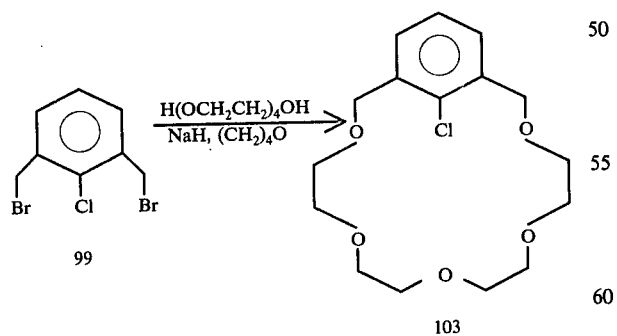

Procedure 3

Procedure 3 records the synthesis of 103 from 99. Tetraethyleneglycol, 5.82 g., was dissolved in 500 ml. of dry tetrahydrofuran, and 1.8 g. of sodium hydride was added. The mixture was stirred for 1 hour, and to the stirred reaction mixture at 25° was added dropwise over a 3 hour period, 8.94 g. of 99 [Chem. Ber., 102, 1784 (1969)] dissolved in 500 ml. of dry tetrahydrofuran. The mixture was stirred an additional 12 hours at 25°, the solvent was evaporated, and the residue was shaken with dichloromethane and dilute hydrochloric acid. The organic layer was washed with water, dried, evaporated, and chromatographed on 500 g. of alumina. Dichloromethane eluted 103 which was obtained as an oil, 5.3 g. (53%). An analytical sample (oil) was purified by preparative glpc on a 0.25 inch by 6 foot, 5% SE-30 on Fluropak column at 285°, 60 ml./min. flow rate, mass spectrum (70 eV) molecular ion at $m/e = 330$, pmr spectrum (60 MHz, $CDCl_3$), $\delta$: 3.4–3.6 (m, $OCH_2CH_2O$, 16H): 4.6 (s, $ArCH_2$, 4H), 7.0–7.3 (m, ArH, 3H).

Anal. Calcd for $C_{16}H_{23}ClO_5$: C, 58.09; H, 7.01. Found: C, 57.89; H, 7.06.

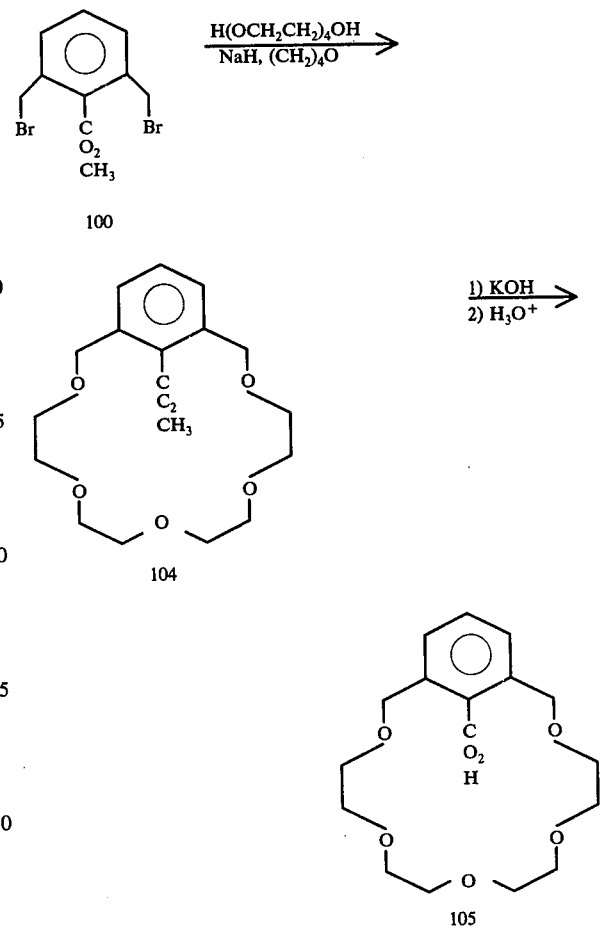

Procedure 4

Procedure 4 records the syntheses of 100, 104 and 105. To a stirred and refluxing mixture of 1.5 g. of sodium hydride in 500 ml. of dry tetrahydrofuran was added dropwise over a period of 3 hours at 25° a solution of 4.85 g. of tetraethyleneglycol and 8.05 g. of 100 (see Procedure 5 of this section) in 500 ml. of dry tetrahydrofuran. The resulting mixture was stirred at 25° for 12 hours, the solvent was evaporated, and the residue was shaken with a mixture of dichloromethane and dilute hydrochloric acid. The organic layer was washed with water, dried and evaporated, and the residue was chromatographed on 500 g. of silica gel. Product 104 was eluted with dichloromethane-acetone mixtures, and was chromatographed on a gel permeation chromatograph column Bio-Beads SX-8 packing, ⅜ inch by 18 foot column) with tetrahydrofuran as eluting agent (132 ml. retention volume) to give 4.43 g. (50%) of 104 as a hygroscopic oil, mass spectrum (70 eV) molecular ion at $m/e = 354$, pmr spectrum (60 MHz, $CDCl_3$), δ: 3.47 and 3.54 (two peaks, $OCH_2CH_2O$, 16H); 3.9 (s, $CH_3O$, 3H); 4.6 (s, $ArCH_2O$, 4H); 7.3 (s, ArH, 3H). A sample of 104 was submitted to preparative glpc (column 0.25 inch by 6 foot, 15% SE-30 on 60/80 firebrick, 285°, 50 ml./min., 15 minutes retention time).

Anal. Calcd for $C_{18}H_{26}O_7$: C, 61.00; H, 7.39. Found: C, 60.81; H, 7.47.

Ester 104 was hydrolyzed to 105 as follows. A mixture of 0.200 g. of 104 and 2 g. of sodium hydroxide in 50 ml. of 95% ethanol was refluxed for 20 hours. The solvent was evaporated, and the residue was shaken with a mixture of water and chloroform. The aqueous phase was washed with chloroform, acidified with hydrochloric acid, extracted with chloroform, and the chloroform solution was dried and evaporated to give 0.190 g. (~100%) of 104, m.p. 88°–96°, which was molecularly distilled at 180° and 20μ to give 104, m.p. 97°–100°. Recrystallization of this material from dichloromethane-pentane gave 104, m.p. 100°–101°, mass spectrum (70 eV) molecular ion at $m/e = 340$, pmr spectrum (60 MHz, $CDCl_3$), δ: 3.9–4.0 (two peaks, $OCH_2CH_2O$ and $CO_2H$, 17H); 4.5 (s, $ArCH_2O$, 4H); 7.0 (s, ArH, 3H).

Anal. Calcd for $C_{17}H_{24}O_7$: C, 59.99; H, 7.11. Found: C, 60.03; H, 7.08.

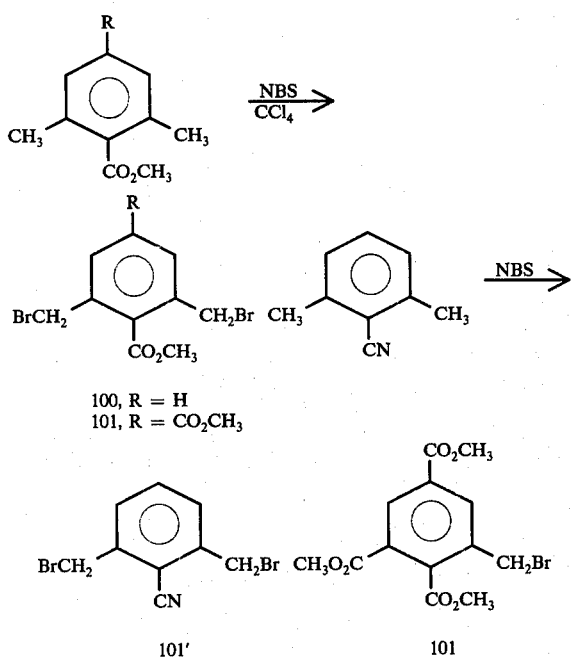

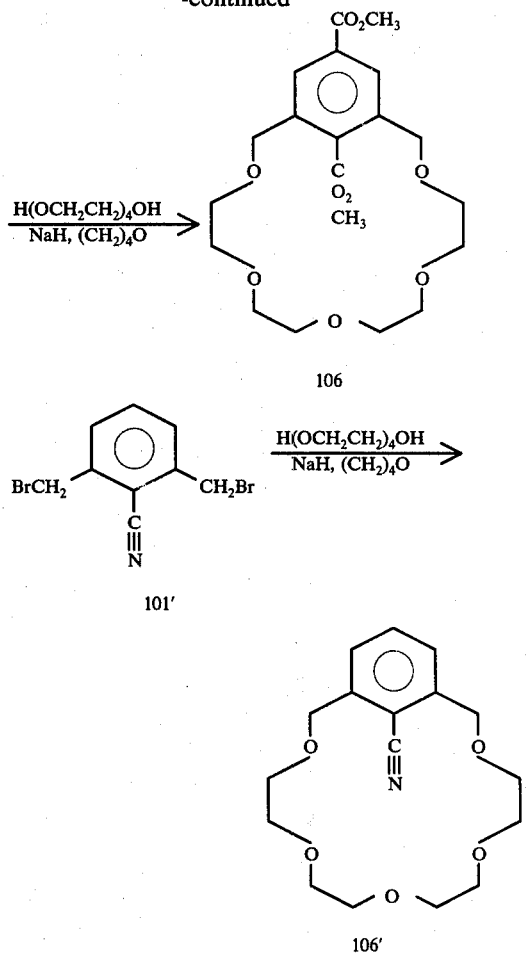

Procedure 5

Procedure 5 reports the preparations of 100, 101 and 101', and the conversion of 101 to 106, and of 101' to 106'. The preparations of 100, 101 and 101' were similar, and are described together. The appropriate substituted m-xylene [J. Amer. Chem. Soc., 76, 787 (1954); Chem. Ber., 27, 3741 (1894); J. Amer. Chem. Soc., 62, 2091 (1940)] was dissolved in carbon tetrachloride dried over calcium hydride, and 2.2 equivalent of N-bromosuccinimide (NBS) and a trace of dibenzoyl peroxide were added. The mixture was warmed at reflux with stirring for 12 hours in an apparatus fitted with a drying tower. The mixture was filtered. The solvent was evaporated from the organic phase, and the product crystallized. In the preparation of 100, the product was recrystallized from cyclohexane to give 100, m.p. 77°–79°, (46% yield) mass spectrum (70 eV) molecular ion at $m/e = 320$, pmr spectrum as expected.

Anal. Calcd for $C_{10}H_{10}Br_2O_2$: C, 37.30; H, 3.13. Found: C, 37.16; H, 3.23.

In the preparation of 101, the product was recrystallized from cyclohexane and gave a 35% yield, m.p. 123°–125°, mass spectrum (70 eV) gave a molecular ion at $m/e = 378$, pmr spectrum as expected.

Anal. Calcd for $C_{12}H_{12}Br_2O_4$: C, 37.92; H, 3.18. Found: C, 37.97; H, 3.20.

In the preparation of 101', the product was obtained as a mixture with its mono and tribromo analogues, and was used in the conversion to 106' without purification.

Compound 101' has been prepared previously [*Chem. Ber.*, 105, 2955 (1972)].

Cycle 106 was prepared as follows. To a stirred and refluxing mixture of 0.51 g. of sodium hydride in 500 ml. dry tetrahydrofuran was added dropwise over a period of 3 hours at 25° a solution of 1.36 g. of tetraethyleneglycol and 2.65 g. of dibromide 101 dissolved in 500 ml. of dry tetrahydrofuran. The mixture was stirred at 25° for 12 hours, the solvent was evaporated, and the residue was shaken with a mixture of dilute hydrochloric acid and dichloromethane. The organic layer was washed with water, dried, evaporated, and the residue was chromatographed on 200 g. of silica gel. Dichloromethane-acetone eluted crude 106, which was chromatographed on a gel permeation chromatograph column (Bio-Beads SX-8 packing, ⅜ inch by 18 foot column) with tetrahydrofuran as solvent, retention volume, 126 ml. The product crystallized to give 0.95 g. (33%) of 106, which was recrystallized from dichloromethane pentane to give m.p. 78°-80°, mass spectrum (70 eV) molecular ion at $m/e$ = 412, pmr spectrum (60 MHz, CDCl$_3$), δ: 3.5, 3.6 (two peaks, OCH$_2$CH$_2$O, 16H); 3.9 ($s$, CH$_3$O, 6H); 4.6 ($s$, ArCH$_2$, 4H); 7.9 ($s$, ArH, 2H).

Anal. Calcd for C$_{20}$H$_{28}$O$_9$: C, 58.24; H, 6.84. Found: C, 58.26; H, 6.85.

Cycle 106' was prepared from 101' by the same procedure used in the preparation of 103 from 99. The product from the reaction was chromatographed on alumina (dichloromethane-benzene-ethanol elution), then on silica gel (dichloromethane-acetone elution), and on Bio Beads SX-8 (gel permeation) with tetrahydrofuran (132 ml. retention volume, column ⅜ inch by 18 feet). The product was an oil (10%), mass spectrum (70 eV) molecular ion at $m/e$ = 321, ir spectrum (neat) 2220 cm$^{-1}$, pmr spectrum (60 MHz, CDCl$_3$), δ: 3.5-3.6 (two peaks, OCH$_2$CH$_2$O, 16H); 4.7 ($s$, ArCH$_2$, 4H); 7.4 ($s$, ArH, 3H). The compound was subjected to glpc (0.25 inch by 6 foot, 15% SE-30 on 60/80 firebrick, 280°, 50 ml./min., 13 minute retention time.

Anal. Calcd for C$_{17}$H$_{23}$NO$_5$: C, 63.54; H, 7.21. Found: C, 63.43; H, 7.40.

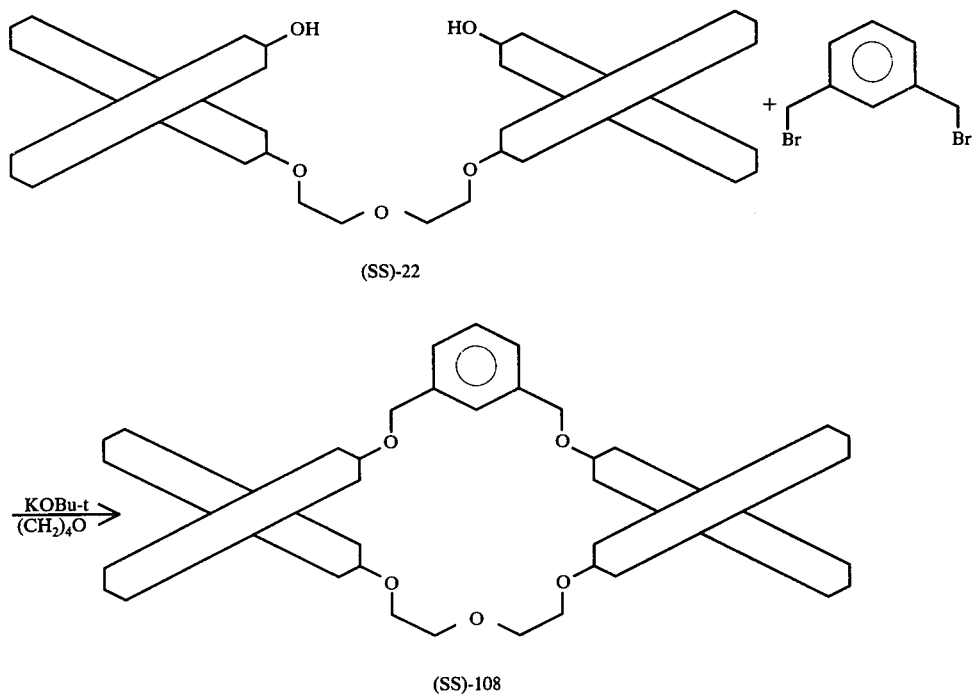

Procedure 6

Procedure 6 reports the preparation of (SS)-108 from (SS)-22 [Example 1, Procedure 10] from m-xylyl dibromide. To a solution of optically pure (SS)-22, 6.0 g., and 2.30 g. of potassium tert-butoxide in tetrahydrofuran (200 ml.) was added 2.47 g. of m-xylyl dibromide. The solution was refluxed for 69 hours, filtered to remove salts, and the filtrate was evaporated under vacuum. The residue was dissolved in dichloromethane, and that solution was washed with water, dried, evaporated, and the residue was chromatographed on 400 g. of alumina. Dichloromethane-pentane (2:3) eluted 0.9 g. (13%) of (SS)-108, white foam, mass spectrum (70 eV) molecular ion $m/e$ = 744, pmr spectrum (100 MHz, CDCl$_3$), δ: 2.78 ($m$, ArOCH$_2$CH$_2$, 4H); 3.52 ($t$, ArOCH$_2$CH$_2$, 4H); 4.80 ($s$, ArCH$_2$O, 4H); 6.7-7.9 (complex $m$, ArH, 28H). The compound gave the rotations, $[\alpha]_{589}^{25}$ −215°, $[\alpha]_{578}^{25}$ −231°, $[\alpha]_{546}^{25}$ −275° and $[\alpha]_{436}^{25}$ −630° (c 0.5, CHCl$_3$).

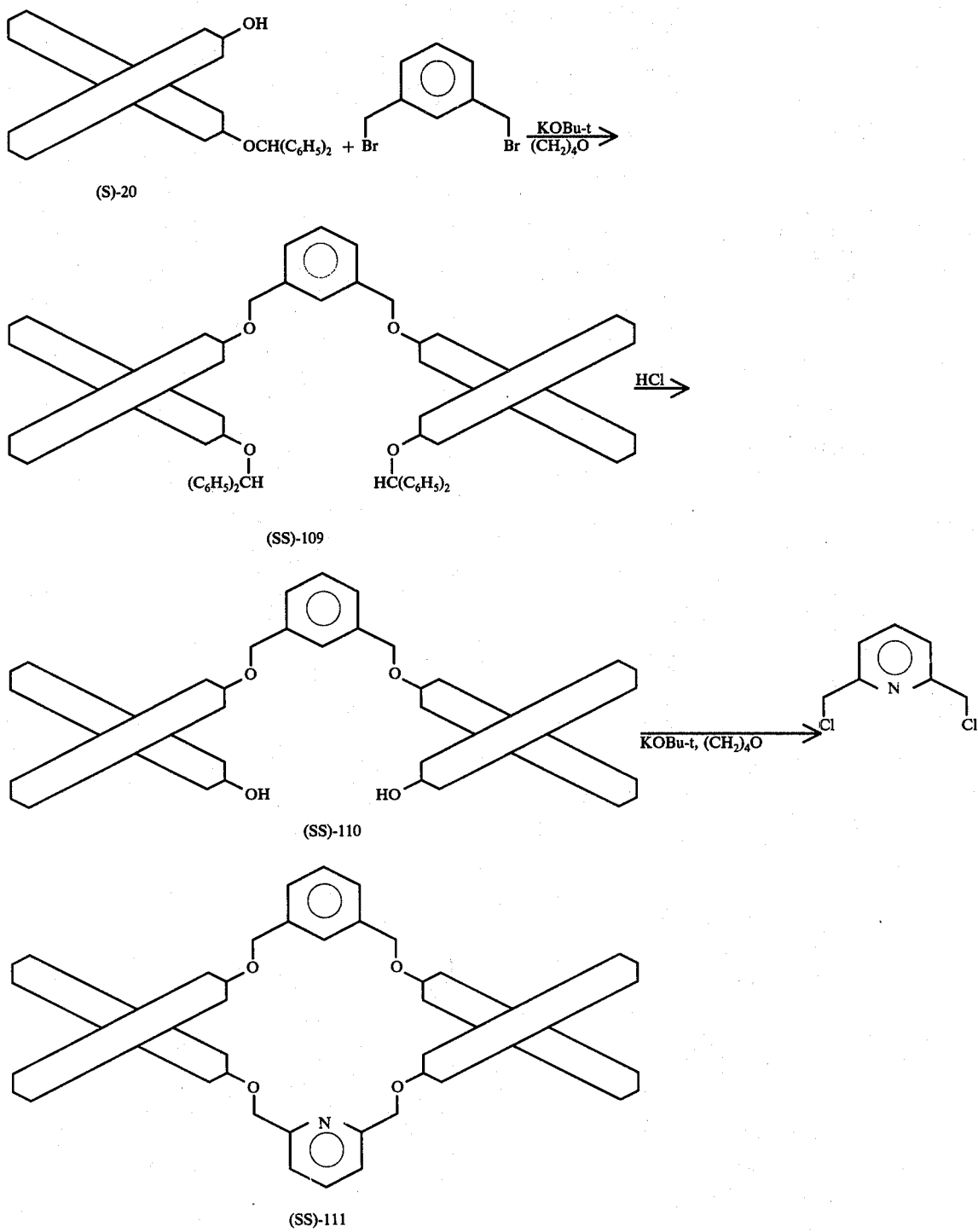

Procedure 7

This procedure reports the preparations of (SS)-109, (SS)-110 and (SS)-111. To a solution of 19.9 g. of optically pure (S)-20 in 400 ml. of tetrahydrofuran was added 4.93 g. of potassium tert-butoxide. The solution was stirred for 10 minutes, and a solution of 5.80 g. of m-xylyl dibromide in 100 ml. of tetrahydrofuran was added. The resulting solution was heated at reflux for 36 hours, the solvent was evaporated, and the dichloromethane-soluble residue was chromatographed on 700 g. of alumina. Product, 14.9 g. (67%), was washed from the column with dichloromethane-pentane (1:3). The substance, (SS)-109 was a foam, mass spectrum (70 eV) molecular ion at m/e = 1006, $[\alpha]_{578}^{25}$ −8.9°, $[\alpha]_{546}^{25}$ −11.7°, $[\alpha]_{436}^{25}$ −34.7° (c 0.6, CHCl$_3$), pmr (100 MHz, CDCl$_3$), δ: 4.64 (s, Ar$_2$CH, 2H).

Anal. Calcd for C$_{74}$H$_{54}$O$_4$: C, 88.24; H, 5.40. Found: C, 88.02; H, 5.40.

To a solution of 15.8 g. of (SS)-109 in 160 ml. of dichloromethane was added 16 ml. of concentrated hydrochloric acid and 160 ml. of methanol. The resulting cloudy mixture was stirred for 11 hours, poured into ice water, the layers were separated, and the aqueous layer was extracted with dichloromethane.

The combined organic extract was washed with water, dried and evaporated under vacuum to give 17 g. of (SS)-110, which was used in the next step without purification. It was dissolved in 300 ml. of tetrahydrofuran and mixed with 3.87 g. of potassium tert-butoxide. The solution was stirred for 10 minutes, and mixed with a solution of 2.76 g. of 2,6-bis-chloromethylpyridine in 100 ml. of tetrahydrofuran. The resulting solution was refluxed for 42 hours. An additional 1 g. portion of 2,6-bis-chloromethylpyridine and 1 g. of potassium tert-butoxide were added, and the reflux was continued for 24 hours. The solvent was evaporated, and the residue was chromatographed on 500 g. of alumina. After the column was washed with one liter of dichloromethane pentane (1:9), product was eluted with 6 liters of dichloromethane-pentane (1:1) and 3 liters of dichloromethane-pentane (3:1) to give 5.3 g. (43%) of (SS)-111 as a foam, mass spectrum (70 eV) molecular ion $m/e = 777$, $[\alpha]_{589}^{25} -269°$, $[\alpha]_{578}^{25} -283°$, $[\alpha]_{546}^{25} -339°$, $[\alpha]_{436}^{25} -798°$ (c 0.54, CHCl$_3$), pmr spectrum (100 MHz, CDCl$_3$), δ: 4.57, 4.82 (s,s, $J_{AB} = 4$Hz, ArOCH$_2$, 8H); 6.4–7.9 (complex m, ArH, 31H).

Anal. Calcd for C$_{55}$H$_{39}$O$_4$N: C, 84.92; H, 5.05. Found: C, 84.83; H, 5.18.

EXAMPLE 6

Preparation of p-Phenylene Unit-Containing Host Compounds

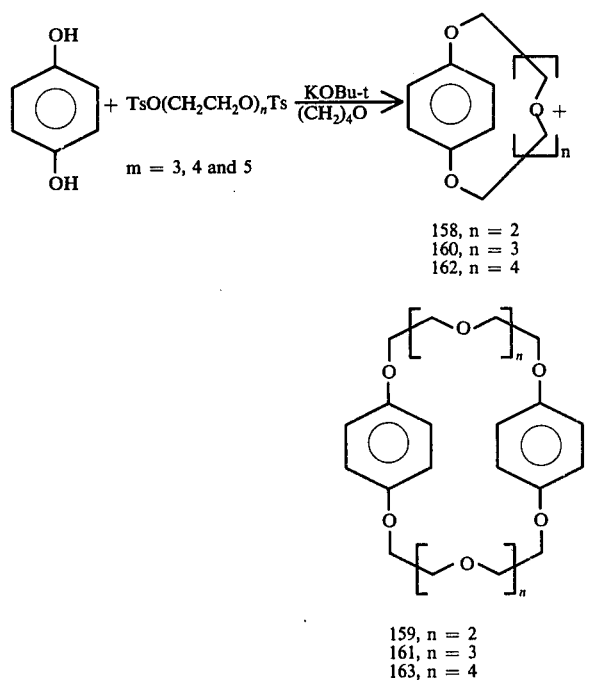

158, n = 2
160, n = 3
162, n = 4

159, n = 2
161, n = 3
163, n = 4

Procedure 1

Procedure 1 is illustrated by the preparation of cycles 162 and 163. To a solution of 11.0 g. of hydroquinone and 24 g. of potassium tert-butoxide in 600 ml. of tetrahydrofuran under nitrogen was added 98.4 g. of pentaethyleneglycol ditosylate in 400 ml. of tetrahydrofuran. The solution was refluxed for 24 hours, the potassium tosylate was collected, the solvent was evaporated from the filtrate, and the residue was dissolved in dichloromethane. The solution was washed with water, dried, evaporated, and the residue was chromatographed on 1 Kg of alumina. First ether and then chloroform was used as eluting agent, and 162 moved slightly faster than 163. The fractions rich in 163 were evaporated, and 163 was crystallized to give 2.1 g. (7%) of product, m.p. 67°–69°, mass spectrum (70 eV) molecular ion at $m/e = 624$, pmr spectrum (100 MHz, CDCl$_3$), δ: 3.6–4.1 (m, OCH$_2$CH$_2$O, 40); 6.7 (s, ArH, 8H).

Anal. Calcd for C$_{32}$H$_{48}$O$_{12}$: C, 61.52; H, 7.74. Found: C, 61.54; H, 7.54.

The fractions rich in 162 were combined with the mother liquors from the crystallization of 163, and the solvent was evaporated. The residue was subjected to a molecular distillation at 125° and 0.1 mm. to give 1.0 g. (6%) as an oil, mass spectrum (70 eV) molecular ion at $m/e = 312$, pmr spectrum (100 MHz, CDCl$_3$), δ: 3.2–3.8, 4.2 (m, CH$_2$CH$_2$, 2OH), 6.9 (s, ArH, 4H).

Anal. Calcd for C$_{16}$H$_{24}$O$_6$: C, 61.52; H, 7.74. Found: C, 61.53; H, 8.02.

Cycle 159 was similarly prepared, 7%, (except that triethyleneglycol ditosylate was employed), m.p. 96°–97°, mass spectrum (70 eV) molecular ion at $m/e = 448$, pmr spectrum (100 MHz, CDCl$_3$), δ: 3.6–4.0 (m, CH$_2$CH$_2$, 24H), 6.7 (s, ArH, 8H).

Anal. Calcd for C$_{24}$H$_{32}$O$_8$: C, 64.27; H, 7.19. Found: C, 64.29; H, 7.12.

Cycle 161 was similarly prepared, 8%, (except that tetraethyleneglycol ditosylate was employed), mass spectrum (70 eV) molecular ion at $m/e = 536$, pmr spectrum (100 MHz, CDCl$_3$), δ: 3.6–4.0 (m, CH$_2$CH$_2$, 32H); 6.7 (s, ArH, 8H).

Anal. Calcd for C$_{28}$H$_{40}$O$_{10}$: C, 62.57; H, 7.51. Found: C, 62.93; H, 7.50.

EXAMPLE 7

Preparation of Pentamethylene Unit-Containing Host Compounds

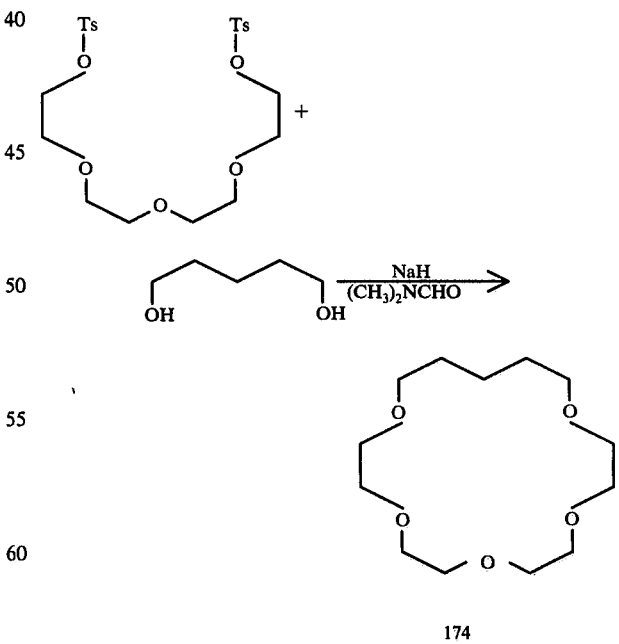

174

Procedure 1

This procedure illustrates the introduction of a pentamethylene unit into host compounds, typified specifically by cycle 174. To a stirred solution of 10.4 g. of 1,5-pentanediol in 800 ml. of dry dimethylformamide was added 10.6 g. of sodium hydride suspended in mineral oil. The solution was stirred for 1 hour at 25°, and a solution of 50.2 g. of tetraethyleneglycol ditosylate in 100 ml. of dimethylformamide was added, and the resulting solution was stirred for 6 days. The solvent was evaporated under reduced pressure, and the residue was shaken with water and dichloromethane. The organic layer was washed with 5% hydrochloric acid, with water, was dried and distilled. The product, 174, was collected at b.p. 135°–140° at 0.15 mm, weight 6.95 g. (26%). This material was brought to analytical purity by chromatography on a gel permeation column ($\frac{3}{8}$ inch by 18 foot, Biobeads SX 8, tetrahydrofuran as solvent, retention volume, 155 ml.). The compound gave a mass spectrum (70 eV) with a molecular ion +1 peak at $m/e$ = 263, and a pmr spectrum (100 MHz, CDCl$_3$), δ: 1.55 (broad s, CH$_2$(CH$_2$)$_3$CH$_2$, 6H); 3.56 (m, CH$_2$O, 2OH).

Anal. Calcd for C$_{13}$H$_{26}$O$_5$: C, 59.52; H, 9.99. Found: C, 59.41; H, 9.90.

(m, CH$_2$OCH$_2$, 4H); 3.7 (m, ArOCH$_2$, 8H); 7.14 and 7.8 (m, m, ArH, Ar'H, 24H).

Anal. Calcd for C$_{49}$H$_{42}$O$_5$: C, 82.79; H, 5.96. Found: C, 82.80; H, 5.88.

In the above examples, an (R)-binaphthyl unit may be substituted for an (S)-binaphthyl unit with analogous results.

EXAMPLE 8

General Complexing Power of Host Compounds as a Function of Structure, and Resulting Uses The uses of the host compounds reported here depend on their abilities to complex and change the properties of guest compounds. The hosts are multiheteromacrocycles whose heteroatoms provide election pairs turned inward toward their central hole. These electrons provide multiple binding sites for metal or alkylammonium cations (guest compounds) through pole-dipole interactions. By complexation, the polar cations are lipophilized by the "skin" of methylene and other hydrocarbon groups that form around the cations.

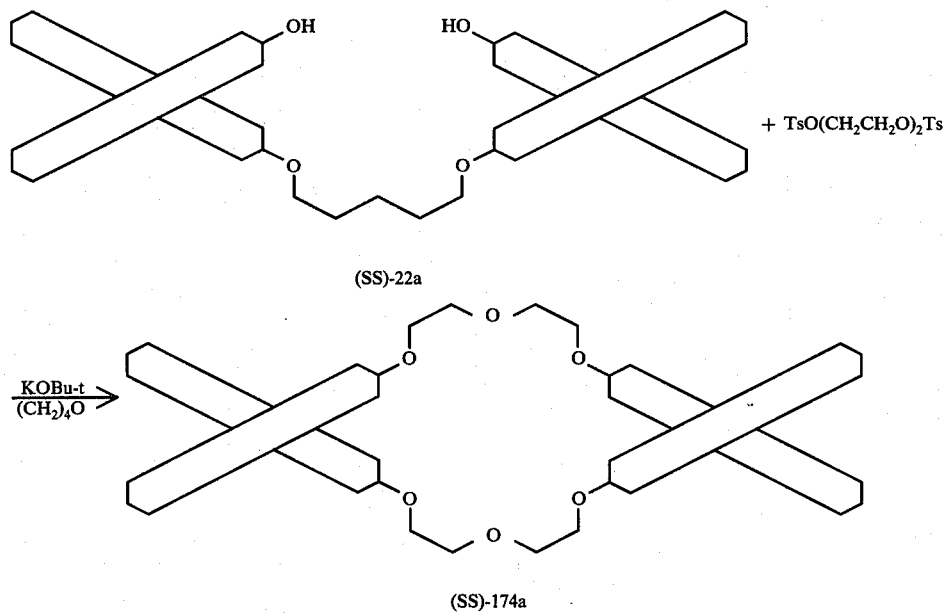

Procedure 2

This procedure records the synthesis of cycle (SS)-174a which contains the pentamethylene unit. To a solution of 3.0 g. of (SS)-22a (mixed with an equivalent amount of benzhydryl methyl ether) [see Method 1, Procedure 10] and 1.14 g. of potassium tert-butoxide in 200 ml. of tetrahydrofuran was added 2.02 g. of diethyleneglycol ditosylate. The clear solution was refluxed for 48 hours, evaporated in vacuum, and the residue was shaken with dichloromethane and water. The organic layer was dried, evaporated, and the residue was chromatographed on 200 g. of alumina. The benzhydryl methyl ether impurity (1.24 g.) was eluted with 1:9 dichloromethane-pentane. The cycle product was eluted in three one liter fractions of dichloromethane-pentane (3:7) to give 1.37 g. (71%) of 174a, obtained as a white foam, mass spectrum (70 eV) molecular ion at $m/e$ = 710, $[\alpha]_{589}^{25}$ −193°, $[\alpha]_{578}^{25}$ −203°, $[\alpha]_{546}^{25}$ −242°, $[\alpha]_{436}^{25}$ −553° (c 0.15, CHCl$_3$), pmr spectrum (100 MHz, CDCl$_3$), δ: 1.2 [m, CH$_2$(CH$_2$)$_3$CH$_2$, 6H]; 3.06

Different structural units of the guest compounds play different roles. Incorporation of rigid heterocyclic or aromatic units reduces the number of conformations available to the host compounds. The shapes of such host compounds complexed and uncomplexed more resemble one another, and conformational ambiguity is reduced in both states. The rigid units further provide positions for attachment of arms terminating in functional groups that act as additional binding sites. Some of the heterocyclic units incorporated into the macrocycle serve as starting points for synthesis of a variety of other units that provide for complementary steric and electronic relationships between host and guest.

Selective association between organic host and guest compounds is a phenomenon central to nature's enzymatic, regulatory and transport systems. Knowledge of the variation in binding ability of the host compounds with variation in structure is important to predicting the uses to which the compounds of this invention are put. As a probe for binding ability, the association constants, Ka, were determined in chloroform for tert-butylammonium thiocyanate and representatives of the multiheteromacrocycles of this invention. Equation (1) defines the association constant. The procedure used is as follows.

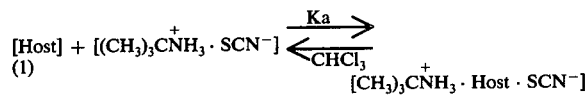

A 0.14M solution of host in $CDCl_3$ (0.6 ml.) was shaken at 24° or 0° with 1.6 ml. of 0.1M $(CH_3)_3CN^+H_3SC^-N$ in $D_2O$ (scale A), with 0.6 ml. of 0.4M salt (scale B) or with 0.3 ml. of 1.0M salt (scale C). With 100 MHz pmr spectra, the relative concentrations of guest ($CH_3$ protons) to host (all protons) in $CDCl_3$ were measured (±2%). The amount of host that dissolved in $D_2O$ was 0.5% of the total used except for 18-crown-6 (173) [J. Amer. Chem. Soc., 89, 2495 (1967)]. The value of Ka for compound 173 was corrected accordingly. The absolute amounts at equilibrium of salt extractable at 24° and 0° were determined by large scale experiments in the absence of host at initial guest concentrations of scales A, B and C. Values of K were calculated from equation (2) for each scale in which: $[BX]_{D_2O}$ and $[BX]_{CDCl_3}$ were equilibrium concentrations of salt in the absence of host; R is the ratio of concentrations of guest to host in $CDCl_3$ at equilibrium; $[BX]_i$ is the initial salt concentration in $D_2O$; $[H]_i$ is the initial host concentration in $CDCl_3$; $V_{CDCl_3}$ and $V_{D_2O}$ are the volumes of $CDCl_3$ and $D_2O$. Scales A and B were corrected to scale C by multiplying K values for scales A and B by 1.5 to give $K_a$ values. This $$K = \frac{[BX]_{D_2O}^2 R}{[BX]_{CDCl_3}(1-R)\left[[BX]_i - [H]_i R(V_{CDCl_3}/V_{D_2O})\right]^2} \quad (2)$$

factor (±20%) represents an average of the factors by which the K's of several hosts common to scales A and C or B and C differed. The values of Ka for compounds 159, 161 and 163 were not corrected for the fact that they contain two sets of binding sites. Table 1 reports the results.

TABLE I

Association Constants in Chloroform Between Hosts and tert-Butylammonium Thiocyanate

| Comp. No. | Host Structure | No. atoms macro-ring | $Ka(M^{-1})$ 24° | 0° |
|---|---|---|---|---|
| 172 | $CH_3(OCH_2CH_2)_5OCH_3$ | 0 | 40 | 30 |
| | $-[-A-O-]_a-[-B-O]_b-$ | | | |
| 173 | $A=CH_2CH_2$, a=6, b=0 | 18 | $7.5 \times 10^{5c}$ | $8.9 \times 10^{5c}$ |
| 174 | $A=CH_2CH_2$, a=4, $B=(CH_2)_5$, b=1 | 18 | $5.0 \times 10^2$ | $6.5 \times 10^2$ |
| 96 | $A=CH_2CH_2$, a=4, $B=m-CH_2C_6H_4CH_2$, b=1 | 18 | $1.5 \times 10^3$ | $2.0 \times 10^3$ |
| 175 | $A=CH_2CH_2$, a=5, $B=o-C_6H_4$, b=1 | 18 | $1.4 \times 10^5$ | $2.8 \times 10hu 5$ |
| 176 | $A=B=o-C_6H_4(OCH_2CH_2)_2$, a=b=1 | 18 | $1.3 \times 10^4$ | $1.5 \times 10hu 4$ |
| 177 | $A=B=$ cyclohexyl$(OCH_2CH_2)_2$, a=b=1 | | $9.5 \times 10^4$ | $2.5 \times 10hu 5$ |
| 71 | $A=$ furan, a=1, $B=CH_2CH_2$, b=4 | 18 | $1.1 \times 10^6$ | $6.6 \times 10hu 5$ |
| 45 | $A=$ furan, a=1, $B=CH_2CH_2$, b=4 | 18 | $4.8 \times 10^4$ | $3.3 \times 10hu 4$ |
| 46 | $A=$ furan, a=2, $B=CH_2CH_2$, b=2 | 18 | $4.1 \times 10^3$ | $4.0 \times 10hu 3$ |
| 48 | $A=$ furan, a=3, b=0 | 18 | $3.1 \times 10^2$ | $4.0 \times 10hu 2$ |
| 47 | $A=$ furan, $CH_2CH_2$, a=b=1 | 18 | $8.0 \times 10^1$ | $7.0 \times 10hu 1$ |
| 11 | $A=$ pyridine, a=1, $B=CH_2CH_2$, b=4 | 18 | $1.4 \times 10^6$ | $3.0 \times 10hu 5$ |
| 12 | $A=B=$ pyridine$-CH_2CH_2$, a=b=1 | 18 | $4.2 \times 10^5$ | $1.2 \times 10hu 6$ |

TABLE I-continued
Association Constants in Chloroform Between Hosts and tert-Butylammonium Thiocyanate

| Comp. No. | Host Structure | No. atoms macro-ring | $K_a(M^{-1})$ 24° | $K_a(M^{-1})$ 0° |
|---|---|---|---|---|
| 15 | A= [pyridine], a=3, b=0 | 18 | $6.6 \times 10^5$ | $2.0 \times 10^6$ |
| 16 | A= [pyridine], a=2, b=0 | 12 | $2.4 \times 10^2$ | $8.0 \times 10^1$ |
| 17 | A= [pyridine], a=4, b=0 | 24 | $2.1 \times 10^2$ | $1.1 \times 10^2$ |
| 162 | A= —[phenyl]—(OCH$_2$CH$_2$)$_5$, a=1, b=0 | 20 | <40 | <30 |
| 163 | A=B= —[phenyl]—(OCH$_2$CH$_2$)$_5$, a=b=1 | 36 | $5.0 \times 10^1$ | $3.0 \times 10^1$ |
| 161 | A=B= —[phenyl]—(OCH$_2$CH$_2$)$_4$, a=b=1 | 30 | $8.0 \times 10^1$ | $4.0 \times 10^1$ |
| 159 | A=B= —[phenyl]—(OCH$_2$CH$_2$)$_3$, a=b=1 | 24 | <40 | <30 |
| 178 | [binaphthyl structure with O(CH$_2$CH$_2$O)$_2$CH$_3$ groups] | 0 | $5.0 \times 10^1$ | $4.0 \times 10^1$ |
| 179 | [structure with O(CH$_2$CH$_2$O)$_2$ bridges] | 20 | $4.2 \times 10^2$ | $6.0 \times 10^2$ |
| 180 | [structure with OCH$_2$CH$_2$OCH$_2$CH$_2$O bridges] | 22 | <40 | <30 |

Compounds 173 and 175–177 were included for comparison purposes. Compounds 173 and 175–177 have been reported, [J. Amer. Chem. Soc., 89, 2495 (1967)], and 174 were prepared specifically for this study (see Example 7, Procedure 1). Compounds 178–180 were previously prepared, (U.S. Patent application Ser. No. 346,089, filed Mar. 29, 1973).

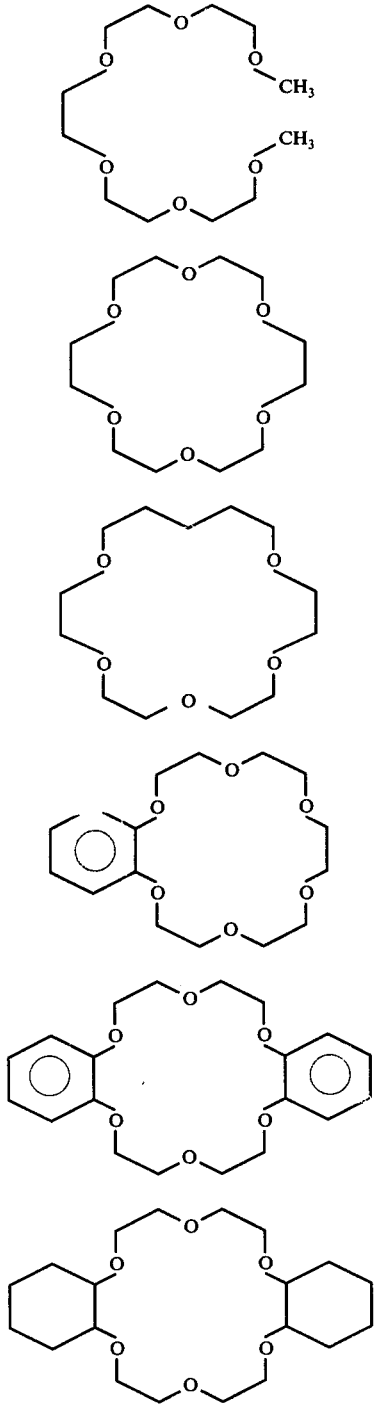

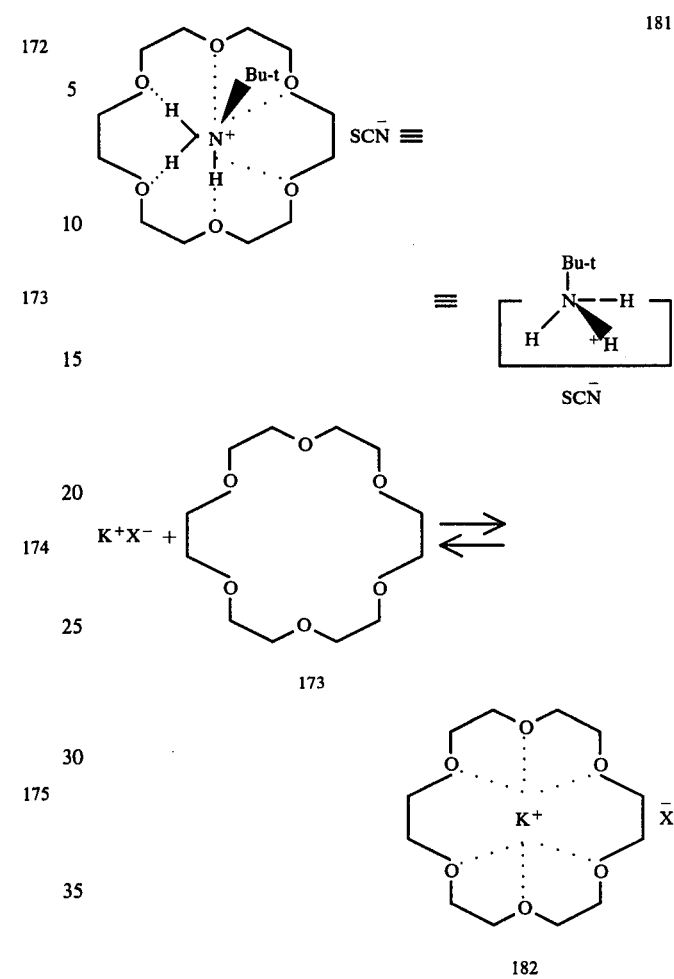

Of the cycles of Table I, 173 has the highest symmetry. The reasonable structure for its complex with tert-butylammonium thiocyanate is 181, in which three hydrogen bonds hold host to guest in a rigid arrangement. Complex 181 resembles 182, in which a potassium ion is complexed by 173 [(J. Amer. Chem. Soc., 89, 2495 (1967)].

The data of Table I support the mode of complexation envisioned in 181, and provides indirect evidence for the structures of the other complexes as well. 1) In compound 162, the aryl oxygens are remote from one another because of their attachment to a

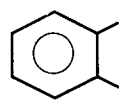

unit. In isomeric compound, 175, the aryl oxygens are held close to one another by the

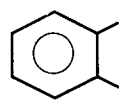

unit. Examination of molecular models of 162 (CPK, or Corey-Pauling-Koltun) indicates that a maximum of three oxygens at a time can be used in binding $RN^+H_3$, whereas in 175, all six oxygens are available. Compound 175 is the better host by a factor of $>3.5 \times 10^3$ (compare the Ka values).

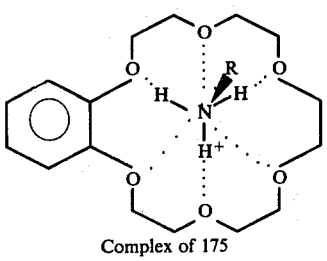

Complex of 175

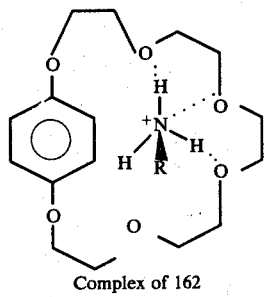

Complex of 162

2. Cycle 173, whose six oxygens are well organized for binding, possesses a Ka value a factor of $>10^4$ higher than that of its open-chain counterpart, 172. Clearly, high molecular organization prior to complexation increases the tendency to complex. Furthermore, cyclic binaphthyl compound

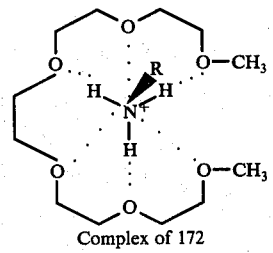

Complex of 172

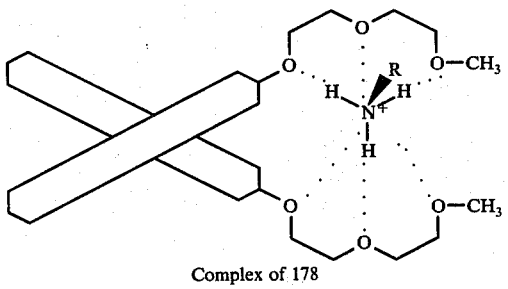

Complex of 178

179 has a Ka about 10 times higher than that of its non-cyclic counterpart, 178. Again the effect of organization of binding cites prior to complexation is visible. 3) Substitution by a methylene for one of the oxygens of 173 as in 174 reduced the constant by a factor of $1.5 \times 10^3$. Molecular models of the complexes of 173 and 174 indicate them to be sterically comparable. The difference in their binding constants appears to be due to the difference between five and six binding sites. Thus the non-hydrogen bonded electron pairs of the alternate oxygens stabilize electrostatically the $N^+$, which molecular models (CPK) indicate are very close in the complex of 181. (4) Substitution of a m-xylyl group as in cycle 96 for one of the $CH_2CH_2OCH_2CH_2$ groups of 173 reduced the constant by a factor of about 500.

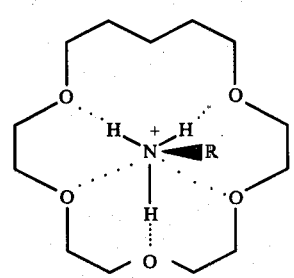

Complex of 174

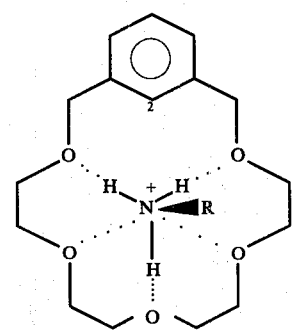

Complex of 96

Again the absence of the sixth oxygen in 96 is reflected in its binding constant, but the effect is less pronounced than in that of 174. Molecular models of the complex of 96 indicate the plane of the aryl is tilted somewhat relative to that of the best plane of the oxygens. This geometry places substituents attached to the 2-position of the aryl in complexes such as 96 directly under the complexed cation. 5) Successive substitution of o-phenylyl for ethylene units of 173 as in the complexes of 175 and 176 reduced the constant by a factor about $2 \times 10^3$ for the first and by an additional factor of $>8$ for the second. The aryl inductive and delocalization effects on the electron pairs of the oxygens are visible in these results. (6) Successive substitution of 2,5-furandimethylyl for $CH_2CH_2OCH_2CH_2$ units of 173 as in the complexes of 45, 46 and 48 reduced the constant by factors of 12 to 16 per unit. These effects probably are due to electron-delocalization from oxygen into the furan systems, and to the inductive effect of the furan systems. When two furan units are 180° from one another as in the complex of 46, Ka is about 50 times lower than when they are 120° as in that of 47. In

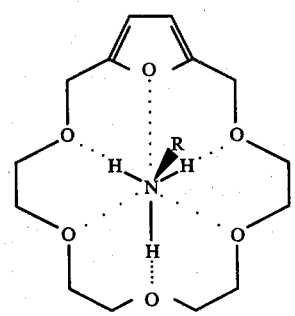

Complex of 45

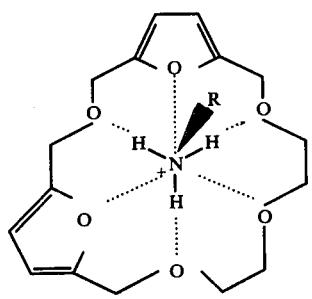

Complex of 47

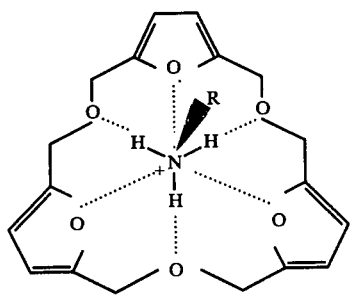

Complex of 48

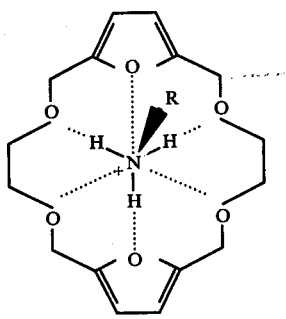

Complex of 46 the complex of 47, three hydrogen bonds can go to the more basic three non-furanyl oxygens. In the complex of 46, one hydrogen bond must involve a relatively non-basic furanyl oxygen. (7) Substitution of 2,6-pyridinedimethylyl for the $CH_2CH_2OCH_2CH_2$ units of 173 as in the complexes of 11, 12 and 15 produces little change in Ka. In the complex of 12, one of the hydrogen bonds must go to the pyridyl nitrogen

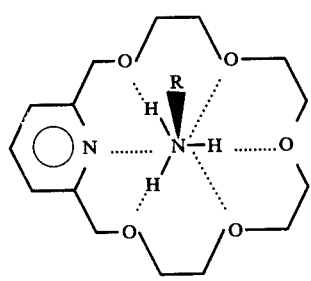

Complex of 11

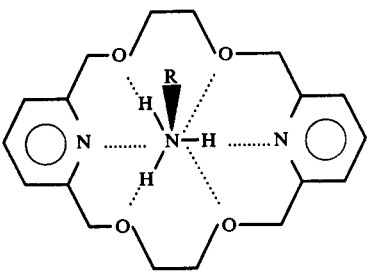

Complex of 12

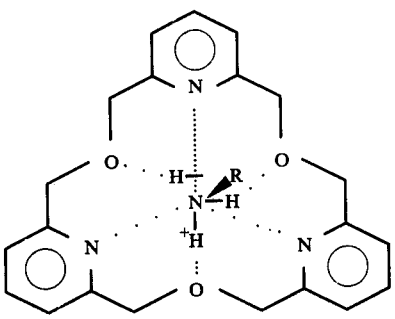

Complex of 15 electron pair ($N^+$-H . . . :N), and one pyridyl nitrogen electron pair must electrostatically stabilize the ion by near contact ($N^+$. . . :N). Apparently oxygen and pyridyl nitrogen are nearly equivalent in their abilities to bind in these ways. Although the hydrogen bonds in the complexes of 11 and 15 are drawn to oxygen, molecular models indicate they could be drawn equally well to nitrogen. The pyridyl rings are slightly tilted out of the best plane of the heteroatoms in models of the complexes, and the complex is superbly well organized. When the macroring is reduced to 12 atoms as in 16 or expanded to 24 as in 17, the Ka values are reduced by factors of about $10^4$. The organization of three hydrogen bonds and three pole to dipole binding forces appears critical to strong binding. (8) Introduction of a

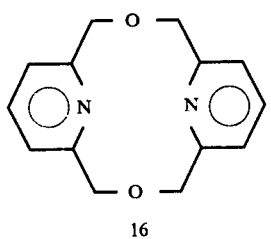

16

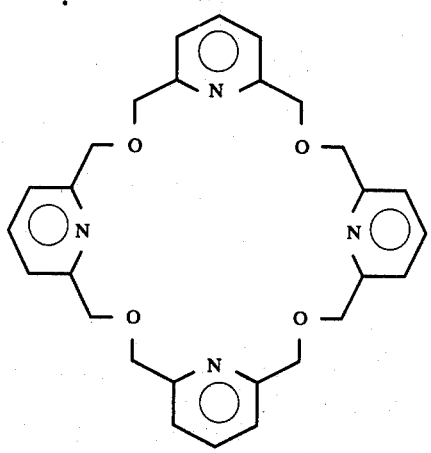

17

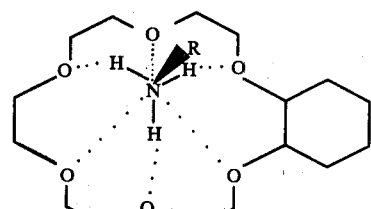

Complex of 71

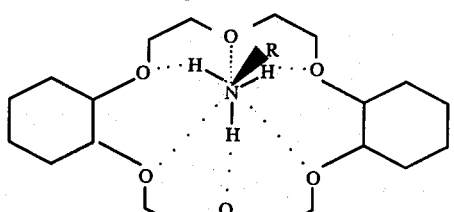

Complex of 177 tetrahydro-2,5-furandimethylyl in place of a CH₂CH₂OCH₂CH₂ unit of 173 as in the complex of 71 produced little change in Ka. However, substitution of two 1,2-cyclohexyl for two CH₂CH₂OCH₂CH₂ units of 173 as in the complex of 177 reduced Ka by about a factor of 10. (9) The binding constants of 163 and 161 are close to one another, and are higher by a factor of 1.5 to 2 than that of 172 or 159. Molecular models of the complex of 161 appears the best organized of the four in spite of only five oxygens being available at each of its two binding loci. The thickness of the benzene rings prevents all six oxygens of each end of the ethyleneoxy chains of 163 from completely surrounding the NH₃⁺ group, and models suggest that only five are used. (10) Substitution of binaphthyl

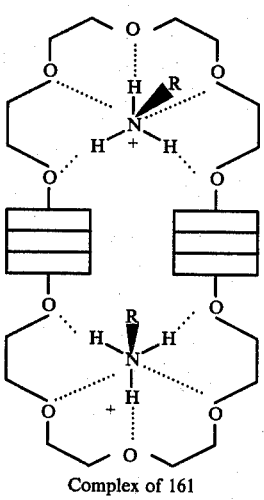

Complex of 161

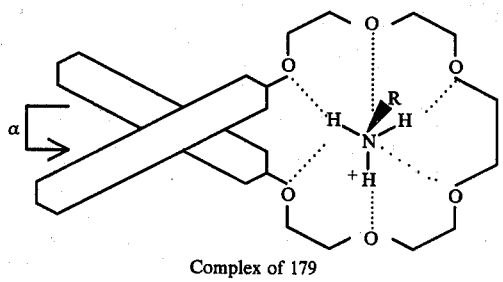

Complex of 179

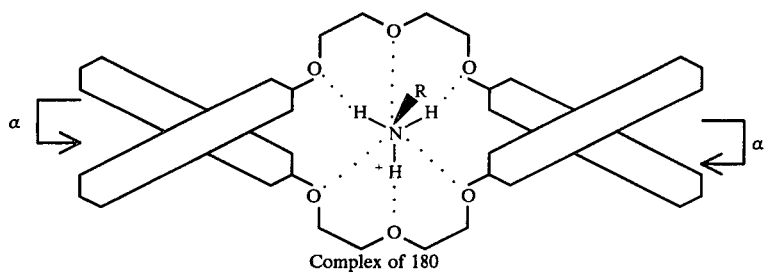

Complex of 180 for ethylene units of 173 as in the complexes of 179 and 180 reduced the constant by a factor of $2 \times 10^3$ for the first, and by an additional factor of $>8$ for the second. Unlike most of the other units, the binaphthyl can locate its attached oxygens either as close together as an ethylene unit, or considerably further apart, depending on the value of the dihedral angle, $\alpha$, between the planes of the two naphthalene rings. This additional structural degree of freedom coupled with the inductive and electron delocalization effect of the naphthalene rings on their attached oxygens are probably responsible for the decreased binding power of 179 and 180. Since hosts as poor as 180 can provide highly structured complexes [J. Amer. Chem. Soc., 95, 2692 (1973)], these results indicate that units of a wide structural variety are available for designing host molecules for a variety of purposes. (11) A temperature lowering of 24° produced a maximum increase in binding constant by a factor of 3(pyridyl systems), and a maximum decrease by a factor of 3(pyridyl systems). Thus the large changes of Ka with changes in structure appear to be more associated with enthalpy than with entropy changes upon complexation.

Others have demonstrated that multiheteromacrocycles such as 175-177 complex Group I and II, and silver cations [J. Amer. Chem. Soc., 93, 600 (1971)] and lipophilize them [J. Amer. Chem. Soc., 89, 7017 (1967); ibid., 92, 386, 391 (1970); ibid., 95, 3023 (1973)]. As with 175-177, the compounds of this invention complex and lipophilize selectively ammonium, alkylammonium, and metal cations of lithium, sodium, potassium, rubidium, cesium, silver, magnesium, calcium, strontium, zinc, lead, manganese, cobalt, iron, copper, chromium, mercury and molybdenum.

As with the compounds reported in the above references, the complexing ability of the compounds reported here varies with: (1) the match between hole diameter of host and diameter of ionic guest; (2) the match in stable arrangement of heteroatoms of the uncomplexed host, and the most stable ligand arrangement for the ionic guest; (3) the match in heteroatom type of the host, and the most stabilizing ligand type for the ionic guest; (4) in the appropriate cases, the match between negative charges located in the host and positive ions in the guest.

Selective complexation and lipophilization of alkylammonium and metal cations provides the compounds of this invention with a variety of uses that depend on complexed ions having different properties than non-complexed. The uses are: antibiotics, or antibiotic potentiators; drug delivery systems; fermentation aids; fungicides; herbicides; agents for delivery of ions in and out of cells; antielectrostatic agents; antiscaling agents; agents that catalyze more complete combustion; electrolylic agents; antifoaming agents; desalination agents; nuclear magnetic resonance shift reagents; gelling agents; dispersing agents; anticorrosion agents; assymetric reagents and catalysts for causing asymmetric induction during reactions; resolving agents for amines, amino acids and their derivatives; agents for introduction of trace metals into living systems in biologically useful forms; agents for aiding in the separation of elements that are products of atomic piles; agents for isotope fractionation; sterically and electronically tailored compounds for transition metal catalysis in lipophilic media; agents for dispersing metal ions evenly in gels used in photographic processes.

EXAMPLE 9

Specific Examples of Complexing Power of Multiheteromacrocycles

Examples are provided here of the formation of specific complexes between multiheteromacrocycles and several types of host compounds.

$(CH_3)_3C\overset{+}{N}H_3\ \overset{-}{SCN}$ +

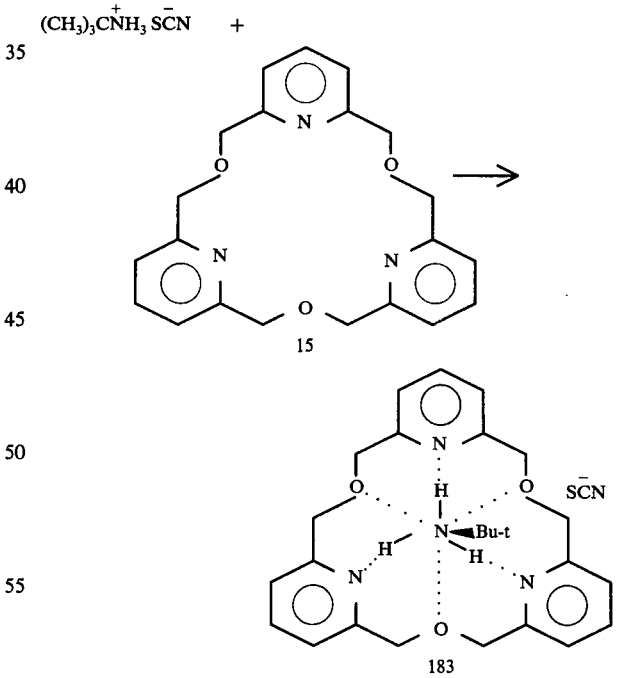

Procedure 1

Procedure 1 illustrates how crystalline one-to-one complexes between primary amine salts and multiheteromacrocycles can be prepared. For example, to a solution of 45 mg. of 15 in 1 ml. of chloroform was added 15 mg. of tert-butylammonium thiocyanate. A few drops of tetramethylsilane were added, and the mixture was cooled to 0°. The crystals that separated (48 mg. of 83%) gave m.p. 198°-201° (dec.), mass spectrum (70 eV), parent ion m/e = 363 (molecular ion of 15).

Anal. Calcd for $C_{26}H_{33}N_5O_3S$: C, 63.01; H, 6.71. Found: C, 62.90; H, 6.88.

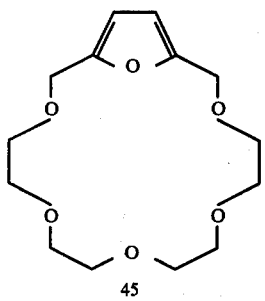

45

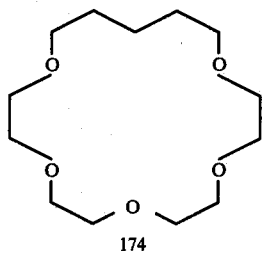

174

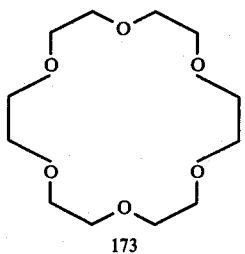

173

Procedure 2

Procedure 2 illustrates how crystalline one-to-one complexes of multiheteromacrocycles such as 45, 174 and 173 and dimethyl acetylenedicarboxylic ester can be formed. A mixture of 1.0 g. of 45, 1.5 g. of dimethyl acetylenedicarboxylic ester and 5 ml. of benzene was stirred at 25°. A white crystalline solid separated, 1.1 g. (74%), m.p. 72°-73°, mass spectrum (70 eV) molecular ion of 45 m/e = 286, pmr (100 MHz, $CDCl_3$), δ: 3.57 (s, $OCH_2CH_2O$, 16H); 3.78 (s, $CH_3$, 6H); 4.44 (s, $C-CH_2O$, 4H); 6.18 (s, ArH, 2H).

Anal. Calcd for $C_{20}H_{28}O_{10}$: C, 56.07; H, 6.59. Found: C, 56.02; H, 6.67.

This complex undergoes molecular distillation from its melt, and solid complex accumulates on the condenser. When submitted to gel permeation chromatography in tetrahydrofuran as solvent, the complex separates into two overlapping components. When submitted to the extraction-complexation experiments with $(CH_3)_3CN^+H_3SCN$ (Example 8) at both 24° and 0°, the complex gave results identical to those given by 45 alone. The pmr spectrum in $CDCl_3$ of 45 alone and its complex are almost identical except for the presence in that of the latter of the $CH_3$ signal.

Similarly 174 formed a one-to-one complex with dimethyl acetylenedicarboxylic ester. A solution of 1.0 g. of 174 was mixed with 1.0 g. of dimethyl acetylenedicarboxylic ester (heat was evolved). The resulting solution deposited crystals, which were triturated with pentane to give complex, which after drying at high vacuum and 25° for 48 hours gave 1.2 g. of complex, m.p. 63°-64°, pmr spectrum (60 MHz, $CDCl_3$), δ: 1.53 (broad s, $CH_2(CH_2)_3CH_2$, 6H); 3.53, 3.60 (s, s, $OCH_2$, 2OH); 3.78 (s, $OCH_3$, 6H).

Anal. Calcd for $C_{19}H_{32}O_9$: C, 56.42; H, 7.98. Found: C, 56.44; H, 8.09.

Both 174 and dimethyl acetylenedicarboxylic ester are non-crystalline. The fact that heat is evolved when they are mixed indicates molecular complexation occurs in solution as well as in their crystalline state.

Similarly, 173 formed a one-to-one complex with dimethyl acetylenedicarboxylic ester. A solution of 0.40 g. of about 85% pure (pmr) 173 and 0.40 g. of dimethyl acetylenedicarboxylic ester in 5 ml. of benzene was allowed to stand for 2 days at 25°. The crystals that separated were collected, 0.32 g. (50%), m.p. 100°-101°. An osmometric molecular weight of an 0.02 M solution of the complex in chloroform gave an apparent molecular weight of 201, as compared to a molecular weight calculated for the complex of 406. Thus the complex is dissociated in chloroform at this concentration and temperature.

Anal. Calcd for $C_{18}H_{30}O_{10}$: C, 53.19; H, 7.44. Found: C, 53.27; H, 7.53.

The X-ray crystal structures of the complex of 173 has been determined. The acetylene is not threaded through the hole of 173, nor are the ester groups coordinated with the ether oxygen of 173. Rather, the methyl of the ester group is inserted into the hole of 173 to form two hydrogen bonds of the unusual sort, C—H . . . :O, and one unusual

electrostatic interaction per methyl group. These two types of binding are indicated by the fact that the intermolecular distances between the indicated atoms are about 0.3 A units shorter than the usual van der Waals distances.

Procedure 3

Dry macroreticular resin [Amberlyst-15, polystyrenesulfonic acid, Rohm and Haas, 40-60 mesh, average pore diameter, 200-600 A] saturated with $H_3O^+$, $Na^+$, $K^+$, $NH_4^+$, or $Cs^+$ (25–50 mg.) was mixed with 5 to $12\times10^{-5}$ M solution of cycle in dry dichloromethane. Th solution's optical density (λ 250–340 mm) was measured before mixing and monitored until constant while the mixture was shaken at 25°. For each cycle and cation, the resin became saturated with cycle to an extent (±5%) independent of cycle concentration in dichloromethane. Saturation constants are defined as $K_s = 100$ X (moles absorbed cycle)/(moles cation present), and provide a measure of the complexing power of each cycle for each cation at the resin-solvent interface. Table II records the results. The syntheses of compounds 175, 176 and 184 have been reported [J. Amer. Chem. Soc., 89, 2495 7017 (1967)]. Tribenzylamine is included for comparative purposes with resin-$H_3O^+$, $K_s = 18.6$. The constants for 175, 176 and 184 have been reported [J. Amer. Chem. Soc., 95, 2691 (1973)].

TABLE II

Saturation Constants ($K_s$) For Host Molecules in Dichloromethane Against Resin-$SO_3^-M^+$ at 25°

| Host | $K_s$ for $M^+$ equals | | | | |
|---|---|---|---|---|---|
| | $H_3O^+$ | $Na^+$ | $K^+$ | $NH_4^+$ | $Cs^+$ |
| 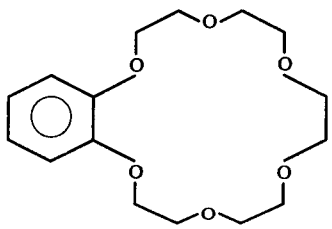 175 | 3.6 | 1.1 | 1.3 | 1.05 | 0.69 |
| 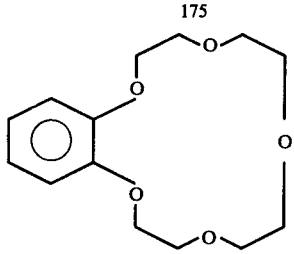 184 | 1.3 | 1.2 | 0.69 | 0.43 | 0.19 |
| 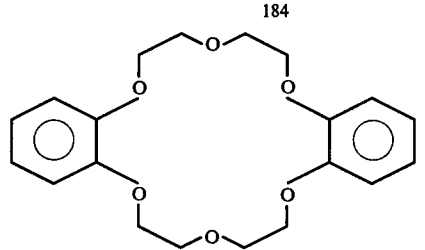 176 | 1.35 | 0.89 | 0.97 | 0.65 | 0.40 |
| 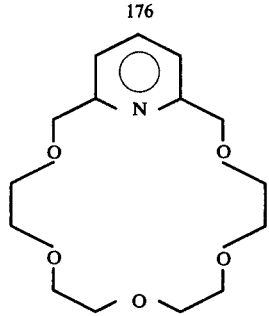 11 | | | | | |
| 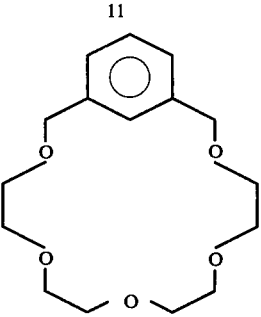 96 | 4.56 | 4.0 | 1.76 | 0.91 | 0.00 |

These data indicate that host compound 11 in this test is a better complexer of $H_3O^+$, $Na^+$, $NH_4^+$ and $Cs^+$ than reference compounds 175, 184 or 176, and a comparable or better complexer of $K^+$. Host compound 96 is a better complexer of $H_3O^+$, $Na^+$, $K^+$ than reference compounds 175, 184 and 176. Toward $NH_4^+$, 96 is between 175 and 184, and toward $Cs^+$ is the poorest complexer of the five cycles.

Procedure 4

In procedure 4, the pKa values of the pyridine-containing cycles are reported, and are compared with those of pyridine and of 2,4,6-trimethylpyridine [Pure and Applied Chemistry, Suppl. (1965) report pKa values of 5.2 for pyridine and 7.4 for 2,4,6-trimethylpyridine]. Solutions of about 0.1 milliequivalent of host in 40 ml. of water at 20° were titrated with $0.10\pm0.01$ N LiOH and $0.10\pm01$ N HCl solutions. The pH of the solutions was monitored with a glass electrode and pH meter. The pKa values were determined by graphic analysis of a plot of pH vs ml. of added titrant, and are recorded in Table III.

TABLE III

Values of pKa of the Conjugate Acids of Pyridine-Containing Host and Reference Compounds

| Compound | Acid (A) or Base (B) titration | pKa | average |
|---|---|---|---|
| 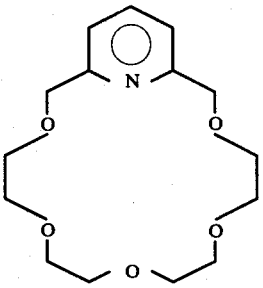 11 | A<br>B<br>A<br>B | 4.75<br>4.75<br>4.85<br>4.70 | 4.8 |
| 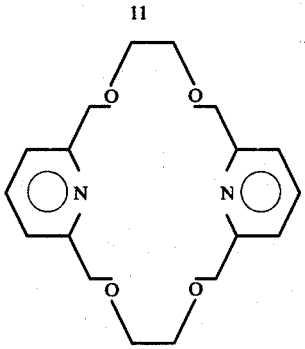 12 | B<br>A<br>B<br>A | 5.2, 3.7<br>5.4, 3.6<br>5.4, 3.7<br>5.3, 3.6 | 5.3, 3.6 |
| 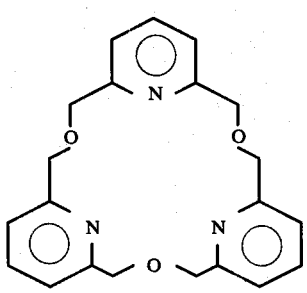 15 | B<br>A<br>B<br>A | 4.9, 3.5<br>5.5, 3.6<br>5.5, 4.0<br>5.2, 3.8 | 5.3, 3.7 |
| 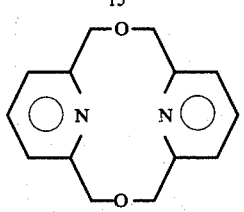 16 | B<br>A<br>B<br>A<br>B | 7.8<br>7.9<br>7.8<br>7.85<br>8.0 | 7.9, <3 |

TABLE III-continued
Values of pKa of the Conjugate Acids of Pyridine-Containing Host and Reference Compounds

| Compound | Acid (A) or Base (B) titration | pKa | average |
|---|---|---|---|
| (structure, labeled 17) | B<br>A | 4.5, >3<br>5.0, >3 | 4.8, >3 |
| (pyridine) | B<br>A | 5.1<br>5.0 | 5.15 |
| (2,4,6-trimethylpyridine) | B<br>A | 7.4<br>7.4 | 7.4 |

The pKa values of 11, 12, 15 and 17 are remarkably close together (4.8–5.39), a fact that indicates that the microscopic environment of the monoprotonated compounds are rather similar. The other pyridine units or ether oxygens of the compound seem to play little role in solvating the $N^+$-H species, and in inhibiting water from solvating it. These pKa values are close to that of pyridine (5.2) itself. The diconjugate of 12, 15 and 17 have pKa values of between 3 and 4.

In contrast, the monoconjugate acid of 16 was 7.9, and that of the diconjugate acid of 16 was well below 3 (not measurable). Clearly the monoconjugate acid of 16 is unusually stabilized. CPK molecular models of the monoconjugate acid of 16 suggest that its structure is 185, in which the one proton is shared by two nitrogens and two oxygens of 16. Thus 16 is a stronger base than 2,4,6-trimethylpyridine,

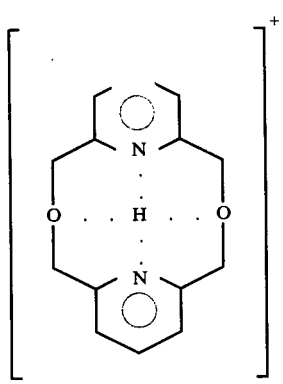

185 whose three methyl groups are electron releasing (considerably more than the $OCH_2$ groups of the cycles). Since the nitrogens of 16 are far too hindered to be nucleophilic, and the pKa of 185 is close to physiological pH, 16 like imidazole is a good general basic catalyst for reactions carried out under physiological conditions.

EXAMPLE 10
Chiral Recognition in Selective Complexation by Host Compounds of Enantiomers of Amino Ester Salts Procedures were developed previously (application No. 346,089, filed Mar. 29, 1973) to use compound (SS)-180 and its analogues to resolve amino esters through chiral recognition and selective complexation in solution [see also *J. Amer. Chem. Soc.*, 95, 2692 (1973)]. The technique involves distributing the two enantiomers of racemic amino ester hexafluorophosphate salts between a chloroform phase containing a host compound, and an aqueous phase containing $NaPF_6$ or $LiPF_6$ as a salting out agent. The relative amounts of host and guest at equilibrium in each phase were

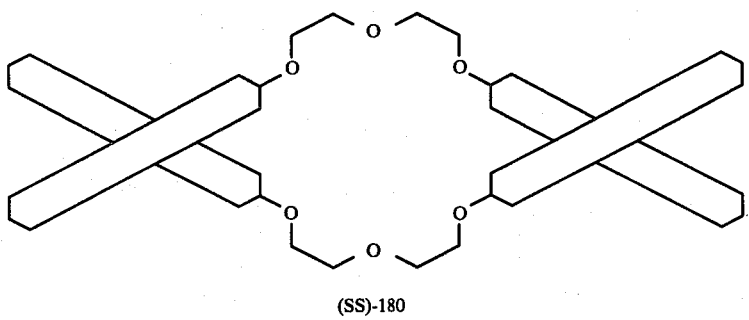

(SS)-180 determined by pmr spectral measurements. The absolute configurations and maximum rotations of all hosts and guests have been previously determined.

The procedure was as follows. Enough racemic amine hexafluorophosphate was dissolved in $D_2O$, 1.0 to 4.0 M in $LiPF_6$ (at pH ~ 4 to 5) to give a 1 M solution of amine salt. This solution was shaken at the desired temperature with solutions of optically active host compounds (about 0.2 M) in $CDCl_3$. The pmr spectra of each layer was taken, and no host compound was detected in the aqueous layer. The layers were separated, the amines were isolated from each layer, and their optical purities and configurations determined. The results provided enantiomer distribution constants, $EDC = D_A/D_B$, where $D_A$ is the distribution coefficient of the enantiomer more complexed in $CDCl_3$, and $D_B$ is that of the enantiomer less complexed. Both enantiomers of amino esters were found to complex (SS)-180, and the two diasteromeric structures formulated were refered to as the three-point binding model (186) and the four-point binding model (187). In the latter, besides the three hydrogen bonds, the complex is held together by a carbonyl-to-ether oxygen dipole-to-dipole interaction.

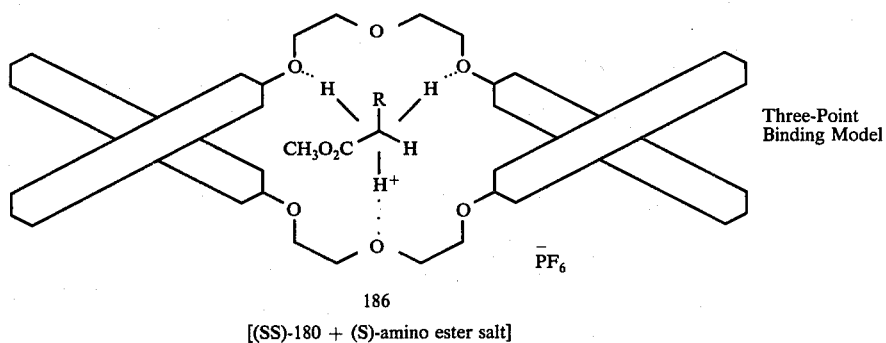

186
[(SS)-180 + (S)-amino ester salt]

Three-Point Binding Model

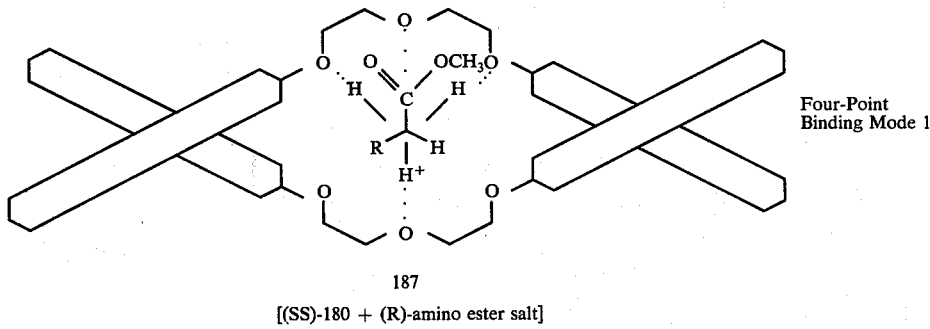

187
[(SS)-180 + (R)-amino ester salt]

Four-Point Binding Mode 1

Optically pure compounds (SS)-19, (SS)-23, (SS)-23a, (SS)-108, (SS)-111, (SS)-174a and (SS)-108 were examined similarly, for their complexing power (how much amino ester salt do they draw into chloroform?), for their chiral recognition (how much greater than unity are their EDC values), and for the direction of their chiral recognition (which diastereomeric complex is the more stable, that represented by the three-point binding model, or that represented by the four-point binding model?). Table IV records the results. The values reported previously in [application Ser. No. 346,089 filed Mar. 29, 1973], for compound (SS)-180 are included for purposes of comparison.

The results clearly indicate that whereas (SS)-174a and (SS)108 are too poor at complexing to be useful for

TABLE IV

Binding Power, Enantiomer Distribution Constants (EDC), and Direction of Chiral Recognition in Molecular Complextion

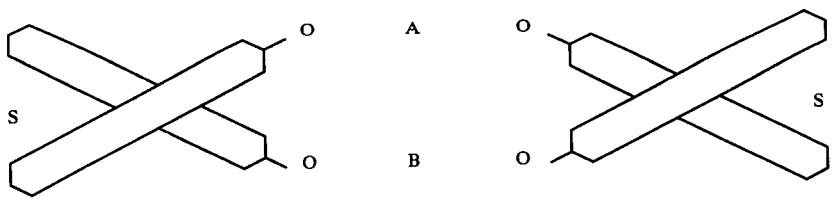

| A | B | No. | R of R—CH—CO$_2$CH$_3$ \| NH$_3$PF$_6$ | T °C | pH D$_2$O | [Guest]/ [Host] | Applicable Model | EDC |
|---|---|---|---|---|---|---|---|---|
| (diether) | (diether) | (SS)-180 | C$_6$H$_5$ | −5 | 4 | 0.9 | three-point | 3.0 |
|  |  |  | C$_6$H$_5$ | −10 | 4 | 0.9 | three-point | 2.8 |
|  |  |  | C$_6$H$_5$ | −14 | 4 | 0.9 | three-point | 3.1 |
|  |  |  | (CH$_3$)$_2$CH | −10 | 4 | 0.9 | four-point | 1.5 |
| (diether) | (dialkyl) | (SS)-174a | C$_6$H$_5$ | −15 | 4 | <0.1 | — | — |
| (diether) | (phenyl) | (SS)-108 | C$_6$H$_5$ | −15 | 4 | <0.1 | — | — |
| (diether) | (pyridyl) | (SS)-23 | C$_6$H$_5$ | −10 | 4.3 | 1.0 | three-point | 1.7 |
|  |  |  | (CH$_3$)$_2$CH | −10 | 4.4 | 0.8 | three-point | 1.24 |
| (dialkyl) | (pyridyl) | (SS)-23a | C$_6$H$_5$ | −13 | 5.2 | 0.38 | three-point | 1.35 |
|  |  |  | (CH$_3$)$_2$CH | −16 | 5.2 | <0.1 | — | — |
| (pyridyl) | (pyridyl) | (SS)-19 | C$_6$H$_5$ | −16 | 5 | 0.7 | three-point | 2.0 |
|  |  |  | (CH$_3$)$_2$CH | −16 | 5 | 0.3 | three-point | 1.3 | optical resolution of amino esters, compounds (SS)-23, (SS)-23a, (SS)-111 and (SS)-19 provide large enough EDC factors (1.24 to 2.0) to make them useful for this purpose. By multiplate processes (countercurrent or liquid-liquid chromatographic), or by attachment of the host compounds to solid supports [as with (SS)-180, see application Ser. No. 346,089 filed Mar. 29, 1973]employed in solid-liquid chromatography, the latter compounds can be used for total resolution of primary amine racemates, amino acids, amino esters, amino amides, and peptides. Analytical reagents for determination of absolute configuration or determining optical purity (e.g. optically active "shift reagents" for use in pmr spectra) are further uses to which the enantiomers of 23, 23a, 111 and 19 are put.

Compounds 23, 23a, 111 and 19 are chiral, and contain the basic pyridyl function in a highly shaped environment. Pyridine unit-containing compounds catalyze a variety of reactions, such as acyl transfers, elimination reactions, allylic rearrangements, oxidations and reductions. These compounds in an optically active state, catalyze reactions of one enantiomer of a racemate more than the other, and asymmetric induction results. Thus enantiomers of racemates can be caused to react selectively to form optically active products. Conversely the reactions of reagents that react to form a new asymmetric center can be catalyzed by these optically active host compounds, and provide products in which one enantiomer predominates. Reductions of unsymmetrical ketones to secondary alcohols with aluminum or borohydride reagents complexed to 23, 23a, 111 or 19 provide examples. In those compounds that contain an (SS)-binaphthyl unit performs the same kinds of tasks.

I claim:

1. A compound of the formula $$\left[ [-S-O-]_s - [-T-O-]_t - [U-O-]_u - [V-O-]_v \right] \quad I$$

where
—S— =

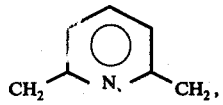

$s = 2$ through 4,
and $t=u=v=0$;
where
—S— = U = the same initially mentioned above units, T=V= —CH$_2$—CH$_2$—,
$s=u=1$,
$t = 1$ through 6,
$v = 0$, and 1 through 6;
where
—S— = U =

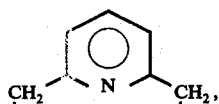

T=V= 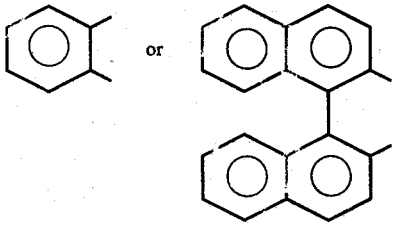

$s=u=1$,
$t=v=1$;
where
—S— =

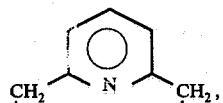

T=V= 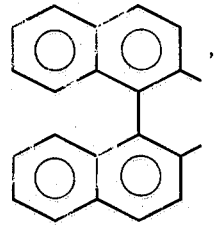

U= 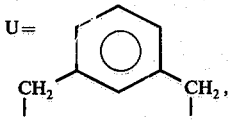

$s=t=u=v=1$;
where
—S— =

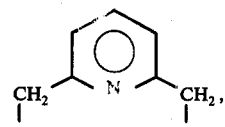

T=V= 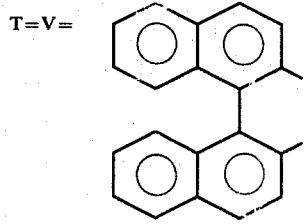

U = —(CH$_2$)$_5$—,
$s=t=u=v\ 1$;
where
—S— =

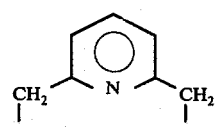

T=V=

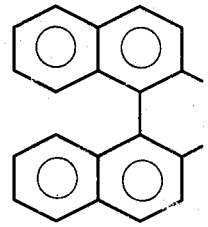

U = —CH$_2$—CH$_2$—,
$s=t=v=1$,
$u = 2$.

2. A compound according to claim 1 having the formula:

$$\overline{\left[-S-O-\right]_s}$$

where
—S— =

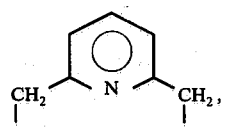

$s = 2$ through 4.

3. A compound according to claim 1 having the formula:

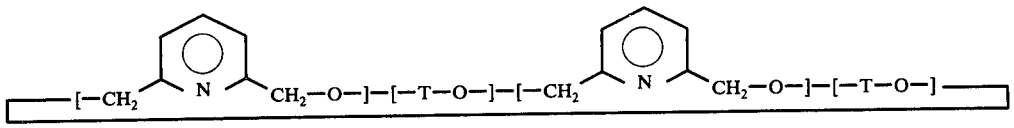
where
—S— =
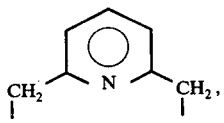
$t = 2$ through 7.
4. A compound according to claim 1 having the formula:
—[S—O—]—[—CH$_2$—CH$_2$—O—]$_t$—[S—O—]—[—CH$_2$—CH$_2$—O—]$_v$—
where
—S— =
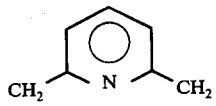
$t = 1$ through 6
$v = 0, 1$ through 6.
5. A compound according to claim 1 having the formula:
—[—CH$_2$ 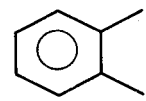 CH$_2$—O—]—[—T—O—]—[—CH$_2$ 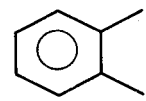 CH$_2$—O—]—[—T—O—]—
where
T =
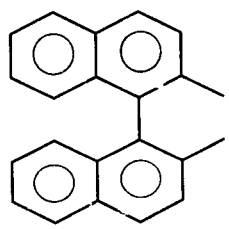
6. A compound according to claim 1 having the formula:
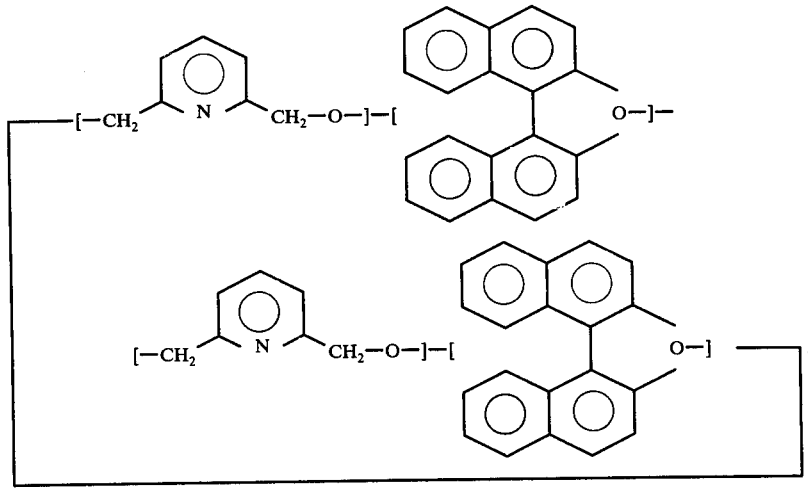
7. A compound according to claim 1 having the formula:

13. A compound according to claim 2 having the formula:
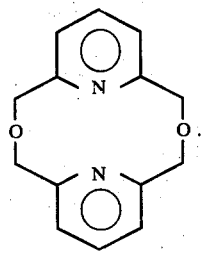
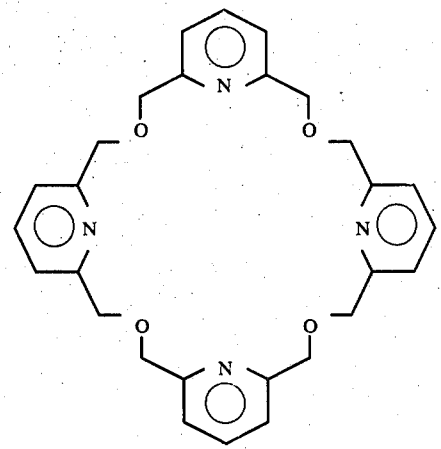

UNITED STATES PATENT OFFICE
CERTIFICATE OF CORRECTION

Patent No. 4,080,337                    Dated  March 21, 1978

Inventor(s)   Donald J. Cram

It is certified that error appears in the above-identified patent and that said Letters Patent are hereby corrected as shown below:

Cover, "[73] Assignee: The Upjohn Company, Kalamazoo, Michigan" should read -- [73] Assignee: Regents of the University of California, Berkeley, California --.

Column 2, lines 18-21 figure should appear as shown below instead of as in the patent.

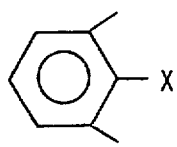

Column 9, lines 26-38, structure 13 should appear as shown below instead of as in the patent.

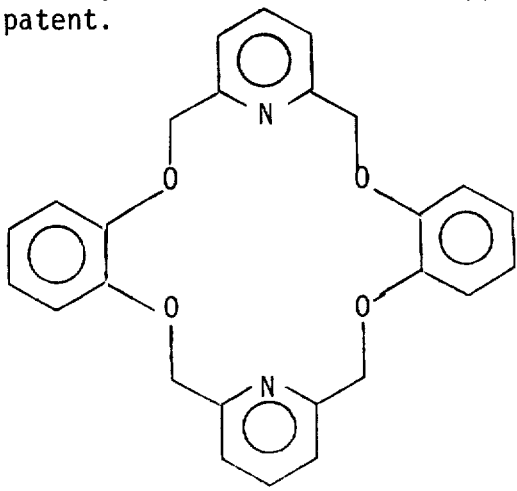

13

UNITED STATES PATENT OFFICE
CERTIFICATE OF CORRECTION

Patent No. 4,080,337　　　　　　　　　Dated March 21, 1978

Inventor(s) Donald J. Cram

It is certified that error appears in the above-identified patent and that said Letters Patent are hereby corrected as shown below:

Column 10, line 21, structures 1 and 4 should appear as shown below instead of as in the patent.

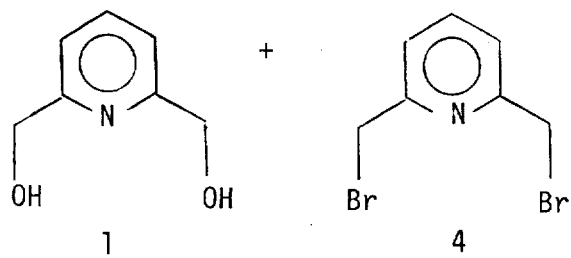

Column 11, structure (S)-18 should appear as shown below instead of as in the patent.

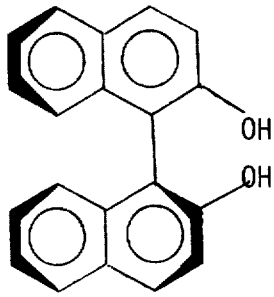

UNITED STATES PATENT OFFICE
CERTIFICATE OF CORRECTION

Patent No. 4,080,337          Dated March 21, 1978

Inventor(s) Donald J. Cram

It is certified that error appears in the above-identified patent and that said Letters Patent are hereby corrected as shown below:

Column 11, structure between structures (S)-20 and (SS)-22 should appear as shown below instead of as in the patent.

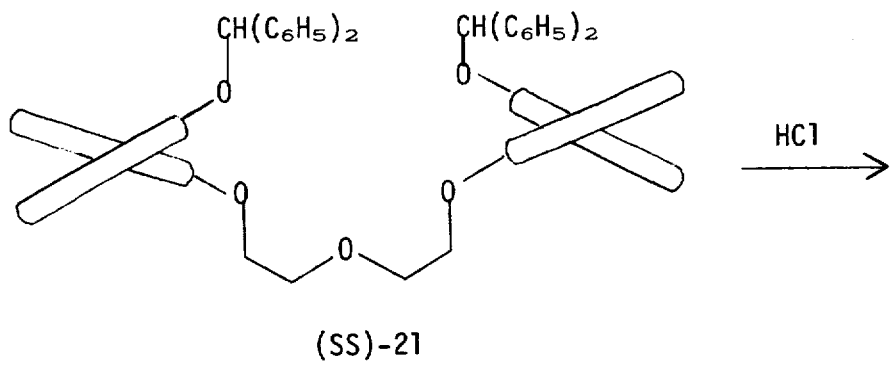

(SS)-21

Column 13, under top structure should appear -- (SS)-23 --.
Column 17, lines 35-35 the structure should appear as shown below instead of as in the patent.

UNITED STATES PATENT OFFICE
CERTIFICATE OF CORRECTION

Patent No. 4,080,337  Dated March 21, 1978

Inventor(s) Donald J. Cram

It is certified that error appears in the above-identified patent and that said Letters Patent are hereby corrected as shown below:

Column 24, lines 1-12, structure 104 should appear as shown below instead of as in the patent.

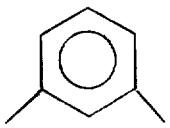

Column 24, lines 25-33, structure 101 should appear as shown below instead of as in the patent.

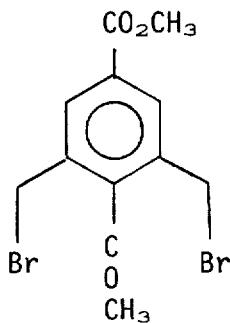

UNITED STATES PATENT OFFICE
CERTIFICATE OF CORRECTION

Patent No. 4,080,337                    Dated    March 21, 1978

Inventor(s)   Donald J. Cram

It is certified that error appears in the above-identified patent and that said Letters Patent are hereby corrected as shown below:

Column 33, after line 45 "        " should appear as follows.

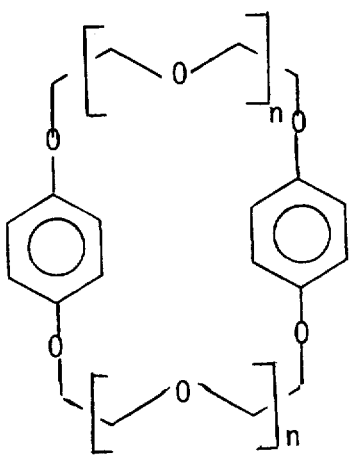

159, n = 2

161, n = 3

163, n - 4

UNITED STATES PATENT OFFICE
CERTIFICATE OF CORRECTION

Patent No. 4,080,337    Dated   March 21, 1978

Inventor(s)   Donald J. Cram

It is certified that error appears in the above-identified patent and that said Letters Patent are hereby corrected as shown below:

Column 34, lines 17-45, beginning "Similarly, multiheteromacrocycles 164-171 are prepared by the sequences shown. . . . " to "171, n = 8" should appear in column 33, under "162, n = 4 ".

Column 34, under bottom most structure "     " should read -- 173 --.
Column 35, under ring structure on right of arrow "     " should read -- 174 --.
Column 42, lines 6-11, structure 4 should appear as follows instead of as in the patent.

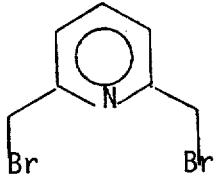

Column 55, approximately lines 35-45, under the structure "     " should read -- 49 --.
Column 57, lines 1 - 14 approximately, under the structure "     " should read -- 45 --.
Column 57, lines 15-28 approximately, under the structure "     " should read -- 89 --.
Column 58, lines 7-11 approximately, under the structure "     " should read -- 95 --.
Column 58, lines 17-22, approximately, under the structure "     " should read -- 96 --.
Colum 69, structure (SS)-174a, the bottom portion of the structure should appear as below instead of as in the patent.

UNITED STATES PATENT OFFICE
CERTIFICATE OF CORRECTION

Patent No. 4,080,337  Dated March 21, 1978

Inventor(s) Donald J. Cram

It is certified that error appears in the above-identified patent and that said Letters Patent are hereby corrected as shown below:

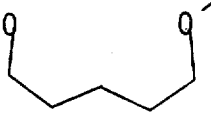

Column 72, Table I, for compound 177 the last three columns should read as follows instead of as in the patent.

-- 18    9.5x10⁴    2.5x10hu --.
                              5

Column 82, lines 1-10 approximately, Complex of 71 should read as shown below instead of as appears in the patent.

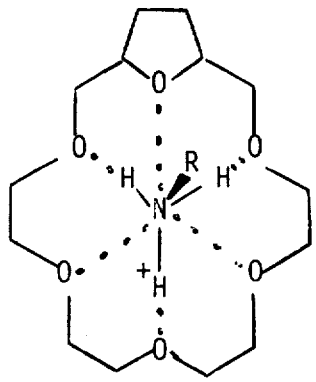

UNITED STATES PATENT OFFICE
CERTIFICATE OF CORRECTION

Patent No. 4,080,337     Dated March 21, 1978

Inventor(s) Donald J. Cram

It is certified that error appears in the above-identified patent and that said Letters Patent are hereby corrected as shown below:

Column 87, Table II, approximately line 40, "         " should read
-- 24.5     1.26     1.29     1.73     0.75 --.
Column 91, line 35, "(4.8-5.39)" should read -- (4.8-5.3) --.
Column 95, in Table IV, chemical ring structure at the top should appear
    as shown below instead of as in the patent.

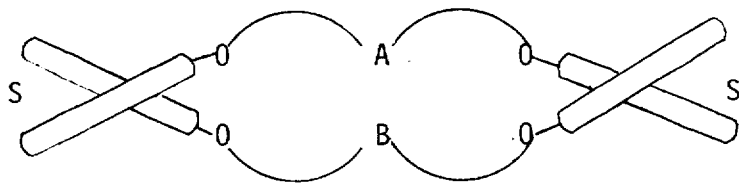

UNITED STATES PATENT OFFICE
CERTIFICATE OF CORRECTION

Patent No. 4,080,337  Dated March 21, 1978

Inventor(s) Donald J. Cram

It is certified that error appears in the above-identified patent and that said Letters Patent are hereby corrected as shown below:

Column 101, claim 9, the chemical structure should appear as below instead of as in the patent.

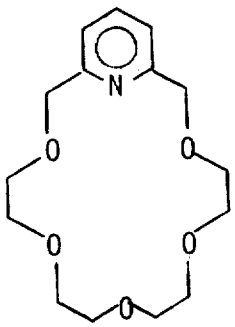

[SEAL]

Attest:

RUTH C. MASON
*Attesting Officer*

Signed and Sealed this

Twelfth Day of September 1978

DONALD W. BANNER
*Commissioner of Patents and Trademarks*